(12) United States Patent
Wu et al.

(10) Patent No.: US 6,716,642 B1
(45) Date of Patent: *Apr. 6, 2004

(54) INDIVIDUALLY ADDRESSABLE MICRO-ELECTROMAGNETIC UNIT ARRAY CHIPS IN HORIZONTAL CONFIGURATIONS

(75) Inventors: Lei Wu, San Diego, CA (US); Xiaobo Wang, San Diego, CA (US); Jing Cheng, Beijing (CN); Weiping Yang, San Diego, CA (US); YuXiang Zhou, Beijing (CN); LiTian Liu, Beijing (CN); Junquan Xu, Beijing (CN)

(73) Assignee: Aviva Biosciences Corporation, San Diego, CA (US)

( * ) Notice: Subject to any disclaimer, the term of this patent is extended or adjusted under 35 U.S.C. 154(b) by 345 days.

This patent is subject to a terminal disclaimer.

(21) Appl. No.: 09/685,410

(22) Filed: Oct. 10, 2000

Related U.S. Application Data

(63) Continuation-in-part of application No. PCT/US99/21417, filed on Sep. 17, 1999, and a continuation-in-part of application No. 09/399,299, filed on Sep. 17, 1999, now Pat. No. 6,355,491.

(30) Foreign Application Priority Data

Mar. 15, 1999 (CN) ........................................ 99104113 A

(51) Int. Cl.⁷ ............................................. G01N 33/543
(52) U.S. Cl. ............. 436/518; 422/186.15; 422/186.01; 422/50; 435/7.92; 435/15; 435/68.1; 435/7.1; 435/7.2; 435/6; 250/338.2; 436/148
(58) Field of Search ................... 436/518, 148; 435/6, 7.92, 68.1, 15, 7.2, 7.1; 422/186.15, 50, 186.01; 250/338.2

(56) References Cited

U.S. PATENT DOCUMENTS

| | | |
|---|---|---|
| 4,160,645 A | 7/1979 | Ullman |
| 4,275,149 A | 6/1981 | Litman et al. |
| 4,318,980 A | 3/1982 | Boguslaski et al. |
| 4,777,019 A | 10/1988 | Dandekar |
| 4,894,443 A | 1/1990 | Greenfield et al. |
| 5,122,227 A | 6/1992 | Ott |
| 5,202,231 A | 4/1993 | Drmanac et al. |
| 5,225,969 A | 7/1993 | Takaya et al. |
| 5,238,810 A | 8/1993 | Fujiwara et al. |
| 5,252,493 A | 10/1993 | Fujiwara et al. |
| 5,252,743 A | 10/1993 | Barrett et al. |
| 5,439,586 A | 8/1995 | Richards et al. |
| 5,445,934 A | 8/1995 | Fodor et al. |
| 5,605,662 A | 2/1997 | Heller et al. |

(List continued on next page.)

FOREIGN PATENT DOCUMENTS

| | | | | |
|---|---|---|---|---|
| DE | 43 36 417 | | 4/1994 | |
| WO | WO 94/16101 | | 7/1994 | |
| WO | WO 98/14641 | | 4/1998 | |
| WO | WO 00/33062 | * | 6/2000 | .......... G01N/27/26 |
| WO | 00/54882 | | 9/2000 | |
| WO | 02/31505 | | 4/2002 | |

OTHER PUBLICATIONS

Ahn and Allen, IEEE Transactions on Magnets, 30:73–79 (1994).

Ahn and Allen, Electrochemical Society Proceedings, 95–18:411–425.

Ahn et al., Journal of Microelectromechanical Systems, 5:151–158 (1996).

(List continued on next page.)

*Primary Examiner*—Long V. Le
*Assistant Examiner*—Deborah A Davis
(74) *Attorney, Agent, or Firm*—David R. Preston & Associates; David Preston

(57) ABSTRACT

The present invention provides electromagnetic chips and electromagnetic biochips having arrays of individually addressable micro-electromagnetic units, as well as methods of utilizing these chips for directed manipulation of microparticles and micro-structures such as biomolecules and chemical reagents.

15 Claims, 33 Drawing Sheets

U.S. PATENT DOCUMENTS

| | | | |
|---|---|---|---|
| 5,612,474 | A | 3/1997 | Patel |
| 5,624,711 | A | 4/1997 | Sundberg et al. |
| 5,632,957 | A | 5/1997 | Heller et al. |
| 5,653,939 | A | 8/1997 | Hollis et al. |
| 5,655,665 | A | 8/1997 | Allen et al. |
| 5,779,976 | A | 7/1998 | Leland et al. |
| 5,833,760 | A | 11/1998 | Huh et al. |
| 5,849,486 | A | 12/1998 | Heller et al. |
| 5,856,174 | A | 1/1999 | Lipshutz et al. |
| 5,858,666 | A | 1/1999 | Weiss |
| 5,874,554 | A | 2/1999 | Gamble et al. |
| 5,883,760 | A | 3/1999 | Yamada et al. |
| 6,051,380 | A * | 4/2000 | Sonsnowski et al. .......... 435/6 |
| 6,187,164 | B1 | 2/2001 | Warren et al. |
| 6,355,491 | B1 * | 3/2002 | Zhou et al. ................. 436/518 |

OTHER PUBLICATIONS

Baselt et al, Biosensors & Bioelectronics, 13:731–739 (1998).
Batra et al., Molecular Immunology, 30:379–386 (1993).
Blanchard et al., Biosensors & Bioelectronics, 11:687–690 (1996).
Brown and Hartwell, Nature Genetic, 18:91–93 (1998).
Chee et al., Science, 274:610–614 (1996).
Drmanac et al., Nature Biotechnology, 16:54–58 (1998).
Edelstein et al., Biosensors & Bioelectronics, 14:805–813 (2000).
Gascoyne et al., IEEE Transactions on Industry Applications, 33:670–678 (1997).
Huston et al., Proc. Natl. Acad. Sci. USA, 85:5879–5883 (1988).
Ju et al., Proc. Natl. Acad. Sci. USA, 92:4347–4351 (1995).
Ladurner and Fersht, J. Mol. Biol., 273:330–337 (1997).
Liakopoulos et al, TRANSDUCERS '97, pp. 485–488 (1997).
Livache et al, Analytical Biochemistry, 255:188–194 (1998).
Marton et al, Nature Medicine, 4:1293–1301 (1998).
Milner et al., Nature Biotechnology, 15:537–541 (1997).
Newton et al, Biochemistry, 35:545–553 (1996).
Ruan et al., The Plant Journal, 15:821–833 (1998).
Schena et al., Science, 270:467–470 (1995).
Shoemaker et al., Nature Genetics, 14:450–456 (1996).
Sosnowski et al., Proc. Natl. Acad. Sci. USA, 94:1119–1123 (1997).
Sun et al., Cytometry, 33:469–475 (1998).
Whitlow et al., Protein Engineering, 6:989–995 (1993).
Wang, D. et al., Science, 280:1077–1082 (1998).
Wang, X. et al, IEEE Transactions on Industry Applications, 33:660–669 (1997).
Wodicka et al., Nature Biotechnology, 15:1359–1367 (1997).

* cited by examiner

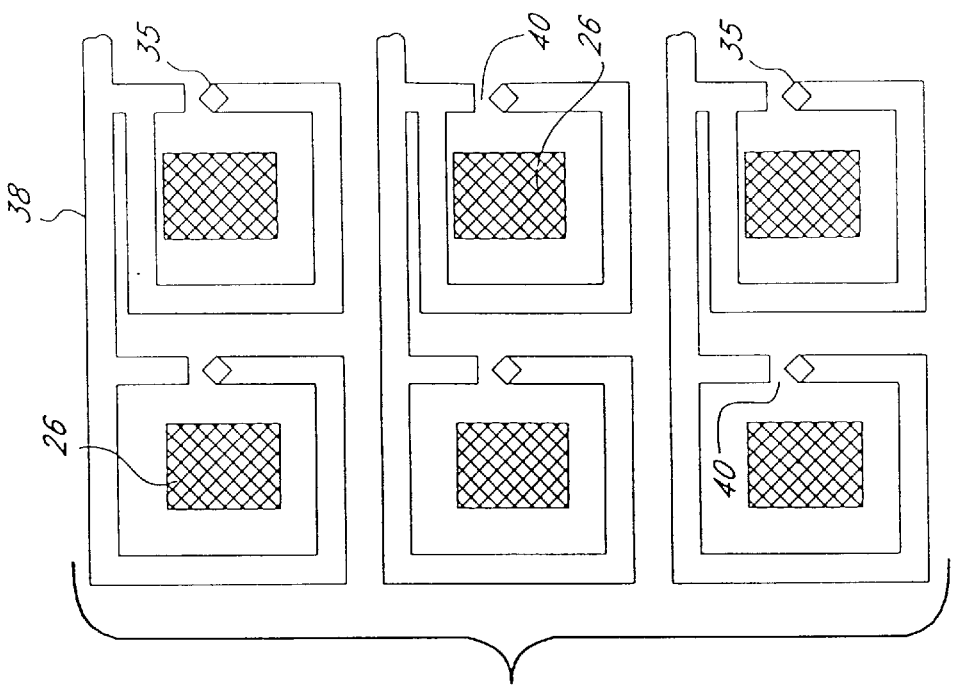
FIG. 8
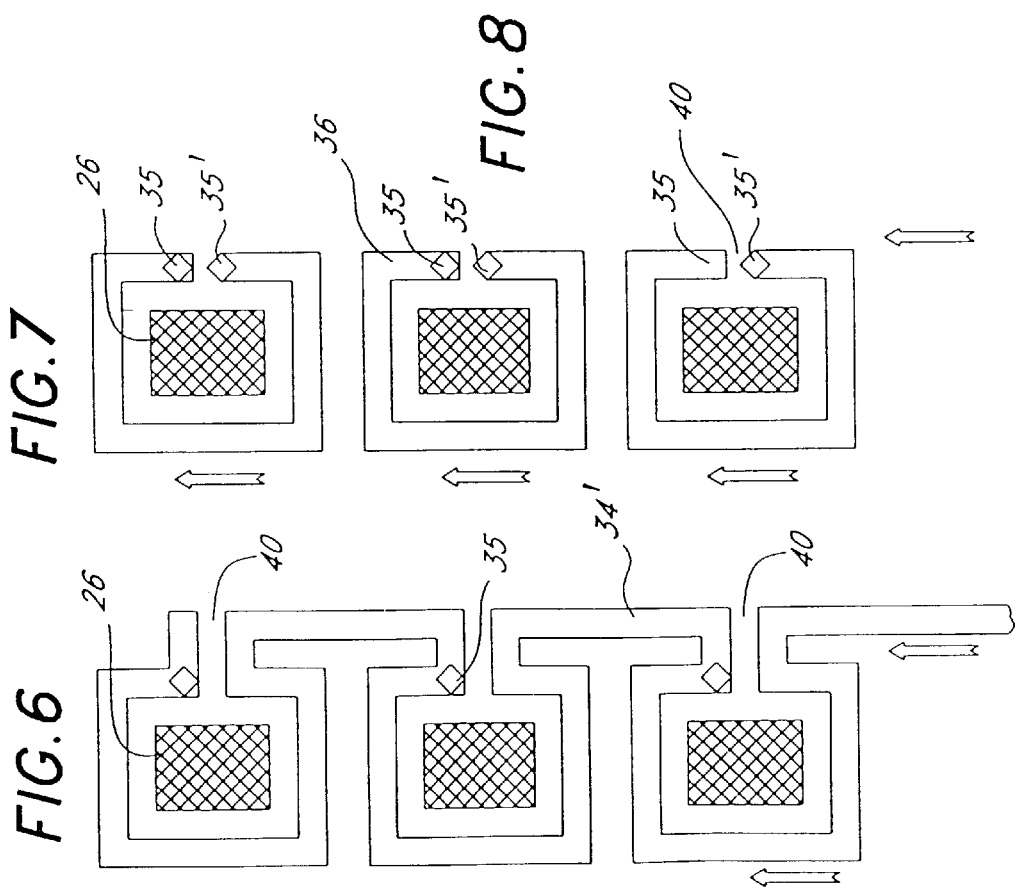
FIG. 7
FIG. 6

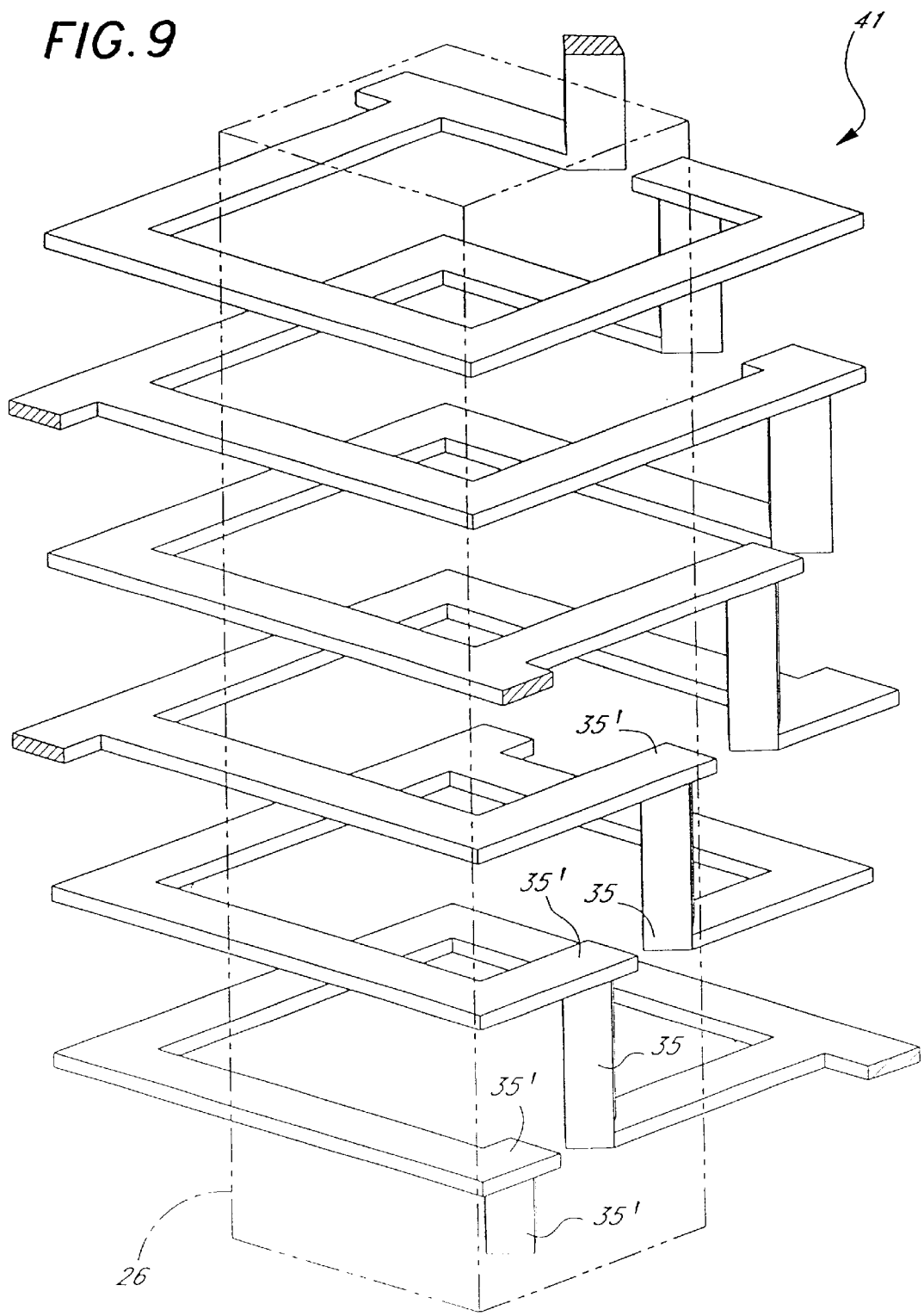

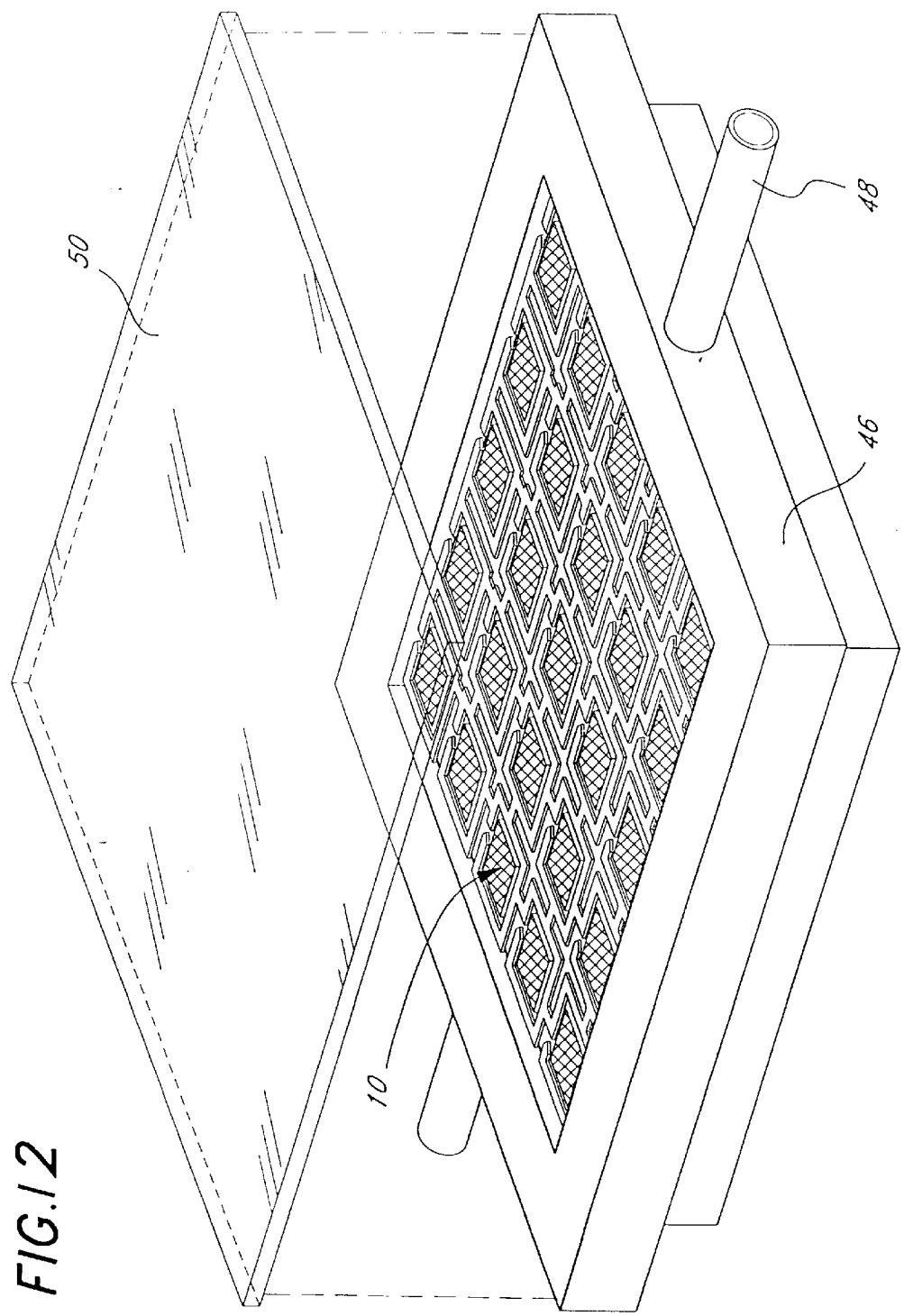

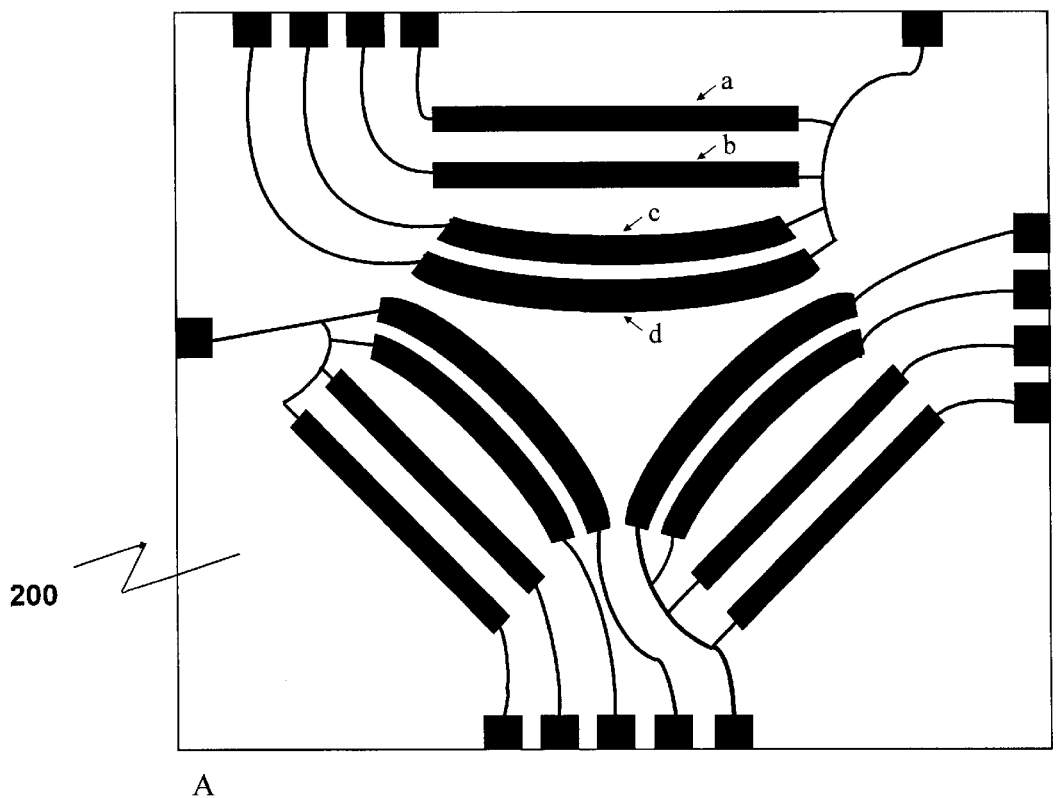
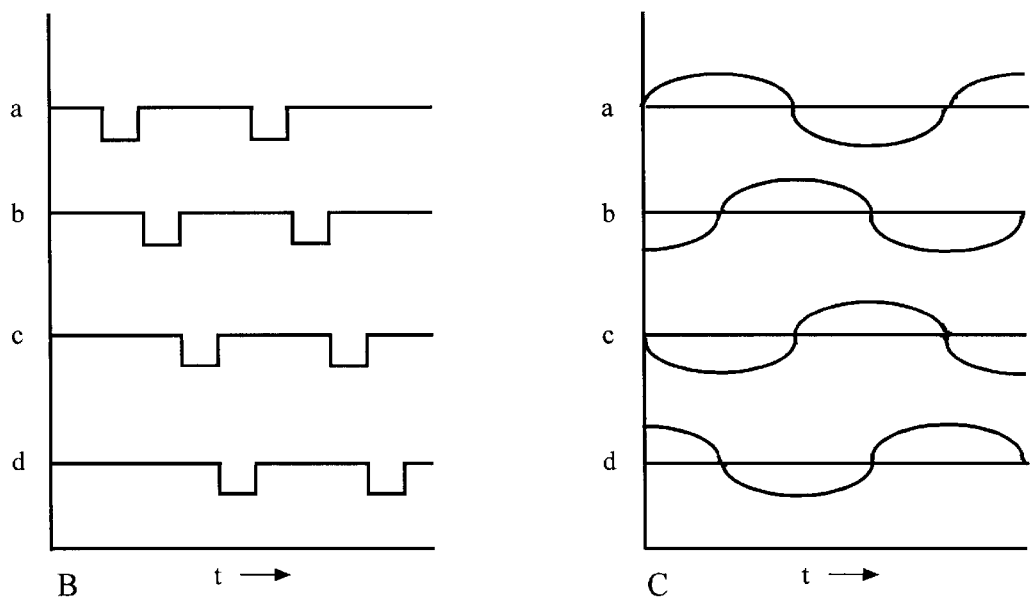
FIG. 39A

INDIVIDUALLY ADDRESSABLE MICRO-ELECTROMAGNETIC UNIT ARRAY CHIPS IN HORIZONTAL CONFIGURATIONS

The present application is a continuation-in-part of U.S. patent application Ser. No. 09/399,299 entitled "Individually Addressable Micro-Electromagnetic Unit Array Chips" filed on Sep. 17, 1999 now U.S. Pat. No. 6,355,491 which is incorporated herein by reference in its entirety; and claims benefit of priority to the following applications, which are incorporated by reference in their entirety herein: People's Republic of China Application No. 99104113.5 entitled "Individually Addressable Micro-Electromagnetic Unit Array Chips, Electromagnetic Biochips and Their Applications," filed on Mar. 15, 1999; and PCT application No. PCT/US99/21417 entitled "Individually Addressable Micro-Electromagnetic Unit Array Chips" filed on Sep. 17, 1999.

The following applications are incorporated herein by reference in their entirety:

PCT Application No. PCT/US00/25381 filed on Sep. 15, 2000, published as WO 02/12896, entitled "Method for Manipulating Moieties in Microfluidic Systems" naming as inventors Xiaobo Wang, Lei Wu, Jing Cheng, Weiping Yand and Junquan Xu;

U.S. patent application Ser. No. 09/678,263, filed on Oct. 3, 2000, now U.S. Pat. No. 6,596,143, entitled "Apparatus for Switching and Manipulating Particles and Method of Use Thereof" and naming as inventors Xiaobo Wang, Weiping Yang, JunQuan Xu, Jing Cheng and Lei Wu, which corresponds to People's Republic of China Application Number 00129043.6 entitled "Apparatus for Switching and Manipulating Particles and Method of Use Thereof," filed Sep. 27, 2000;

U.S. patent application Ser. No. 09/679,024 filed on Oct. 4, 2000, entitled "Apparatus Containing Multiple Active Force Generating Elements and Uses Thereof" and naming as inventors Xiaobo Wang, Jing Cheng, Lei Wu, JunQuan Xu and Weiping Yang, which corresponds to People's Republic of China Application Number 00130563.8, filed Sep. 30, 2000;

U.S. patent application Ser. No. 09/636,104 filed Aug. 10, 2000, entitled "Methods for Manipulating Moieties in Microfluidic Systems;"

U.S. patent application Ser. No. 09/684,081 filed Aug. 25, 2000, entitled "Methods and Compositions for Identifying Nucleic Acid Molecules Using Nucleolytic Activities and Hybridization;"

U.S. patent application Ser. No. 09/686,737 filed Oct. 10, 2000, entitled "Compositions and Methods for Separation of Moieties on Chips" naming as inventors JunQuan Xu, Xiaobo Wang, Jing Cheng, Weiping Yang and Lei Wu that corresponds to People's Republic of China Application No. 00131649.4, filed Oct. 9, 2000; and U.S. Provisional Application No. 60/239,299 filed Oct. 10, 2000, entitled "An Integrated Biochip System for Sample Preparation and Analysis" naming as inventors Jing Cheng et al.

TECHNICAL FIELD

The present application concerns micromachined or microfabricated devices known as "biochips" and more particularly biochips employing magnetic forces and methods of utilizing such biochips for performing chemical, biological and biochemical reactions and assays.

BACKGROUND

As a novel and emerging technology in life science and biomedical research during last several years, biochip technology can be applied to many areas of biology, biotechnology and biomedicine including point-mutation detection, DNA sequencing, gene expression, drug screening and clinical diagnosis. Biochips refer to miniaturized devices that can be used for performing chemical and biochemical reactions. Biochips are produced using microelectronic and microfabrication techniques as used in semiconductor industry or other similar techniques, and can be used to integrate and shrink the currently discrete chemical or biochemical analytical processes and devices into microchip-based apparatus. Recent scientific literature shows a plethora of uses for these devices.

The reader s attention is drawn to the following articles for an appreciation of the breadth of biochip uses. Rapid determination of single base mismatch mutations in DNA hybrids by direct electric field control by Sosnowski, R. G. etal. (Proc. Natl. Acad. Sci., USA, 94:1119–1123 (1997)) and Large-scale identification, mapping and genotyping of single-nucleotide polymorphisms in the human genome by Wang, D. G. et al. (Science, 280: 1077–1082 (1998)) show current biochip use in detection of point mutations. Accurate sequencing by hybridization for DNA diagnostics and individual genomics by Drmanac, S. et al. (Nature Biotechnol. 16: 54–58 (1998)), Quantitative phenotypic analysis of yeast deletion mutants using a highly parallel molecular barcoding strategy by Shoemaker, D. D. et al. (Nature Genet., 14:450–456 (1996)), and Accessing genetic information with high density DNA arrays. by Chee, M et al., (Science, 274:610–614 (1996)) show biochip technology used for DNA sequencing. The use of biochip technology to monitor gene expression is shown in Genome-wide expression monitoring in *Saccharomyces cerevisiae* by Wodicka, L. et al. (Nature Biotechnol. 15:1359–1367 (1997)), Genomics and human disease—variations on variation. by Brown, P. O. and Hartwell, L. and Towards Arabidopsis genome analysis: monitoring expression profiles of 1400 genes using cDNA microarrays by Ruan, Y. et al. (The Plant Journal 15:821–833 (1998)). The use of biochips in drug screening is illustrated in Selecting effective antisense reagents on combinatorial oligonucleotide arrays by Milner, N. et al. (Nature Biotechnol., 15:537–541 (1997)), and Drug target validation and identification of secondary drug target effects using DNA microarray by Marton, M. J. et al. (Nature Medicine, 4:1293–1301 (1998)). Examples of clinical diagnostic use of biochips is illustrated in Cystic fibrosis mutation detection by hybridization to light-generated DNA probe arrays by Cronin, M. T. et al. (Human Mutation, 7:244–255 (1996)), and Polypyrrole DNA chip on a silicon device: Example of hepatitis C virus genotyping by Livache, T. et al. (Anal. Biochem. 255:188–194 (1998)). These references are intended to give a notion of the wide range of biochip uses.

A variety of biochips have biomolecules (for example, oligonucleotides, cDNA and antibodies) immobilized on their surfaces. There are a number of different approaches to make such chips. For example, the light-directed chemical synthesis process developed by Affymetrix (for example, U.S. Pat. Nos. 5,445,934 and 5,856,174) is a method of synthesizing biomolecules on chip surfaces by combining solid-phase photochemical synthesis with photolithographic fabrication techniques. The chemical deposition approach developed by Incyte Pharmaceutical uses pre-synthesized cDNA probe for directed deposition onto chip surfaces (see, for example, U.S. Pat. No. 5,874,554). The contact-print method developed by Stanford University uses high-speed, high-precision robot-arms to move and control liquid-dispense head for directed cDNA deposition and printing onto chip surfaces (see, for example, Schena, M. et al. Science 270:467–70 (1995)). The University of Washington at Seattle developed a single-nucleotide probe synthesis method by using four piezoelectric deposition heads, which are loaded separately with four types of nucleotide molecules to achieve required deposition of nucleotides and simultaneous synthesis on chip surfaces (see for example, Blanchard, A. P. et al. Biosensors & Bioelectronics 11:687–90 (1996)). Hyseq, Inc. has developed passive membrane devices for sequencing genomes (see, for example, U.S. Pat. No. 5,202,231).

There are two basic types of biochips, for example, passive and active. Passive biochips refer to those on which chemical or biochemical reactions are dependent on passive diffusion of sample molecules. In active biochips reactants are actively moved or concentrated by externally applied forces so that reactions are dependant not only on simple diffusion but also on the applied forces. The majority of the available biochips, for example, oligonucleotide-based DNA chips from Affymetrix and cDNA-based biochips from Incyte Pharmaceuticals, belong to the passive type. There are structural similarities between active and passive biochips. Both types of biochips employ of arrays of different immobilized ligands or ligand molecules. By using various markers, detectable markers, detection systems and indicator molecules (for example, fluorescent dye molecules), the reaction between ligands and other molecules can be monitored and quantified. Thus, an array of different ligands immobilized on a biochip allows for the reaction and monitoring of multiple analyte molecules.

Many current passive biochip designs do not take full advantage of microfabrication and microelectronic technologies. Passive biochips cannot be readily used to achieve fully integration and miniaturization of the entire bioanalytical system from the front-end sample preparation to final molecular quantification/detection. In addition, passive biochips have other disadvantages including low analytical sensitivity, a long reaction time, and difficulties associated with control of temperature, pressure, and electrical fields at individual sites (called units) on the chip surfaces as well as difficulties in controlling the local concentrations of molecules.

On the other hand, active biochips allow versatile functions of molecular manipulation, interaction, hybridization reaction and separation (such as PCR and capillary electrophoresis) by external forces through means such as microfluidic manipulation and electrical manipulation of molecules. However, many such biochips cannot be readily used in high throughput applications. The electronic biochips developed by Nanogen can manipulate and control sample biomolecules with electrical field generated by microelectrodes, leading to significant improvement in reaction speed and detection sensitivity over passive biochips (see, for example, U.S. Pat. Nos. 5,605,662, 5,632,957, and 5,849,486). However, to effectively move biomolecules in their suspension/solutions with electrical fields, electrical conductivity of solutions has to be very low. This significantly limits the choice of buffer solutions used for biochemical assays. Many enzymes and other biomolecules are denatured under conditions of low ionic strength and/or serious non-specific binding occurs to chip surfaces.

The present invention provides a new type of active biochips in which magnetic forces are generated by individually addressable (controllable) units arranged in an array. The magnetic forces are used to control and manipulate magnetically-modified molecules and particles and to promote molecular interactions and/or reactions on the surfaces of chips. Magnetic forces have been widely employed in biological, biochemical and biomedical applications. For example, magnetic-activated cell sorting is a common technique based on selectively binding magnetic particles that has been modified with antibodies to specific cell types within a mixture. After binding, the cell-magnetic particle complexes from the cell mixture are selectively removed using a magnet. (See, for example, Miltenyi, S. et al. High gradient magnetic cell-separation with MACS (Cytometry 11:231–236 (1990)). Other examples were given in U.S. Pat. No. 5,439,586 describing a three-dimensional magnetic filter for separating magnetically labeled particles from non-magnetic particles in a flow stream and in U.S. Pat. No. 5,655,665 disclosing a micromachined magnetic particle separator for microfluidic magnetic separations.

BRIEF DESCRIPTION OF THE FIGURES

FIG. 6 depicts a schematic diagram of one aspect of a micro-electromagnetic unit of the present invention as seen from above showing the electric current flow for turning on the unit (for example, magnetizing the magnetic core). Although shown in a vertical configuration, the depicted electromagnetic units can optionally be provided independently in a horizontal configuration.

FIG. 7 depicts a schematic diagram showing the form of a first set of conductive traces used to produce a micro-coil around each ferromagnetic core for one aspect of the present invention. Although shown in a vertical configuration, the depicted electromagnetic units can optionally be provided independently in a horizontal configuration.

FIG. 8 depicts a schematic diagram showing the form of a second set of conductive traces used to produce a micro-coil around each ferromagnetic core in one aspect of the present invention. Although shown in a vertical configuration, the depicted electromagnetic units can optionally be provided independently in a horizontal configuration.

FIG. 9 depicts a schematic diagram showing the form of a third set of conductive traces used to produce a micro-coil around each ferromagnetic core in one aspect of the present invention. Although shown in a vertical configuration, the depicted micro-coil can be provided in a horizontal configuration.

FIG. 12 depicts a schematic diagram showing a biochip of one aspect of the present invention equipped with a fluid chamber and a window to allow optical detection. Although shown in a vertical configuration, the depicted electromagnetic units can optionally be provided independently in a horizontal configuration.

FIG. 24A depicts a chip having sixteen individually addressable electromagnetic units, whereas FIG. 24B depicts two groups of eight individually addressable electromagnetic units. The chip depicted in FIG. 24B is a preferred structure for traveling magnetic wave application.

FIG. 38A, FIG. 38B and FIG. 38C depict the movement of a magnetic particle along a traveling magnetic wave as micro-electromagentic units are energized and deenergized.

FIG. 39 depicts one aspect of a particle switch using traveling wave magentophoresis of the present invention. FIG. 39A depicts a switch (200). FIG. 39B depicts DC currents used to make traveling magnetic waves and FIG. 39C depicts AC currents used to make traveling waves.

SUMMARY

Figure 1:
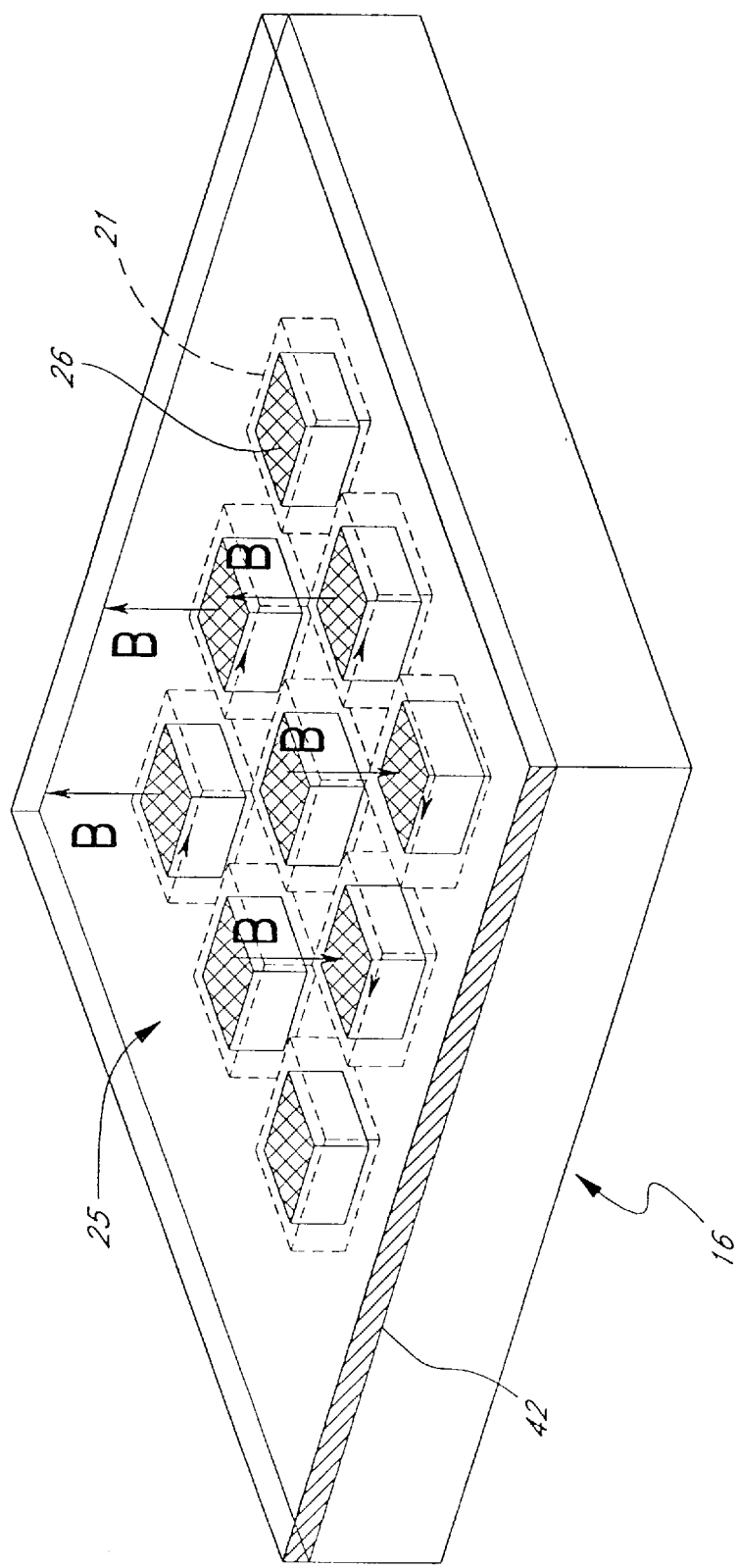
FIG. 1 depicts a schematic diagram for one aspect of a structure of an individually addressable micro-electromagnetic unit array chip of the present invention. Although shown in a vertical configuration, the depicted electromagnetic units can optionally be provided independently in a horizontal configuration.

The present invention recognizes that the ability to manipulate the location moieties such as biomolecules and particles can be utilized to automate, streamline and miniaturize a wide variety of biological, chemical, mechanical and physical processes. In particular, the ability to specifically and precisely manipulate the location of moieties such as biological moieties can be utilized for a variety of methods, such as the detection of such moieties or their binding partners in samples, the diagnosis of disease states, conditions or etiological agents, or the diagnosis of disease states, conditions or infection by etiological agents.

The present invention discloses electromagnetic biochips that comprise individually addressable micro-electromagnetic units arranged that are optionally provided in one or more arrays. An electromagnetic biochip may have single or multiple micro-electromagnetic unit arrays. Each unit is capable of inducing magnetic field upon applying electric current, and is selectively addressable so that the magnetic filed generated by the unit can be turned on or off and can be modulated in terms of the field intensity and field direction by altering electric current applied to the unit. The alteration of magnetic fields on or within the chip s surface is used to manipulate magnetic particles that optionally can include moieties such as biomolecules or particles, including cells. The magnetic particles or molecules are actually guided to predetermined locations on the chip s surface. The chip s surface or a portion of a chip can be chemically modified to form a functional layer for immobilizing ligand molecules so that affinity interaction or specific biochemical reactions may occur between the ligand molecules and the magnetically guided particles or molecules. Magnetic guiding and manipulation of particles or molecules alters the local concentration of these materials to increase the rate of biochemical or chemical reactions and the sensitivity of various assays. Because ionic strength and other buffer characteristics have little or no effect on magnetic fields, biochemically optimized buffer conditions can be selected. Furthermore, no strong electrical fields are present to complicate the assay or reaction by electrochemistry.

The present invention further discloses methods for manipulating magnetic particles on electromagnetic chips. The particles may be suspended in a fluid (either aqueous or non-aqueous) or in the air or even vacuum. When a micro-electromagnetic unit is energized, magnetic particles in the vicinity of that unit will experience magnetic forces and are attracted to the surface of the energized unit. That is, where a suspension of magnetic particles covers the entire chip array, energizing a single electromagnetic unit will affect only particles in the immediate vicinity of the unit. However, by sequentially energizing units it is possible to move and concentrate all of the magnetic particles suspended over the entire array. Such coordinated movement is referred to as manipulation and such manipulation can be controlled by switching units on and off in a predetermined sequence. Manipulation of magnetic particles also refers to the change and control of particle position, velocity and other kinetic properties by changing electric currents applied to micro-electromagnetic units and accordingly altering magnetic field distribution and forces acting on particles. Depending on the application, all units or some of the units may be energized simultaneously. Alternatively, units may be energized one-at-a-time.

The present invention further discloses methods for manipulating biomolecules/bioparticles, chemical-reagent molecules, drug molecules or any other molecules or particles with an electromagnetic biochip. These biochips can generally be used to manipulate any kind of magnetic particle. For controlling and handling non-magnetic particles and/or biomolecules, these materials are first magnetically modified. For example, the molecules may be covalently attached or physically absorbed to the surface of magnetic particles. The biomolecules may be proteins (for example, antibodies, antigens and receptors), nucleic acids (for example, single stranded DNA or RNA) or other molecules such as lipids or carbohydrates. The electromagnetic biochip surface may be modified for immobilizing ligand molecules that are capable of interacting with molecules on the surface of the manipulated magnetic particles. Such interactions are facilitated because the magnetic particles are concentrated at specific locations on which the appropriate ligand molecules are already immobilized.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as up and down or upper or lower and the like refer to orientation of parts during use of a device. Where a term is provided in the singular, the inventors also contemplate the plural of that term. The nomenclature used herein and the laboratory procedures described below are those well known and commonly employed in the art. Where there are discrepancies in terms and definitions used in references that are incorporated by reference, the terms used in this application shall have the definitions given herein. As employed throughout the disclosure, the following terms, unless otherwise indicated, shall be understood to have the following meanings:

"Magnetic forces" refer to the forces acting on a particle due to the application of a magnetic field. In general, particles have to be magnetic or paramagnetic when sufficient magnetic forces are needed to manipulate particles. For a typical magnetic particle made of super-paramagnetic material, when the particle is subjected to a magnetic field B, a magnetic dipole $\mu$ is induced in the particle $$\mu = V_p(\chi_p - \chi_m)$$
$$= V_p(\chi_p - \chi_m)H_m$$

where $V_P$ is the particle volume, $X_p$ and $X_m$ are the volume susceptibility of the particle and its surrounding medium, $\mu_m$ is the magnetic permeability of the medium, $H_m$ is the magnetic field strength. The magnetic force $F_{magnetic}$ acting on the particle is determined by the magnetic dipole moment and the magnetic field gradient:

$$F_{magnetic} = 0.5\, V_p\, (X_p - X_m) H_m \cdot \Delta B_m,$$

where the symbols "•" and "Δ" refer to dot-product and gradient operations, respectively. Whether there is magnetic force acting on a particle depends on the difference in the volume susceptibility between the particle and its surrounding medium. Typically, particles are suspended in a liquid, nonmagnetic medium (the volume susceptibility is close to zero), thus it is necessary to utilize magnetic particles (their volume susceptibility is much larger than zero). The particle velocity $v_{particle}$ under the balance between magnetic force and viscous drag is given by:

$$v_{particle} = \frac{F_{magnetic}}{6\pi r \eta_m}$$

where r is the particle radius and $\eta_m$ is the viscosity of the surrounding medium.

A moiety is any entity, whose manipulation by electromagnetic forces is desirable, particularly when the moiety complexes or otherwise attached to a material that can be manipulated by a magnetic field. A moiety can be a solid, including a suspended solid, or can be in soluble form. A moiety can be a molecule. Molecules that can be manipulated include, but are not limited to, inorganic molecules, including ions and inorganic compounds, or can be organic molecules, including amino acids, peptides, proteins, glycoproteins, lipoproteins, glycolipoproteins, lipids, fats, sterols, sugars, carbohydrates, nucleic acid molecules (including DNA or RNA, single stranded or double stranded or combinations thereof), small organic molecules, or complex organic molecules. A moiety can also be a molecular complex, can be an organelle, can be one or more cells, including prokaryotic and eukaryotic cells, or can be one or more etiological agents, including viruses, parasites, bacteria or prions, or portions thereof. A moiety can also be a crystal, mineral, colloid, fragment, or the like, and can comprise one or more inorganic materials such as polymeric materials, metals, minerals, glass, ceramics, and the like. Moieties can also be aggregates of molecules, complexes, cells, organelles, viruses, etiological agents, crystals, colloids, or fragments. Cells can be any cells, including prokaryotic and eukaryotic cells. Eukaryotic cells can be of any type. Of particular interest are cells such as, but not limited to, white blood cells, malignant cells, stem cells, progenitor cells, fetal cells, and cells infected with an etiological agent, and bacterial cells. A moiety can be an intracellular moiety. A moiety of interest is within the definition of moiety and refers an identified moiety.

As used herein, "intracellular moiety" refers to any moiety that resides or is otherwise located within a cell, for example, located in the cytoplasm or matrix of cellular organelle, attached to any intracellular membrane, resides or is otherwise located within periplasma, if there is one, or resides or is otherwise located on cell surface, for example, attached on the outer surface of cytoplasm membrane or cell wall, if there is one. An intracellular moiety can be freed from a cell by a variety of methods, such as by lysing of the cell by a variety of methods, including sonication, enzymatic activity, osmotic shock or the like.

Ligands" or "ligand molecules refers to biochemical molecules with which other molecules can react. For instance, a ligand may be a nucleic acid molecule to which a complementary nucleic acid molecule can hybridize. A ligand may be an antibody molecule to which the corresponding antigen (epitope) can bind. A ligand can also be part of a receptor and ligand binding pair. A ligand may also include a particle on whose surface are a plurality of molecules to which other molecules may react An "array" refers to a plurality of micro-electromagnetic units on a chip. A single chip can have a plurality of arrays that are separated spatially. For example, a single chip can have two or more loci that include a plurality of micro-electromagnetic units. These loci are preferably separated spatially such that the electromagnetic forces generated at the loci do not substantially interfere with each other, but that need not be the case. For example, each locus can be individually controlled such that magnetic fields in the different loci are not activated at the same time. Alternatively, such as in traveling magnetic wave aspects of the present invention, the magnetic fields of different arrays may overlap spatially and temporally. Alternatively, micro-electromagnetic units within a locus can have the electromagnetic forces overlap spatially and temporally, such as in traveling magnetic wave applications of the present invention.

Manipulation" refers to moving or processing of a moiety, which results in one-, two- or three-dimensional movement of the moiety, in a chip format, whether within a single chip or between or among multiple chips. Non-limiting examples of the manipulations include transportation, focusing, enrichment, concentration, aggregation, trapping, repulsion, levitation, separation, isolation or linear or other directed motion of the moieties, particularly in a magnetic field.

A sample is any fluid from which components are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample. A sample can include, but is not limited to, a blood sample, white blood cells, red blood cells, neoplastic cells, malignant cells, stem cells, progenitor cells or an etiological agent. A sample can be any fluid sample, such as an environmental sample, including air samples, water samples, food samples, and biological samples, including extracts of biological samples. Biological samples can be blood, serum, saliva, urine, semen, ocular fluid, extracts of nasal swabs, throat swabs, or genital swabs or extracts of fecal material. Biological samples can also be samples of organs, tissues, or cell cultures, including both primary cultures and cell lines. A preferred sample is a blood sample.

A blood sample as used herein can refer to a processed or unprocessed blood sample, i.e., it can be a centrifuged, filtered, extracted, or otherwise treated blood sample, including a blood sample to which one or more reagents such as, but not limited to, anticoagulants or stabilizers have been added. A blood sample can be of any volume, and can be from any subject such as an animal or human. A preferred subject is a human. A blood sample can be any blood sample, recently taken from a subject, taken from storage, or removed from a source external to a subject, such as clothing, upholstery, tools, etc. A blood sample can therefore be an extract obtained, for example, by soaking an article containing blood in a buffer or solution. A blood sample can be unprocessed, processed, or partially processed, for example, a blood sample that has been centrifuged to remove serum, dialyzed, subjected to flow Cytometry, had reagents added to it, etc. A blood sample can be of any volume. For example, a blood sample can be less than five microliters, or more than 5 liters, depending on the application.

A white blood cell is a leukocyte, or a cell of the hematopoietic lineage that is not a reticulocyte or platelet and that can be found in the blood of an animal. Leukocytes can include lymphocytes, such as B lymphocytes or T lymphocytes. Leukocytes can also include phagocytic cells, such as monocytes, macrophages, and granulocytes, including basophils, eosinophils and neutrophils. Leukocytes can also comprise mast cells.

A red blood cell is an erythrocyte.

Neoplastic cells refers to abnormal cells that grow by cellular proliferation more rapidly than normal and can continue to grow after the stimuli that induced the new growth has been withdrawn. Neoplastic cells tend to show partial or complete lack of structural organization and functional coordination with the normal tissue, and may be benign or malignant.

A malignant cell is a cell having the property of locally invasive and destructive growth and metastasis.

A stem cell is an undifferentiated cell that can give rise, through one or more cell division cycles, to at least one differentiated cell type.

A progenitor cell is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An etiological agent refers to any etiological agent, such as a bacteria, virus, parasite or prion that can infect a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

Subject refers to any organism, such as an animal or a human. An animal can include any animal, such as a feral animal, a companion animal such as a dog or cat, an agricultural animal such as a pig or a cow, or a pleasure animal such as a horse.

A chamber is a structure that comprises a chip and that is capable of containing a fluid sample.

A port is an opening in the housing of a chamber through which a fluid sample can enter or exit the chamber. A port can be of any dimensions, but preferably is of a shape and size that allows a sample to be dispensed into a chamber by means of a pipette, syringe, or conduit, or other means of dispensing a sample.

A conduit is a means for fluid to be transported from a container to a chamber of the present invention. Preferably, a conduit engages a port in the housing of a chamber. A conduit can comprise any material that permits the passage of a fluid through it. Preferably, a conduit is tubing, such as, for example, rubber, Teflon, or tygon tubing. A conduit can be of any dimensions, but preferably ranges from 10 microns to 5 millimeters in internal diameter.

A chip is a solid substrate on which one or more processes such as physical, chemical, biochemical, biological or biophysical processes can be carried out. Such processes can be assays, including biochemical, cellular, and chemical assays; separations, including separations mediated by electrical, magnetic, physical, and chemical (including biochemical) forces or interactions; chemical reactions, enzymatic reactions, and binding interactions, including captures.

An electromagentic chip is a chip that includes at least one electromagnetic unit, such as a micro-electromagnetic unit. The electromagnetic unit can be on the surface of a chip, or can be provided integrally or at least partially integrally, within said chip. For example, an electromagnetic unit can be provided on the surface of a chip or can be imbedded within a chip. Optionally, an electromagnetic unit can be partially imbedded within a chip.

Separation is a process in which one or more components of a sample is spatially separated from one or more other components of a sample. For example, a separation can be performed such that one or more moieties or moieties of interest are translocated to one or more areas of a separation apparatus such as a chip and optionally at least some of the remaining components are translocated away from the area or areas where the one or more moieties of interest are translocated to and/or retained in. Alternatively, a separation can be performed in which one or more moieties are retained in one or more areas and optionally at least some or the remaining components are removed from the area or areas. Alternatively, one or more components of a sample can be translocated to and/or retained in one or more areas and optionally one or more moieties can be removed from the area or areas and optionally collected. It is also possible to cause one or more moieties to be translocated to one or more areas and one or more moieties of interest or one or more components of a sample to optionally be translocated to one or more other areas. Separations can be achieved using physical, chemical, electrical, or magnetic forces. Examples of forces that can be used in separations are gravity, mass flow, dielectric forces, and electromagnetic forces.

Capture is a type of separation in which one or more moieties or moieties of interest is retained in one or more areas of a chip. A capture can be performed using a specific binding member that binds a moiety of interest with high affinity. The specific binding member can be reversibly or irreversibly bound to a solid support, or a portion of a solid support, such as a portion of a chip.

An assay is a test performed on a sample or a component of a sample. An assay can test for the presence of a component, the amount or concentration of a component, the composition of a component, the activity of a component and the like. Assays that can be performed in conjunction with the compositions and methods of the present invention include biochemical assays, binding assays, cellular assays, and genetic assays.

A reaction is a chemical or biochemical process that changes the chemical or biochemical composition of one or more molecules or compounds or that changes the interaction of one or more molecules with one or more other molecules or compounds. Reactions of the present invention can be catalyzed by enzymes, and can include degradation reactions, synthetic reactions, modifying reactions or binding reactions.

A binding assay is an assay that tests for the presence or concentration of an entity by detecting binding of the entity to a specific binding member, or that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A biochemical assay is an assay that tests for the presence, concentration, or activity of one or more components of a sample.

A cellular assay is an assay that tests for a cellular process, such as, but not limited to, a metabolic activity, a catabolic activity, an ion channel activity, an intracellular signaling activity, a receptor-linked signaling activity, a transcriptional activity, a translational activity, or a secretory activity.

A genetic assay is an assay that tests for the presence or sequence of a genetic element, where a genetic element can be any segment of a DNA or RNA molecule, including, but not limited to, a gene, a repetitive element, a transposable element, a regulatory element, a telomere, a centromere, or DNA or RNA of unknown function. As nonlimiting examples, genetic assays can use nucleic acid hybridization techniques, can comprise nucleic acid sequencing reactions, or can use one or more polymerases, as, for example a genetic assay based on PCR. A genetic assay can use one or more detectable labels, such as, but not limited to, fluorochromes, radioisotopes, or signal generating systems.

An electrode is a structure of highly electrically conductive material. A highly conductive material is a material with a conductivity greater than that of surrounding structures or materials. Suitable highly electrically conductive materials include metals, such as gold, chromium, platinum, aluminum, and the like, and can also include nonmetals, such as carbon and conductive polymers. An electrode can be any shape, such as rectangular, circular, castellated, etc. Electrodes can also comprise doped semi-conductors, where a semi-conducting material is mixed with small amounts of other conductive materials. Electrodes can include means for conducting an electric current, such as for conducting an electric current about a core.

A cavity is a structure in a chip, with a lower surface surrounded on at least two sides by one or more walls that extend from the lower surface of the cavity. The walls can extend upward from the lower surface of a cavity at any angle or in any way. The walls can be of an irregular conformation, that is, they may extend upward in a sigmoidal or otherwise curved or multi-angled fashion. The lower surface of the cavity can be at the same level as the upper surface of a chip or higher than the upper surface of a chip, or lower than the upper surface of a chip, such that the cavity is a depression in the surface of a chip. The sides or walls of a cavity can comprise materials other than those that make up the lower surface of a chip. In this way, the lower surface of a chip can comprise a thin material through which electrical forces, including electromagnetic, can be transmitted, and the walls of one or more cavities can optionally comprise other insulating materials that can prevent the transmission of electrical forces. The walls of a cavity of a chip can comprise any suitable material, including silicon, glass, rubber, and/or one or more polymers, plastics, ceramics, or metals.

Continuous flow means that fluid is pumped or injected, including by gravity driven flow, into a chamber of the present invention continuously during the separation process. This allows for components of a sample that are not selectively retained on a chip to be flushed out of the chamber during the separation process.

Binding partner refers to any substances that bind to moieties or moieties of interest with desired affinity or specificity. Non-limiting examples of the binding partners include moieties such as nucleic acid molecules, proteins, antibodies, receptors cells, cellular organelles, viruses, microparticles or an aggregate or complex thereof, or an aggregate or complex of molecules.

A particle or microparticle is a structure of any shape and of any composition, that is manipulatable by a magnetic field. Particles useful in the present invention can have a dimension from about 0.01 micron to about one centimeter. Preferably, the microparticles used in the present invention have a dimension from about 0.1 micron to about several thousand microns. Such particles can be comprised of any suitable material that includes a material in a suitable amount to be manipulatable by a magnetic field, such as on an electromagnetic chip. Particles can include at least in part glass or ceramics, one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Materials that allow particles to be manipulatable by a magnetic field include magnetic material or magnetizable material such as iron, magnetite, ferromagnetic material or ferrimagnetic material.

"Coupled" means bound by any appropriate methods. For example, a moiety can be coupled to a microparticle by specific or nonspecific binding. As disclosed herein, the binding can be covalent or noncovalent, reversible or irreversible.

A specific binding member is one of two different molecules having an area on the surface or in a cavity which specifically binds to and is thereby defined as complementary with a particular spatial and polar organization of the other molecule. A specific binding member can be a member of an immunological pair such as antigen-antibody, can be biotin-avidin or biotin streptavidin, ligand-receptor, nucleic acid duplexes, IgG-protein A, DNA—DNA, DNA—RNA, RNA—RNA, and the like.

A nucleic acid molecule is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof.

A detectable label is a compound or molecule that can be detected, or that can generate a readout, such as fluorescence, radioactivity, color, chemiluminescence or other readouts known in the art or later developed. The readouts can be based on fluorescence, such as by fluorescent labels, such as but not limited to, Cy-3, Cy-5, phycoerythrin, phycocyanin, allophycocyanin, FITC, rhodamine, or lanthanides; and by fluorescent proteins such as, but not limited to, green fluorescent protein (GFP). The readout can be based on enzymatic activity, such as, but not limited to, the activity of beta-galactosidase, beta-lactamase, horseradish peroxidase, alkaline phosphatase, or luciferase. The readout can be based on radioisotopes (such as $^{33}P$, $^{3}H$, $^{14}C$, $^{35}S$, $^{125}I$, $^{32}P$ or $^{131}I$). A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

A signal producing system may have one or more components, at least one component usually being a labeled binding member. The signal producing system includes all of the reagents required to produce or enhance a measurable signal including signal producing means capable of interacting with a label to produce a signal. The signal producing system provides a signal detectable by external means, often by measurement of a change in the wavelength of light absorption or emission. A signal producing system can include a chromophoric substrate and enzyme, where chromophoric substrates are enzymatically converted to dyes that absorb light in the ultraviolet or visible region, phosphors or fluorescers. However, a signal producing system can also provide a detectable signal that can be based on radioactivity or other detectable signals.

The signal producing system can include at least one catalyst, usually at least one enzyme, can include at least one substrate, may include two or more catalysts and a plurality of substrates, and may include a combination of enzymes, where the substrate of one enzyme is the product of the other enzyme. The operation of the signal producing system is to produce a product that provides a detectable signal at the predetermined site, related to the presence of label at the predetermined site.

In order to have a detectable signal, it may be desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes that can produce a multiplicity of signal generating molecules from a single label. An enzyme or coenzyme can be employed which provides the desired amplification by producing a product, which absorbs light, for example, a dye, or emits light upon irradiation, for example, a fluorescers. Alternatively, the catalytic reaction can lead to direct light emission, for example, chemiluminescence. A large number of enzymes and coenzymes for providing such products are indicated in U.S. Pat. No. 4,275,149 and U.S. Pat. No. 4,318,980, which disclosures are incorporated herein by reference. A wide variety of non-enzymatic catalysts that may be employed are found in U.S. Pat. No. 4,160,645, issued Jul. 10, 1979, the appropriate portions of which are incorporated herein by reference.

The product of the enzyme reaction will usually be a dye or fluorescers. A large number of illustrative fluorescers are indicated in U.S. Pat. No. 4,275,149, which disclosure is incorporated herein by reference.

Other technical terms used herein have their ordinary meaning in the art that they are used, as exemplified by a variety of technical dictionaries.

I. AN ELECTROMAGNETIC CHIP HAVING MICRO-ELECTROMAGNETIC UNITS

This aspect of the present invention provides an electromagnetic chip with individually addressable micro-magnetic units that includes: a substrate; a plurality of micro-electromagnetic units on or within said substrate; and means for selectively applying an electric current to one or more of said plurality of micro-electromagnetic units to produce a magnetic filed therein. Preferably, substantially all of said micro-electromagnetic units structured to produce a magnetic field upon application of an electric field thereto and the micro-electromagnetic units are independently in a substantially vertical configuration or a substantially horizontal configuration.

Substrate

The substrate can be of any appropriate material or combination of materials for the manufacture of chips, such as through microfabrication methods used in the semiconductor industry. Preferred materials include, but are not limited to silicon, glass, glasses, sintered glass, quartz, silicon-oxide, plastics, ceramics or the like. The substrate is preferably non-porous, but porous materials are also useful, particularly for applications that utilize the transfer of materials through a substrate to take part in methods of the present invention, such as but not limited to binding reactions, lysing of cells or detection of binding reactions.

The substrate is preferably of dimensions that are appropriate for microfabrication methods, such as etching, sputtering, masking and the like. The substrate is also preferably of a size appropriate for micromanipulation of particles and moieties such as described in the methods herein. For example, the substrate is preferably thin, such as less than about a millimeter in thickness, and between about 5 millimeters and about 10 centimeters in length and width, preferably between about 1 centimeter and about 5 centimeters in length and width. However, such sizes are not considered limiting to the present invention. The substrate can be of any appropriate shape, such as geometric or non-geometric shapes, such as square, circular, oblong, elliptical or the like. Preferred shapes include squares, circles, and appropriate polygons.

The substrate can be part of a single layer or multi-layered chip that can have a plurality of functions. For example, a single layer chip can include a variety of structures to perform a variety of functions, such as vibrational structures such as piezoelectric crystals as they are known in the art to cause currents in a sample or dielectric structures as they are known in the art to move moieties or particles based on their dielectric properties. Alternatively, these additional structures, such as vibrational structures or dielectric structures, can be provided in separate layers of substrate. In this aspect of the present invention, a plurality of substrates can be sandwiched and adhered together and fabricated into a multi-functional chip. The different functional elements can be independently controlled by appropriate controlling devices, such as switches and conductive materials.

The substrate is preferably provided as part of a chamber which can hold samples, such as fluids. The chamber forms walls around at least a portion of the substrate such that fluid can be stored. Optionally, the chamber can be sealed on all sides, but that need not be the case. In addition, a chamber can be connected to a variety of structures such as ports or conduits to allow fluids or solids such as samples or reagents to enter the chamber, such as through conduits. The fluids or solids are introduced into the chamber by appropriate methods or forces, such as by gravity feed or pumps. The chamber can also include exit structures, such as conduits or ports that allow materials within the chamber to be removed. In one preferred aspect of the present invention, the chamber is a flow through chamber that allows materials to be introduced by way of entry structures such as ports or conduits and materials to be removed by way of exit structures such as ports or conduits.

Micro-electromagnetic Unit

An electromagnetic chip of the present invention includes micro-electromagnetic units. These micro electromagnetic units preferably include: a core on or within said substrate and means for conducting an electric current about said magnetic core. Preferably, the core is a magnetic core or a magnetizable core.

Size of Micro-Electromagnetic Units

The micro-electromagnetic units are preferably microfabricated as described in the Examples. The size of the micro-electromagnetic units depends on the orientation of the micro-electromagnetic unit and the strength of the field generated. Preferably, the micro-electromagnetic units have dimension of width and length ranging between about 0.1 micrometer and about 1 centimeter, more preferably between about 10 micrometers and about 1 millimeter. In addition, the size and shape of the micro-electromagnetic units can be selected such that the magnetic field generated thereby is localized or diffuse. Preferably, and contrary to electromagnetic units used to record information on storage media such as magnetic storage media, such as magnetic tapes or disks, the micro-electromagnetic units of the present invention produce a relatively diffuse field having a relatively long working range, particularly for the purposes set forth herein.

Location and Orientation of Micro-Electromagnetic Units

The micro-electromagnetic units are localized in any appropriate configuration based on the desired fields to be produced thereby and the intended use of the chip. The micro-electromagnetic units can be provided on the surface of the substrate, partially imbedded within the substrate or provided imbedded within the substrate. Optionally, an additional layer of material can be provided on top of the substrate in order to protect the micro-electromagnetic units or to provide structures that allow for the immobilization of materials, such as moieties.

The micro-electromagnetic units can be provided individually in any appropriate orientation, such as vertical, substantially vertical, horizontal or substantially horizontal. Such structures can be made using the methods described herein.

The Core

The core of the micro-electromagnetic units can be made of any appropriate material, such as magnetic material or magnetizable material. Preferably, the core includes magnetic or magnetizable materials, such as a ferromagnetic material or a ferrimagnetic material. The core can be made using appropriate methods, such as those described herein.

Means for Conducting an Electric Current

The core is preferably includes means for conducting an electric current about the core. The means preferably includes single or multiple loops of electric conductive traces around said core. The loops of electric conductive traces can be of any appropriate configuration, but are preferably of a circular, a square, an elliptical, a triangular, a spiral or a squared-spiral shape. The loops can be made using any appropriate method, such as those known in the art or described herein. When an electric current is applied to the means for conducting an electric current about the core, a magnetic field is generated by way of electromagnetic phenomenon.

Generated Field

The characteristics of the magnetic field generated by the energized micro-electromagnetic units is determined by a variety of factors, such as the dimensions (length, width and height) of the core, the aspect ratio of the length v. cross section of the core, the magnetic permeability of the core, the magentizabiligy of the core, the orientation of the core, the shape of the core, and the characteristics of the applied electric current. In the present invention, it is desirable that the magnetic field be relatively disperse rather than highly focused. This is contrary to electromagnetic units used in other fields, such as those used to record information on storage media such as magnetic tapes. For example, magnetic heads described in U.S. Pat. No. 5,833,760 to Yamade et al., issued Mar. 16, 1999 (the 760 patent), describes a magnetic head that includes a loop of core material that is configured such that the ends of the loop are in close proximity. This particular configuration results in a strong magnetic field generated in the particular and small locus where the ends of the loop are close together rather than being dispersed round the core or that locus. In contrast, the electromagnetic units of the present invention do not have such structures and the electromagnetic units of the present invention are intended to produce a relatively diffuse magnetic field. This relatively diffuse magnetic field is desirable to moieties and magnetic particles distributed in a relatively large area or volume to a dispersed magnetic field.

Individually Addressable and Modulation

The electromagnetic chip of the present invention preferably includes means for modulating a magnitude and a polarity of the electric current selectively applied to any one of the micro-electromagnetic units. The means for selectively applying preferably includes conductive connections between a micro-electromagnetic unit and a source of electric current and switch means for alternately interrupting and establishing a flow of electric current through the conductive connections. The switch means can be any appropriate means, such as, but not limited to mechanical switching means, electronic switching means or a combination thereof.

Individual micro-electromagnetic units may be selectively addressable so that at any point in time, there may be only a single energized unit generating a local magnetic field or there may be multiple energized units generating more or less complex magnetic fields. Addressing a micro-electromagnetic unit means applying electric current to energize the unit and to generate magnetic field in its vicinity. Electric current amplitudes and directions are selected so that energized units produce fields of sufficient intensity to attract and move particles such as magnetic particles or magnetically modified molecules. Units that are not selectively energized may be completely off (for example, zero magnetic field) or such units may produce magnetic fields of insufficient intensity to attract or otherwise move the magnetic particles.

Selective addressing of individual units can be achieved in a number of ways. For example, where each unit contains a single loop of electric conductor one end of the loop can be connected to an electric current source (through electrical switching means) while the other end of the loops is attached to an electric current sink so that a current will flow through the loop. In another example, as explained below, units in a column/row array can be selectively activated by attach (through switching means) a row to, for example, a current source and a column (through switching means) to a current sink. This will energize the unit at the intersection of the column and row.

The micro-electromagnetic units are preferably individually addressable, but that need not be the case. The individual micro-electromagnetic units can be connected by an appropriate circuitry or configuration, such as being wired in series or in parallel. Having the micro-electromagnetic units individually addressable allows a greater degree of flexibility in the operation of a particular chip. For example, should a particular micro-electromagnetic unit be defective, then having these units in series would tend to increase the defect rate of chip manufacture because one defect in the chain would lead to poor performance or inoperability of the chip, much like a single defective bulb in a chain of holiday lights. Having the units in parallel would tend to overcome this problem, but would tend not to allow the individual units to be activated individually and independently, such as spatially or temporally or with differing amounts or types of current.

In one aspect of the present invention, the traveling magnetic wave, such as used in traveling wave magnetoelectrophoresis, it is important to have the units individually addressable. For example, a group of horizontally oriented units can be fabricated such that the line-up parallel to each other. The units can be individually addressable such that current can be applied to the units at different times, preferably neighbor to neighbor, such that the magnetic field travels spatially along the line of units, much like a wave, such as by analogy in traveling wave dielectrophoresis. In traveling wave magnetoelectrophoresis, the traveling magnetic wave can be, for example made with DC current to make synchronized waves or with AC current to make continuous waves. This traveling wave would allow particles to be moved along the wave in a direction and manner determined by the operator or fabricator based on the intended purpose of the chip. These structures and methods can be used to manipulate magnetic particles using traveling magnetic waves rather than manipulating particles based on their dielectric properties using traveling wave dielectrophoresis, including particle switching, as described in U.S. patent application Ser. No. 09/678,263 entitled "Apparatus for Switching and Manipulating Particles and Method of Use Thereof" naming Xiaobo Wang, Weiping Yang, JunQuan Xu, Jing Cheng and Lei Wu as inventors, filed Oct. 3, 2000. The particular electronic configurations can be made using methods known in the art and described herein.

For synchronized waves using DC currents, the units can be addressed sequentially with such current such that the magnetic fields generated by the electromagnetic units are sequentially energized and deenergized. The deenergization process can lead to degaussing, meaning it takes a certain amount of time for the current to decay, such as sinusoidal decay. Preferred energizing values are between about 0.1 mA to about 3 A, preferably between about 1 mA and about 300 mA, and more preferably between about 10 mA and about 30 mA.

For continuous waves using AC currents, the units can be addressed using currents of different phases, such as phases that differ by 90 degrees for four units (360/4=90). Preferred currents are between about 0.001 Hz and about 1 GHz, more preferably between about 0.01 Hz and about 100 MHz or between about 0.1 Hz and about 10 MHz, more preferably between about 0.1 Hz and about 1 MHz or between about 1 Hz and about 100 KHz, and more preferably between about 10 Hz and about 10 KHz.

Arrays and Sizes

The electromagnetic chip of the present invention preferably includes micro-electromagnetic units that are arranged on or within the substrate in a substantially regular, repetitive pattern with substantially equal distances between neighboring units.

The individual micro-electromagnetic units in a single chip may be of a single shape and dimension or there may be a variety of unit shapes and sizes within one chip. Characteristic dimensions of a unit vary from less than one micrometer to as large as one centimeter. The characteristic dimension refers to, for example, a diameter for a circle loop unit and a side width for a square loop unit. It will be apparent to one of ordinary skill in the art that where it is desired to react a large number of ligand molecules a large unit size can be used. The units may be arranged in a regular, repetitive pattern (for example, a rectangular grid) or they may be arranged in an irregular or random pattern.

Functional Layer

The electromagnetic chip of the present invention can optionally include at least one functional layer; wherein said functional layer can immobilize at least one moiety or ligand. Preferred immobilized moieties include nucleic acid molecules, antibodies or receptors. The functional layer, when present, can be provided on the surface of the substrate such as to protect or shield the micro-electromagnetic units or to provide a variety of chemical groups that can be utilized in the methods of the present invention.

The functional layer can be of any appropriate material, but is preferably includes at least one of the following materials: a hydrophilic molecular monolayer, a hydrophilic molecular monolayer with functional groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups.

The functional layer can be a sheet of material that is contacted, attached or adhered to the substrate. In the alternative, the functional layer can be made by modifying, such as by chemical modification, of the substrate. Furthermore, the functional layer can be made by spraying, dipping or otherwise contacting liquid or semisolid material onto the substrate, wherein the material is then solidified such as through cooling, gelling, solidifying or polymerization.

The functional layer can have available and presented thereon a variety of functional groups that can take part in a variety of chemical reactions designed to immobilize moieties thereon. Preferred functional groups include but are not limited to aldehydes, carbodiimides, succinimydyl esters, antibodies, receptors and lectins. Materials having these functional groups are known in the art. In addition, methods of making a variety of surfaces having these functional groups are known in the art.

The functional layer can include a moiety or ligand immobilized thereon. Preferred immobilized moieties or ligands include, but are not limited to nucleic acid molecules (such as single stranded or double stranded DNA or RNA or a combination thereof), binding reagents (such as antibodies or active fragments thereof), receptors or other members of binding pair, polypeptides, proteins, carbohydrates, lipids, prokaryotic cells, eukaryotic cells, prions, viruses, parasites, bacteria antibodies, lectins or receptors. Functional layers having such immobilized moieties thereon can be made using a variety of methods. For example, a functional layer with an appropriate functional group can be contacted with a preparation having a moiety to be immobilized thereon. The immobilization of such moieties on a functional layer can be throughout the functional layer or localized using appropriate methods, such as masking.

Manufacture of Micro-Electromagnetic Units

Micro-electromagnetic units are fabricated on substrate materials and generate individual magnetic fields when electric currents are applied. One example of the unit is a single loop of electrical conductor wrapped around a ferromagnetic body or core and connected to an electric current source through electronic switches. Such a loop may be a circle, ellipse, spiral, square, triangle or other shapes so long as a flow of electric current can be facilitated around the ferromagnetic body. If the loop is single, it should be complete or nearly complete. The loop may be in the form of a plurality of turns around the ferromagnetic body. The turns may be fabricated within a single layer of the microstructure, or, alternatively, each turn may represent a separate layer of the structure. The electric conductor may be a deposited conductive trace as in a electroplated, sputtered or deposited metallic structure, or the conductor can be formed within a semiconductor layer through selective doping. A preferred arrangement of array of a plurality of micro-electromagnetic units has a column and row structure of the form common in microelectronics. That is, the columns and rows are mutually perpendicular although the columns and rows can readily be offset at different angles (for example 80 degrees).

Chambers

A chamber of the present invention is a structure that can contain a fluid sample. A chamber can be of any size or dimensions, and preferably can contain a fluid sample of between one nanoliter and 50 milliliters, more preferably between about 1 microliter and about 10 milliliters, and most preferably between about 10 microliters and about 1 milliliter. Preferably, a chamber comprises a chip. A chamber can comprise any suitable material, for example, silicon, glass, metal, ceramics, polymers, plastics, etc. and can be of a rigid or flexible material. Preferred materials for a chamber include materials that do not interfere with dielectrophoresis of moieties in a sample, for example, insulating materials that do not bind charged or polarized molecules, such as certain plastics and polymers, for example, acrylic, or glass.

Chambers used in the methods of the present invention can comprise chips, where chips are solid supports on which one or more separations, assays, or capturing procedures can be performed. A chip can comprise one or more metals, ceramics, polymers, copolymers, plastics, rubber, silicon, or glass. A chip can comprise one or more flexible materials. A chip can be from about one $mm^2$ to about 0.25 $m^2$. Preferably, the size of the chips useable in the present methods is from about four $mm^2$ to about 25 $cm^2$. The shape of the chips useable in the present methods can be regular shapes such as square, rectangular, circular, or oval, or can be irregularly shaped. Chips useable in the methods of the present invention can have one or more wells or one or more channels that can be etched into a chip or built onto the surface of a chip.

Preferably, in embodiments where the chamber comprises electrodes, the electrodes will be incorporated onto or within the chip, but this is not a requirement of the present invention. Electrodes on a chip can be of any shape, such as rectangular, castellated, triangular, circular, and the like. Electrodes can be arranged in various patterns, for example, spiral, parallel, interdigitated, polynomial, etc. Electrode arrays can be fabricated on a chip by methods known in the art, for example, electroplating, sputtering, photolithography or etching. Examples of a chip comprising electrodes include, but are not limited to, the dielectrophoresis electrode array on a glass substrate (for example, Dielectrophoretic Manipulation of Particles by Wang et al., in IEEE Transaction on Industry Applications, Vol. 33, No. 3, May/June, 1997, pages 660–669), individually addressable electrode array on a microfabricated bioelectronic chip (e.g., Preparation and Hybridization Analysis of DNA/RNA from E. coli on Microfabricated Bioelectronic Chips by Cheng et al., Nature Biotechnology, Vol. 16, 1998, pages 541–546), and the capillary electrophoresis chip (for example, Combination of Sample-Preconcentration and Capillary Electrophoresis On-Chip by Lichtenberg, et al., in Micro Total Analysis Systems 2000 edited by A. van den Berg et al., pages 307–310).

A chamber that comprises a chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, for example, tygon or Teflon tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a solution of the present invention that selectively modifies the dielectric properties of one or more moieties in a sample, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

II. AN ELECTROMAGNETIC CHIP HAVING CAVITIES

The present invention also includes an electromagnetic chip having an array of individually addressable micro-electromagnetic units, including: a substrate; an plurality of cavities arranged in an array on or within said substrate; a first layer of conductive traces, wherein each separate trace of said first layer of conductive traces runs adjacent to one of said columns; a second layer of conductive traces insulated from aid first layer of conductive traces, wherein each of said second layer of conductive traces are perpendicular to said first layer of conductive traces runs adjacent to one of said rows. Preferably, said cavities are arranged in columns and rows and each cavity optionally contains a magnetizable core, wherein said magnetizable cores are independently in a substantially vertical configuration or a substantially horizontal configuration;

In one aspect of the present invention, a first layer of insulating material separates said first layer of conductive traces from said second layer of conductive traces. The first layer of insulating material can be any material appropriate for the manufacture of electromagnetic chips of the present invention, such as, but not limited to silicon dioxide, silicon nitride, plastic, glass, ceramic, photoresist and rubber.

Preferably, a second layer of insulating material is deposited on a top surface of said second layer of conductive traces and on a top surface of said magnetizable cores. The second insulating layer can be any appropriate material for the manufacture of electromagnetic chips of the present invention, and can be the same or different form the first layer of insulating material Preferred materials include, but are not limited to silicon dioxide, silicon nitride, plastic, glass, ceramic, photoresist and rubber.

An electromagnetic chip of the present invention can also optionally include an additional layer of conductive traces, each of said set of conductive traces running adjacent to one of said columns and/or rows and insulated from other layers of conductive traces. Conductive traces for electromagnetic chips of the present invention can be of any appropriate materials for the manufacture and use of these chips. Preferred materials include, but are not limited to, aluminum, gold, silver, tin, copper, platinum, palladium, carbon and semiconductor materials.

The electromagnetic chip of the present invention can optionally further include a functional layer. This functional layer can be of any appropriate material, but is preferably selected from the group consisting of a hydrophilic molecular monolayer, a hydrophilic molecular monolayer with foundational groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups. Preferred functional groups include of aldehydes, carbodiimides, succinimydyl esters, antibodies, receptors and lectins.

Electromagnetic chips of the present invention also optionally include at least one functional layer and optionally at least one fluidic chamber. The fluidic chamber acts to bringing liquids into contact with the array. Such fluidic chambers can be fitted with appropriate materials, such as portals or conduits, to allow materials, such as reagents, to be introduced into the fluidic chamber and to allow materials to be removed from the chamber. This type of flow-through chamber is particularly well suited for automated applications of the methods discussed herein.

Preferred Electromagnetic Chips

Preferred electromagnetic chips of the present invention are exemplified in the Figures and in the Examples. One preferred electromagnetic chip having an array of individually addressable micro-electromagnetic units (10) having: a substrate (16); an array of cavities (22) in said substrate (16); and a first layer of conductive traces (30'), each of said first layer of conductive traces extending at least 90 degrees around at least one of the ferromagnetic cores. Preferably, the cavities are arranged in columns and rows, each of said cavities optionally containing a ferromagnetic core (26).

In this preferred aspect of the present invention, the electromagnetic chip optionally further comprising an additional layer of conductive traces, each set of additional conductive traces extending at least 90 degrees around at least one of the ferromagnetic cores and being separated from the first set of conductive traces by an insulating layer penetrated by a vertical conductive connection between traces of the first layer and traces of the additional layer. Preferably, a first layer of insulating material separates the first layer of conductive traces from said additional layer of conductive traces. The material of said first insulating layer preferably includes a material selected from the group consisting of silicon dioxide, silicon nitride, plastic, glass, ceramic, photoresist and rubber. The conductive traces preferably include a material selected from the group consisting of aluminum, gold, silver, tin, copper, platinum, palladium, carbon and semiconductor materials.

The electromagnetic chip of the present invention optionally includes a second layer of insulating material that is deposited on a top surface of said array. The material of said second insulating layer is selected from the group consisting of silicon dioxide, silicon nitride, plastic, glass, ceramic, photoresist and rubber.

The electromagnetic chip of the present invention preferably includes a functional layer for binding ligands. The functional layer is preferably a hydrophilic molecular monolayer, a hydrophilic molecular monolayer with foundational groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material, a non-porous material with functional groups or a combination thereof. The functional groups are preferably selected from the group consisting of aldehydes, carbodiimides, succinimydyl esters, antibodies, receptors and lectins.

Electromagnetic chips of the present invention also optionally include at least one fluidic chamber for bringing liquids into contact with said array. Such fluidic chambers can be fitted with appropriate materials, such as portals or conduits, to allow materials, such as reagents, to be introduced into the fluidic chamber and to allow materials to be removed from the chamber. This type of flow-through chamber is particularly well suited for automated applications of the methods discussed herein.

III. METHOD FOR DETECTING REACTIONS

The present invention also includes a method for directing reactions between a ligand and a target molecule. This method includes the steps of:

1) providing an article of manufacture having a plurality of individually addressable micro-electromagnetic units, such as an electromagnetic chip of the present invention;
2) forming a functional layer above the micro-electromagnetic units, wherein the functional layer optionally directly contacts the micro-electromagnetic units;
3) modifying the ligand molecules to make modified ligand molecules that are positional by a magnetic field;
4) contacting a solution comprising the modified ligand molecules with the functional layer;
5) creating a pattern of immobilized ligand molecules by selectively energizing at least one of the micro-electromagnetic units to form at least one magnetic field which can position the ligand molecules at optionally predetermined locations where at least a portion of the ligand molecules become immobilized on the functional layer;
6) modifying said target molecules to make the target molecules positional by magnetic fields;
7) disposing a solution containing the modified target molecules on the pattern of immobilized ligand molecules; and
8) selectively energizing the micro-electromagnetic units to form magnetic fields which position the modified target molecules in juxtaposition to optionally predetermined immobilized ligand molecules allowing a reaction between optionally predetermined target molecules and optionally predetermined ligand molecules.

Chips

The preferred electromagnetic chip for use in this method is an electromagnetic chip of the present invention. However, other appropriate electromagnetic chips can also be utilized.

Magnetic Particles

Magnetic particles or materials used with the present invention may be of different sizes ranging from nanometer dimensions to micrometer or even millimeter dimensions. Magnetic particles may be of a variety of materials and be manufactured by a number of different processes as long as the magnetic fields produced by the biochips of the present invention can induce a sufficient magnetic dipole-moment in the particles.

Magnetic particles that are capable of being translocated in response to electromagnetic forces can comprise any magnetic material. Paramagnetic particles are preferred whose dipoles are induced by externally applied magnetic fields and return to zero when the external field is turned off. Suitable paramagnetic materials include, for example, iron compounds. Surfaces of magnetic particles of the present embodiment can optionally be coated with one or more compounds to facilitate attachment of specific binding members or direct or indirect binding of moieties of interest. Magnetic particles of the present invention can be of any shape. Preferably, magnetic particles are spherical or ellipsoid, but this is not a requirement of the present invention.

More than one preparation of magnetic particles can be used in the methods of the present invention. In embodiments using more than one preparation of magnetic particles, different magnetic particles can have different surface properties, such that they can bind different moieties in a sample. In this way, more that one type of moiety can be separated using the methods of the present invention. Different surface properties of magnetic particles can be conferred, for example, by coating the magnetic particles with different compounds, or by reversibly or irreversibly linking different specific binding members to the surfaces of the magnetic particles.

The moiety to be manipulated can be coupled to the surface of the particle with any methods known in the art. For example, the moiety can be coupled to the surface of the binding partner directly or via a linker, preferably, a cleavable linker. The moiety can also be coupled to the surface of the particle via a covalent or a non-covalent linkage. Additionally, the moiety can be coupled to the surface of the particle via a specific or a non-specific binding. Preferably, the linkage between the moiety and the surface of the particle is a cleavable linkage, for example, a linkage that is cleavable by a chemical, physical or an enzymatic treatment.

Linkers can be any moiety suitable to associate the moiety and the binding partner. Such linkers and linkages include, but are not limited to, amino acid or peptidic linkages, disulfide bonds, thioether bonds, hindered disulfide bonds, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol*, 30:379–386 ((1993)). In some embodiments, several linkers may be included in order to take advantage of desired properties of each linker. Other linkers, include trityl linkers, particularly, derivatized trityl groups to generate a genus of conjugates that provide for release of the moiety at various degrees of acidity or alkalinity (U.S. Pat. No. 5,612,474). Additional linking moieties are described, for example, in Huston et al., *Proc. Natl. Acad. Sci. U.S.A.*, 85:5879–5883 (1988), Whitlow, et al., *Protein Engineering*, 6:989–995 (1993), Newton et al., *Biochemistry*, 35:545–553 (1996), Cumber et al., *Bioconj. Chem.*, 3:397–401 (1992), Ladurner et al., *J. Mol. Biol.*, 273:330–337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a moiety to a microparticle and methods of coupling linkers to microparticles are further described in U.S. patent application Ser. No. 09/636,104, filed Aug. 10, 2000, entitled Methods for Manipulating Moieties in Microfluidic Systems which is incorporated herein by reference in its entirety.

In some cases, after manipulating the moiety-particle, for example, molecule-microparticle, complexes to desired locations, microparticles do not interfere with reactions the molecules are involved. Thus, it may not be necessary to decouple molecules from microparticle surfaces. However, in other cases, it may be desirable or necessary after the manipulating step. The nature of the decoupling step depends on the nature of the moiety, the particle, the surface modification of the particle and the manipulation step. Generally, the condition of the decoupling step is the opposite of the conditions that favor the binding between the moiety and the particle. For example, if a moiety binds to the particle at a high salt concentration, the moiety can be decoupled from the particle at a low salt concentration. Similarly, if a moiety binds to the particle through a specific linkage or a linker, the moiety can be decoupled from the particle by subjecting the linkage to a condition or agent that specifically cleaves the linker.

Paramagnetic particles are preferred whose magnetic dipoles are induced by externally applied magnetic fields and return to zero when external field is turned off. For such applications, commercially available paramagnetic or other magnetic particles may be used. Many of these particles are between below micron (for example, 50 nm 0.5 micron) and tens of microns. They may have different structures and compositions. One type of magnetic particles has ferromagnetic materials encapsulated in thin latex, for example, polystyrene, and shells. Another type of magnetic particles has ferromagnetic nanoparticles diffused in and mixed with latex for example, polystyrene, and surroundings. The surfaces of both these particle types are polystyrene in nature and may be modified to link to various types of molecules.

A preparation that includes magnetic microparticles can also include one or more moieties such as specific binding members. Such binding members can comprise one or more proteins such as antibodies, antibody fragments, antigens, ligands (such as, but not limited to receptor ligands), lectins, etc. Binding members can also be organic or inorganic molecules, such as, for example, nickel, glutathione, biotin, avidin, streptavidin, non-protein receptor ligands or ligand analogues, and the like. Binding members can also comprise nucleic acids, whether RNA, DNA, or non-naturally occurring nucleic acids. One or more specific binding members can be reversibly or irreversibly bound to magnetic microparticles. Methods of conjugating molecules, such as nucleic acids and proteins, to solid surfaces are know in the art.

Modifying Ligand Molecules

The ligand molecule can be any moiety, such as but not limited to biological molecules, chemical reagents or pharmaceutical molecules and can be a component of a sample, including a cell. Alternatively, the ligand molecule can include nucleic acid molecules, antibodies and/or antigens.

The ligand molecule can be modified to be positional by a magnetic field by a variety of methods, such as by linking said ligand molecules to a magnetic material. This linking can be accomplished by a variety of methods, such as by utilizing a linker such as is known in the art. The linking can be made using, for example, covalent bonds or biological affinity, such as avidin-biotin affinity, lectin-hapten affinity, receptor-ligand affinity or antibody-antigen reactions. Preferably, the linker is a cleavable linker. The cleavable linker can be any of those known in the art, such as those that are cleavable by light, heat, enzymatic activity or chemical reaction.

During the operation of the method of the present invention the ligand molecule can separated from said magnetic material by cleaving said cleavable linker. Optionally, such as in the case of a fluidic chamber being used in the method, the separated magnetic material is removed by a magnetic field by a fluidic wash.

In one aspect of the present invention, the ligand molecules can be modified by mixing a solution of the ligand molecules with magnetic material, and freezing droplets of ligand molecules with magnetic material to form small solid magnetic particles. In this case, magnetic dispensers can be used to position said small magnetic particles on the electromagnetic chip.

Modifying Target Molecule

The target molecule can be any moiety, such as but not limited to biological molecules, chemical reagents or pharmaceutical molecules and can be a component of a sample, including a cell. The Alternatively, the target molecule can include nucleic acid molecules, antibodies and/or antigens.

The target molecule can be modified to be positional by a magnetic field by a variety of methods, such as by linking the target molecules to a magnetic material. This linking can be accomplished by a variety of methods, such as by utilizing a linker such as is known in the art. The linking can be made using, for example, covalent bonds or biological affinity, such as avidin-biotin affinity, lectin-hapten affinity, receptor-ligand affinity or antibody-antigen reactions. Preferably, the linker is a cleavable linker. The cleavable linker can be any of those known in the art, such as those that are cleavable by light, heat, enzymatic activity, pH, salt or chemical reaction.

During the operation of the method of the present invention the target molecule can separated from said magnetic material by cleaving said cleavable linker. Optionally, such as in the case of a fluidic chamber being used in the method, the separated magnetic material is removed by a magnetic field by a fluidic wash.

In one aspect of the present invention, the target molecules can be modified by mixing a solution of the target molecules with magnetic material, and freezing droplets of target molecules with magnetic material to form small solid magnetic particles. In this case, magnetic dispensers can be used to position said small magnetic particles on the electromagnetic chip.

Binding Reactions

These method of the present invention utilize binding reactions in order to identify moieties such as ligand or targets. In solutions, binding or reactions between molecules (for example, antibody and antigen; specific DNA probe and its complementary single-stranded target DNA) occur as the molecules collide during diffusion. The efficiency and speed of the reactions depend on the local concentration of the reacting molecules and the kinetic energy of their collisions. In many biochip-based systems, one type of molecule is immobilized at the chip surface while another type of molecule is present in a solution on the chip surface. Reactions occur when molecules passively diffusing in the solution collide with the immobilized molecules. Only small percentages of the molecules in the solution diffuse and collide in a reasonable amount of time. Thus, the reactions are slow and inefficient, severely limiting the speed, efficiency and the sensitivity of biochemical assays performed on these biochips. In the electromagnetic biochips of the present invention, the molecules in solution are actively brought into contact with the immobilized molecules on the chip surface by means of magnetic forces. The resulting reactions are actively driven by magnetic force leading to improved speed, efficiency and sensitivity.

For a typical magnetic particle made of superparamagnetic material, when the particle is subjected to a magnetic field B, a magnetic dipole $\mu$ is induced in the particle $$\mu = V_p(\chi_p - \chi_m)$$
$$= V_p(\chi_p - \chi_m)H_m$$

where $V_P$ is the particle volume, $X_p$ and $X_m$ are the volume susceptibility of the particle and its surrounding medium, $\mu_m$ is the magnetic permeability of the medium, $H_m$ is the magnetic field strength. The magnetic force $F_{magnetic}$ acting on the particle is determined by the magnetic dipole moment and the magnetic field gradient:

$$F_{magnetic} = 0.5 \; V_P \; (X_p - X_m) H_m \cdot \Delta B_m;$$

where the symbols "•" and "Δ" refer to dot-product and gradient operations, respectively. Whether there is magnetic force acting on a particle depends on the difference in the volume susceptibility between the particle and its surrounding medium. Typically, particles are suspended in a liquid, nonmagnetic medium (the volume susceptibility is close to zero), thus it is necessary to utilize magnetic particles (their volume susceptibility is much larger than zero). The particle velocity $v_{particle}$ under the balance between magnetic force and viscous drag is given by:

$$v_{particle} = \frac{F_{magnetic}}{6\pi \eta_m}$$

where r is the particle radius and $\eta_m$ is the viscosity of the surrounding medium. Thus to achieve sufficiently large magnetic manipulation force, the following factors should be considered: (1) Particle susceptibility should be maximized; (2) Magnetic field strength should be maximized; and (3) Magnetic field strength gradient should be maximized.

Detecting

The binding of a ligand molecule and a target molecule can be detected by a variety of methods. The use of a detectable label or a detectable system is one such method. Preferably, the detectable label or detectable system has a visual or optically detectable readout such that optics or the aided or unaided eye can be used for detecting binding. To detect such binding or localizing a ligand or target using detectable labels, either one or both of the ligand molecule or the target molecule can be bound with a detectable label or a portion of a detectable system. In the alternative, an additional reagent, such as an labeled specific binding reagent such as a labeled antibody, that binds with the ligand, the target or both can be used. In this instance, such as when a fluidics chamber such as a flow-through fluidics chamber is used, the chamber can be injected with a labeled antibody that binds with its binding partner. The chamber can be washed and the localization of the labeled detected, using appropriate methods and instrumentation for the label used, such as by optical detection using fiber optics and/or CCD instrumentation or by a magnetic readout, such as using a magnetic resonance head (a MR head).

IV. METHOD FOR MANIPULATING MAGENTIC PARTICLES

The present invention also includes a method for manipulating magnetic particles or magnetizable particles. This method includes the steps of: providing an electromagnetic chip comprising a plurality of individually addressable micro-electromagnetic units; placing magnetic particles or magnetizable particles onto an exposed surface on or within said electromagnetic chip; and modulating electric currents applied to one or more of said micro-electromagnetic units so as to change the magnetic field distribution over the surface of said electromagnetic chip, thereby altering magnetic forces acting on said magnetic particles or magentizable particles. The result of this process is that the magnetic particles or magnetizable particles are moved to or from a locus, preferably a defined locus.

The magnetic particles or magentizable particles can include at least one moiety, including components of a sample, such as any cells such as blood cells or malignant cells or neoplastic cells. Other preferred moieties include nucleic acid molecules, specific binding reagents such as antibodies and receptors. Particularly preferred moieties are nucleic acid molecules, DNA, RNA, polypeptides, proteins, carbohydrates, lipids, prokaryotic cells, eukaryotic cells, prions, viruses, parasites, antibodies, lectins, receptors or components of samples including cells such as blood cells, malignant cells or neoplastic cells.

The moiety is preferably linked to the magnetic or magentizable particles. Linking can be by indirectly attaching or directly attaching the moiety to the magnetic particles or magentizable particles. Indirect attachment can be accomplished using a variety of methods, such as via aggregation or the use of specific binding members such as antibodies or receptors. Direct attachment can be accomplished by using a variety of methods such as chemical linkers, linking molecules or direct coupling of the moiety to a magnetic particle or magentizable particle, such as when such particles are activated to include appropriate functional groups such as in the functional layer of the present invention.

Particles having moieties thereon can be moved from or to a loci such as a predetermined loci on a chip based on this method. The particles with moieties can be reversibly immobilized at such loci by the magnetic forces thereon, which allows a chip or a portion thereof to be washed, such as using flow through methods particularly when a chamber is present. Alternatively, the chip can have specific binding members immobilized thereon, such as on a functional layer, where the specific binding members can reversibly or irreversibly bind the moiety or the particle or both. This also allows for a chip or a portion thereof to be washed. Furthermore, functional groups on the chip, such as on a functional layer, can have reactive groups that can irreversibly bind or reversibly bind the moiety, particle or both, which also allows for a chip to a portion thereof the be washed. Thus, these methods allow for the separation of moieties and the localization of moieties. Separation of moieties can include localizing a moiety on one location of a chip, or more complete separation such as through washing.

Once separated, localized and optionally immobilized, either reversibly or irreversibly, a variety of methods can be used to detect moieties at the locus or to further process the moieties. For example, a localized moiety can be detected if the moiety or the particle is detectably labeled with a detectable label or a detectable system. Preferred detectable labels include fluorescent labels, colored labels, labeled secondary reagents or labeled particles. Detectable labels can be attached to the moiety prior to separation or can be added after separation such as through a secondary reagent such as detectably labeled antibody as such methods are known in the art. Alternatively, the particle can have a label, either inherently such as by the color or opaqueness of the particle or by the addition of a label, such as fluorescence or colored moiety. The localization of the label indicates the localization of the particle and/or moiety depending on the particular configuration of the assay. Such detection can be accomplished using visual observation of appropriate instrumentation such as radiation detectors or optical detectors as appropriate for a particular detectable label. Preferred labels are fluorescent labels that are detectable using fiber optic and/or CCD technologies or a MR head can also be used to detect electromagnetic signals such as provided by magnetic particles. Such detection methods can be qualitative, semi-quantitative or quantitative as such methods are known in the art.

Tests for separation of moieties by can use detectable labels, where at least one moiety of a sample is detectably labeled. For example, after mixing a biological sample with a sample solution of the present invention performing a magnetic separation procedure, one cell type can be labeled using antibodies that recognize that cell type and not other cell types or components of the sample. The antibodies can be bound to a detectable label, such as, for example, a fluorescent molecule, such as rhodamine, fluorescein, Texas red, phycoerythrin, phycocynanin, green fluorescent protein, cyan fluorescent protein, blue fluorescent protein, yellow fluorescent protein, D.s. red protein, etc. Another cell type can optionally be labeled with a different antibody and a different detectable label. In this way, the positions of the cells carrying the fluorescent labels can be visualized and the quality of magnetic separation can be assessed. Sample components other than cells, such as, for example organelles, viruses, prions, proteins, complexes, and nucleic acids, can also be detectably labeled with antibodies to test their dielectric separation.

Other tests for separation include binding assays to test for the presence of proteins, nucleic acids, or other compounds after performing separation procedures. For example, after mixing a sample with a sample solution and performing a cell separation procedure, the separation can be assessed by the binding of an antibody specific for a protein expressed by a given cell type, or the binding of a probe nucleic acid to a nucleic acid sequence characteristic of a particular cell type (for example, that of a species of bacteria), etc. The detection of nucleic acid sequences and proteins that are indicative of the presence of a particular cell type or cellular component can also use enzymatic detection procedures (for example, PCR) and assays (for example, cytochrome P450 assays). The dielectric separation of cells can also be monitored by loading cells with detectable labels, such as dyes, as they are known in the art. For example, cells can be loaded with BCECF-AM (available from Molecular Probes, Eugene, Oreg.) a flourescein probe that can be taken up by viable cells and there position after dielectric separation can be determined (Gascoyne et al. IEEE Transcactions 33:670–678 (1997)). A chip on which separation of cells has been tested can be viewed microscopically, or separated moieties can be flushed out of the chamber and examined and quantitated by microscopic examination, flow cytometry, or assays, such as, but not limited to cell growth assays.

Localized moieties can be further processed. For example, the moiety can be separated from the particle using appropriate methods. For example, linkers used to link a moiety to a particle can be cleaved using appropriate methods, such as by chemicals, enzymes, pH, salt or light depending on the characteristics of the linker as is known in the art.

The moiety to be manipulated can be coupled to the surface of the particle with any methods known in the art. For example, the moiety can be coupled to the surface of the particle directly or via a linker, preferably, a cleavable linker. The moiety can also be coupled to the surface of the particle via a covalent or a non-covalent linkage. Additionally, the moiety can be coupled to the surface of the particle via a specific or a non-specific binding. Preferably, the linkage between the moiety and the surface of the particle is a cleavable linkage, for example, a linkage that is cleavable by a chemical, physical or an enzymatic treatment.

Linkers can be any moiety suitable to associate the moiety and the particle. Such linkers and linkages include, but are not limited to, amino acid or peptidic linkages, disulfide bonds, thioether bonds, hindered disulfide bonds, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol.*, 30:379–386 ((1993)). In some embodiments, several linkers may be included in order to take advantage of desired properties of each linker. Other linkers, include trityl linkers, particularly, derivatized trityl groups to generate a genus of conjugates that provide for release of the moiety at various degrees of acidity or alkalinity (U.S. Pat. No. 5,612,474). Additional linking moieties are described, for example, in Huston et al., *Proc. Natl. Acad. Sci. U.S.A.*, 85:5879–5883 (1988), Whitlow, et al., *Protein Engineering*, 6:989–995 (1993), Newton et al., *Biochemistry*, 35:545–553 (1996), Cumber et al., *Bioconj. Chem.*, 3:397–401 (1992), Ladurner et al., *J. Mol. Biol.*, 273:330–337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a moiety to a microparticle and methods of coupling linkers to microparticles are further described in U.S. patent application Ser. No. 09/636,104, filed Aug. 10, 2000, which is incorporated herein by reference in its entirety.

In some cases, after manipulating the moiety-particle, for example., molecule-microparticle, complexes to desired locations, microparticles do not interfere with reactions the molecules are involved. Thus, it may not be necessary to decouple molecules from microparticle surfaces. However, in other cases, it may be desirable or necessary after the manipulating step. The nature of the decoupling step depends on the nature of the moiety, the particle, the surface modification of the partner and the manipulation step. Generally, the condition of the decoupling step is the opposite of the conditions that favor the binding between the moiety and the particle. For example, if a moiety binds to the particle at a high salt concentration, the moiety can be decoupled from the particle at a low salt concentration. Similarly, if a moiety binds to the particle through a specific linkage or a linker, the moiety can be decoupled from the particle by subjecting the linkage to a condition or agent that specifically cleaves the linkage.

Alternatively, when a moiety is a cell, the cell can be modified, such as through lysis or permeabilization as is known in the art. This lysis or permeabilization allows cellular or intracellular moieties to be freed. Preferred intracellular moieties or cellular moieties to be freed include nucleic acid molecules, proteins, peptides, receptors, membrane fragments and organelles. In this way, intracellular moieties of interest can be separated from the remainder of a sample. The intracellular moieties and/or cellular moieties can be collected and further processed. This is particularly true when the chip is a flow-through chip. The intracellular components can then be detected using appropriate methods. For example, PCR and/or hybridization can be used to detect nucleic acid molecules and immunoassays can be used to detect antigens or epitopes.

Different labels can be used to detect different moieties. For example, a Texas Red label can be used to detect one moiety and a fluorescein label can be used to detect a second moiety. The separation of the moieties on a chip can allow for the detection of the different moieties on a single chip or multiple chips. Patterns made on such chips by such labels can be utilized as detection methods as well. For example, a chip can have a variety of loci that can bind a variety of different moieties. Such moieties can include specific binding member such as antibodies, ligands, receptors or nucleic acid molecules that are reversibly or irreversibly immobilized at such loci using, for example, a functional layer. The specific binding members can be localized using a variety of methods, such as printing methods including quill transfer or jet-type printing such as is used in ink-jet printing. These different moieties can be detected with the same or different detectable labels. The resulting pattern provides information relating to the components of the sample. Comparison of these patterns with appropriate controls can be used to determine the components and their absolute or relative concentrations. These types of results are useful for a variety of purposes, such as, for example, diagnosis of disease states or conditions or the monitoring of samples for the presence or amount of a variety of moieties, such as for environmental testing, pharmacology, pharmacogenomics, pharmacotoxicology, genomics or the like.

One preferred aspect of the present invention is the use of a traveling electromagnetic wave, which can also be described as traveling wave magentophoresis. Traveling wave magnetophoresis refers to the movement of a magnetic particle or magnetizable particle under the influence of a traveling magnetic wave. Such traveling magnetic waves can be made using the compositions and methods of the present invention. Magnetophoresis can use synchronized or be continuous. In synchronized magnetophoresis, a DC current is used such that the electromagnetic units can be address sequentially. The sequentially addressed electromagnetic units are energized in an order, such as a predetermined order, such that the magnetic particle or magentizable particle transfers from one location to another. This sequence of events causes a traveling magnetic wave to form. In continuous magnetophoresis, an AC current is used such that the electromagnetic units are addressed using currents that are out of phase, such as but not limited to about 90 degrees out of phase. Alternative phase shifts can be utilized. The phase shifts cause a traveling magnetic wave to form.

Figure 24A:
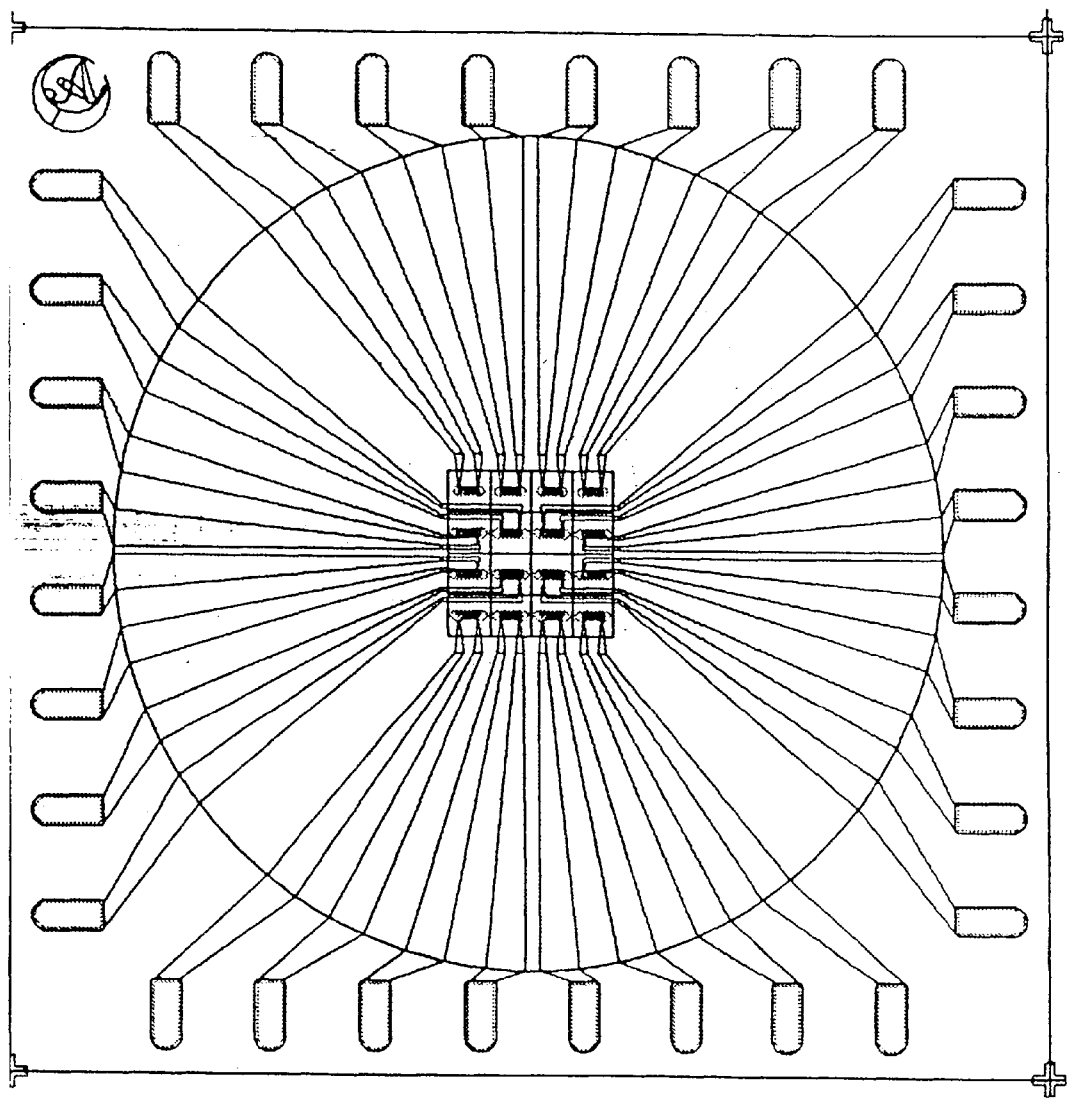
FIG. 24A and FIG. 24B depict two aspects of chips of the present invention, which are each preferably about 1 cm by 1 cm in size.
Figure 24B:
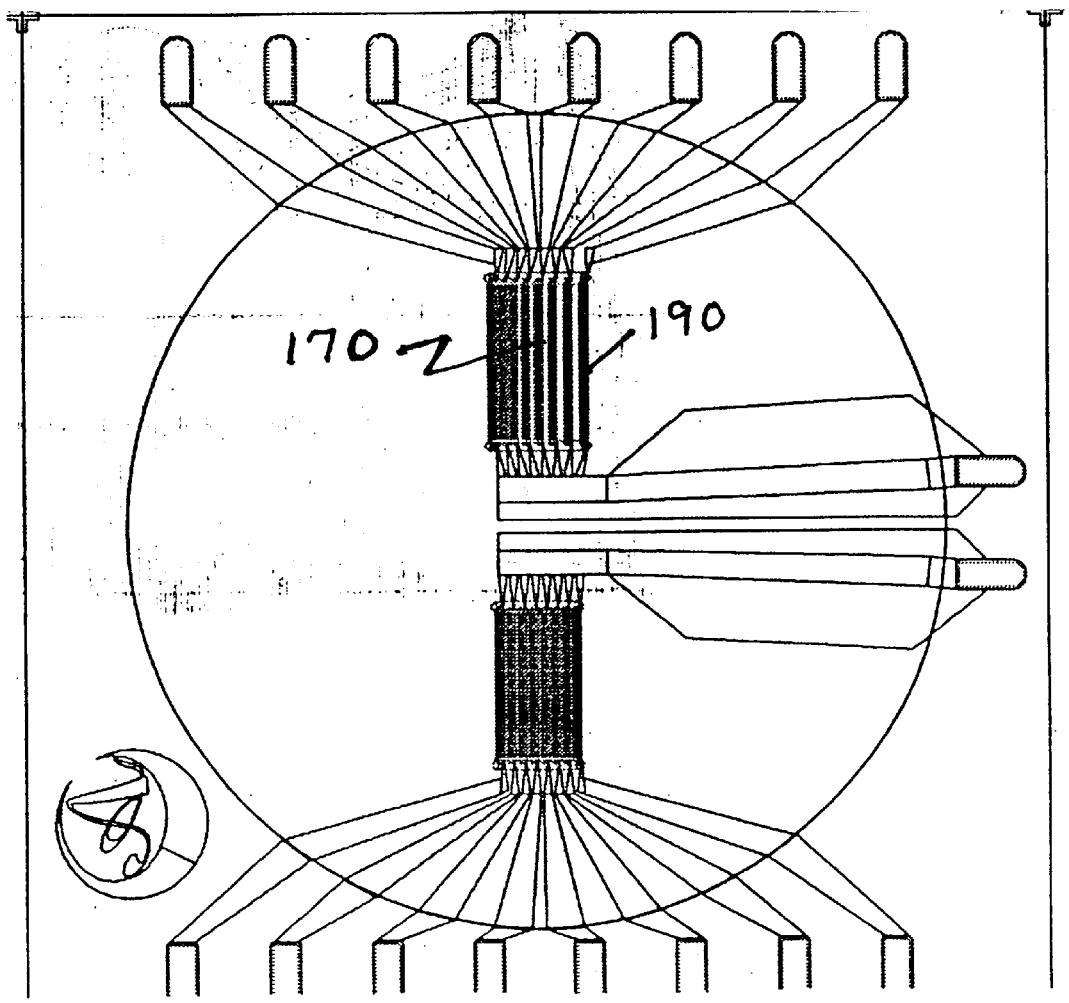

In this aspect of the present invention, a device such as depicted in FIG. 24B is provided such that the electromagnetic units (190) within a traveling wave magnetophoresis device (170) are individually addressable. The circuitry of the chip can be provided such that the electromagnetic units are activated and deactivated independently and preferably sequentially. For example, the first unit is activated, the second unit (in this case parallel to the first unit, but that need not be the case) is activated and the first unit deactivated and so on down the line of units such that the magnetic field progresses along the plurality of electromagnetic units that comprise a traveling wave magnetophoresis structure. In this way, particles such as magnetic or magnetizable particles, with or without attached moieties, are moved from one location to another.

A traveling wave magnetophoresis structure can include an appropriate number of individual electromagnetic units. These electromagnetic units can be of any appropriate size, shape and strength such that the traveling wave magnetophoresis event occurs. Preferably, a traveling wave magnetophoresis structure include between about 2 and about 1,000, more preferably between about 5 and about 500 and still more preferably between about 10 and about 100 electromagnetic units. The electromagnetic units can be of any appropriate size or configuration and having an appropriate number of coils to allow an appropriate magnetic field to be obtained. Factors to consider include the size of the units, the number of units, the strength of the units, the particles to be moved and the current to be applied. The methods described herein can be used to design, manufacture and test a variety of such structures and identify those that are capable of performing the function of traveling wave magentophoresis. A variety of electromagnetic units having different combination of such factors can be manufactured and tested for appropriate operation under desirable conditions.

In one preferred aspect of the present invention, different specific binding members can be immobilized on the chip surface, such as on a functional layer, over different loci above the traveling wave magentophoresis structure. Traveling wave magentophoresis on particles having moieties bound thereto allows the particles with moieties bound thereto to travel along the traveling wave magnetophoresis structure. Specific binding members at the different loci can capture the particles or moieties as they pass by. During or after such traveling wave magnetophoresis is accomplished, the location of one or moieties can be detected using the same or different detectable labels and/or systems. The signal from the detectable label or detectable system can be detected and optionally quantitated using devices and methods known in the art as appropriate for the particular detectable label or system. Preferred detectable labels are fluorescent and preferred detection systems include fiber optics and CCD devices, preferably fiber optic structures that collect fluorescence emission and transmit the emission to a CCD for measurement and processing.

EXAMPLES

Example 1

Electromagnetic Chips Having Vertically Oriented Micro-Electromagnetic Units

The following example refers one aspect of the electromagnetic chips of the present invention. In particular, this example describes electromagnetic chips having vertically oriented micro-electromagnetic units.

FIG. 1 shows a schematic diagram of a micro-electromagnetic chip 10 of the present invention. The chip 10 comprises a plurality of micro-electromagnetic units 11 fabricated on a substrate 16, which can be made of silicon, glass, silicon-oxide, plastics, ceramics, or other solid or porous materials. The electromagnetic units 11 on the chip 10 are arranged in a 3×3 array. The electromagnetic unit 11 is capable of inducing magnetic field (B) 17 upon the application of electric current 15, and can be selectively energized through a number of means. FIG. 1 shows that out of nine micro-electromagnetic units, six are energized with electric current to generate the magnetic fields at their vicinities. Note that the magnetic field directions are dependent on the electric current circulation direction.

In FIG. 1, electromagnetic units 11 may take the form of loops of electric conductive traces (shown as circles 15) around a center 19 that is electrically-insulated from conductive loops. The loops may be of a number of geometrical shapes such as circle, spiral, square and squared-spiral. Such conductive traces having different widths and thicknesses may be fabricated on silicon substrates using different photolithographic and fabrication protocols, as known to those skilled in the art of microlithography and microfabrication (See, for example, Rai-Choudhury P. (Editor), Handbook of Microlithography, Micromachining and Microfabrication, Volume 2: Micromachining and microfabrication. SPIE Optical Engineering Press, Bellingham, Wash., USA (1997)). Such protocols may include many basic steps, for example, photolithographic mask generation, metal deposition, insulator deposition, photoresist deposition, photoresist patterning with masks and developers, metal or insulator layer patterning. Conductive traces may be made of metal materials such as aluminum, gold, silver, tin, copper, platinum, palladium and carbon, semiconductor materials such as phosphorous-doped silicon, and any other materials as along as they conduct electric currents. For conducting electric current of sufficient magnitudes up to several hundred mA (milliampere), the conductive traces may have different cross-sectional areas up to several thousand micrometer$^2$. Thickness and width of the conductive traces may vary from 0.1 to 500 micrometer and from 1 to 500 micrometer, respectively. For each electromagnetic unit, conductive traces may be single or multiple turns. In the case of multiple turns, multi-layer microfabrication protocols may be used to fabricate these units.

In one embodiment, selective addressing of electromagnetic units comprises electric connections between electric conductive loops and current sources through electric switches. By changing the signals applied to electric switches, the flow of electric current in the conductive loops may be turned on or off so that the electromagnetic units may be energized or switched off. In another embodiment, selective addressing of electromagnetic units may be realized through a mechanical switch that turns on or off electric current to conductive loops. In both embodiments, electromagnetic units are coupled with switches, and by controlling the switches on/off status, various combinations of on/off status for electromagnetic units may be achieved.

To increase magnetic field strength induced by electric current in the conductive loops, magnetic cores made of ferromagnetic or ferrimagnetic materials may be used. In this case, each electromagnetic unit comprises a magnetic core on the substrate, single or multiple turns of electric conductive traces about the magnetic core, means for applying electric current to the conductive traces from an electric current source. Thus, the center region 19 of the electromagnetic unit 11 in FIG. 1 may be made of ferromagnetic material that is electrically-insulated from electric current loop 15. Various methods, known to those skilled in the art, may be used for depositing ferromagnetic or ferrimagnetic materials on substrates (See, for example, Ahn and Allen, A new toroidal-meander type integrated inductor with a multilevel meander magnetic core IEEE Transations on Magnetics 30: 73–79 (1994)).

Figure 2:
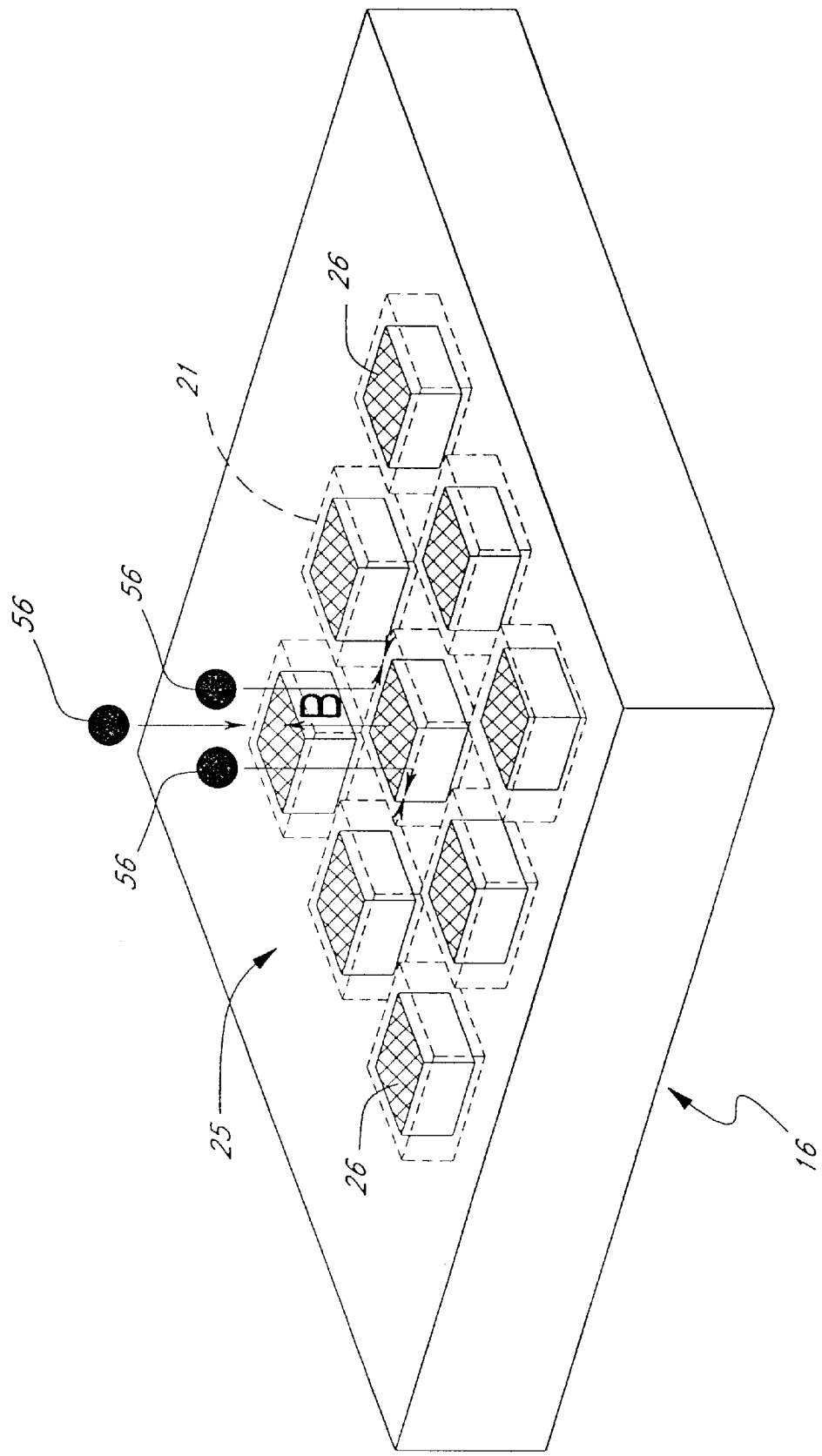
FIG. 2 depicts magnetic particles attracted towards the energized electromagnetic unit on an individually addressable micro-electromagnetic unit array chip in one aspect of the present invention. Although shown in a vertical configuration, the depicted electromagnetic units can optionally be provided independently in a horizontal configuration.

FIG. 2 shows a schematic representation of magnetic particles 21 that are directed towards an energized electromagnetic unit 11. With electric current 15 being applied to the unit, magnetic field (B) 17 is induced in the unit s vicinity, which produces magnetic forces on particles 21. As shown in Equation 3, magnetic forces are dependent sensitively on the distribution of magnetic field (B) (and field strength H). Selective addressing of electromagnetic units allows the magnetic field distribution to be controlled and changed. For example, four neighboring electromagnetic units may be energized synchronically with appropriate current flow directions to produce a magnetic quadrupole field. Magnetic field distribution may further be changed by altering electric current amplitude and direction applied to micro-electromagnetic units. The change of magnetic field distribution will in turn alter magnetic forces on magnetic particles and influence particle position, velocity and other kinetic response parameters. For example, as evidenced in Equations (2) and (3), particle velocity can be increased by increasing magnetic field strength and magnetic forces.

Figure 3:
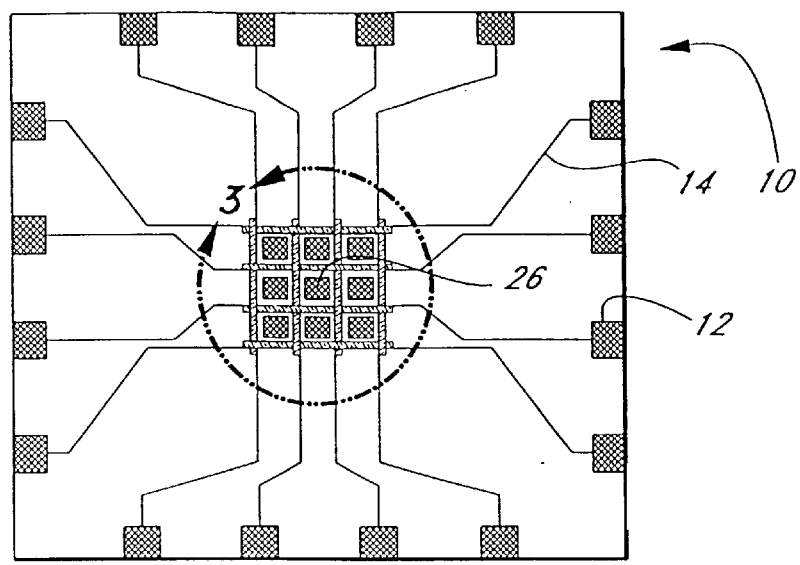
FIG. 3 depicts a schematic diagram showing the structure of one aspect of an individually addressable micro-electromagnetic biochip of the present invention. Although shown in a vertical configuration, the depicted electromagnetic units can optionally be provided independently in a horizontal configuration.

FIG. 3 shows a schematic representation of an electromagnetic biochip, which is the same as the chip shown in FIG. 1 except that a functional layer 42 has been placed on the chip surface. This functional layer is used for immobilizing ligand molecules and can include a hydrophilic or hydrophobic molecular monolayer, a hydrophilic or hydrophobic membrane, a hydrophilic or hydrophobic gel, a polymer layer, porous or non-porous materials and/or the composite of these materials. Molecular monolayer refers to single molecular layer (for example, Langmuir-Blodgett film). For immobilizing nucleic acid ligands, binding materials such as nitrocellulose or nylon may be used as in Southern or northern blots. Proteins and peptides can be bound by various physical (for example, hydrophobic) or chemical approaches. For example, specific receptors such as antibodies or lectins can be incorporated into the functional layer 42 for binding ligand molecules of protein or peptide-types. Depending on the intended ligand and the assays or reactions to be carried out by the biochip, different molecules can be incorporated into the functional layer 42 for binding ligand molecules. These molecules incorporated in the functional layer 42 for binding ligand molecules are referred to as the functional groups. Examples of the functional groups include, but not limited to aldehydes, carbodiimides, succinimydyl esters, antibodies, receptors, and lectins. The functional groups also include chemical groups or molecular sites that are formed through chemical modification on the chip surface molecules. The methods of using the electromagnetic biochips 10 in FIG. 3 will be described in later sections.

Figure 4:
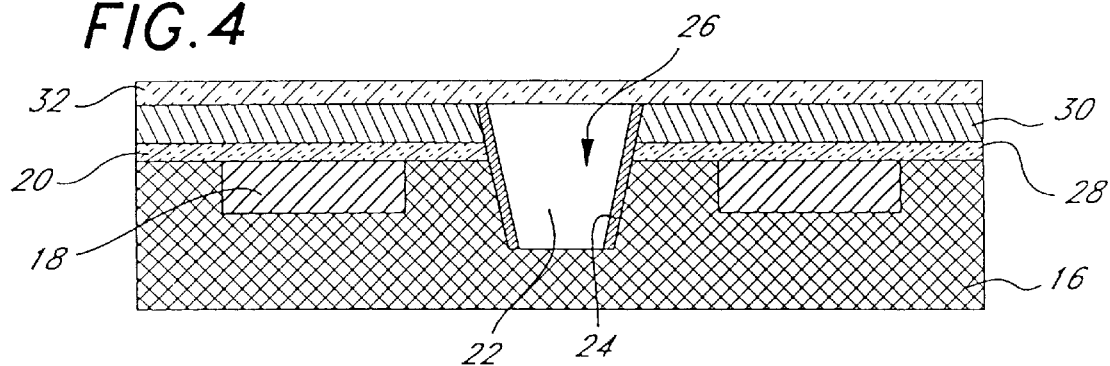
FIG. 4 depicts a cross-sectional diagram of the chip of FIG. 5. Although shown in a vertical configuration, the depicted micro-coil can be provided in a horizontal configuration.

FIG. 4 shows a schematic version of the micro-electromagnetic biochip 10 according to one embodiment of the present invention as seen from above. Connection pads 12 are in electrical communication with the electromagnetic unit array by means of conductors 14. FIG. 4 shows a detailed cross-section of a single micro-electromagnetic unit. Although similar micro-electromagnetic biochips could be fabricated on a number of substrates, the illustrated embodiment is on a silicon substrate 16 that has been polished on one surface. In the following, we describe in detail the fabrication processes for the electromagnetic biochip 10 as shown in FIG. 4. These processes are for illustrative purposes only. Those skilled in the art of microfabrication may be able to readily adapt these steps or processes and modify some of the steps for producing biochips with the same structures as shown in FIG. 4. Conductive regions are produced by surface diffusion (doping) with phosphorus to yield an electrical sheet-resistance of 2–10 Ω/square. Insulating layers of SiO$_2$ having a thickness between, for example, 1000 and 8000 Å are produced by thermal decomposition as detailed below.

Based on the dimensions and array density for the micro-electromagnetic unit array chip, parallel conductive traces 18 are photolithographically formed on the substrate 16 by phosphorus injection. The surface density of phosphorus diffusion is adjusted to give a sheet-resistance less than or equal 10_/square for conductive trace 18. Because the traces 18 are formed within the substrate 16, they have no relief and are not raised above the polished surface of the substrate 16.

After forming the first layer of conductive traces 20, an $SiO_2$ insulating layer with a thickness of 2000–4000 Å is grown on the surface of the substrate 16 by placing the chip into a high temperature oven (e.g. 1000° C.). A first insulating layer of $SiO_2$ 20 is thereby formed on the substrate 16 covering the first layer of conductive traces 18.

Using photolithography, potential cavities for electroplating are laid out at designated areas between the first conductive traces 18. For example, an array of 10 micrometers deep electroplating cavities 22 is etched by applying a KOH solution (30% w/w) to the silicon substrate 16. In cross-section each of the electroplating cavities 22 should have trapezoidal shape with its smaller parallel face towards the bottom surface of the substrate 16. An additional $SiO_2$ layer 24 with thickness of about 5000 Å is then deposited over the electroplating cavities 22, and the $SiO_2$ layer at the bottom of electroplating cavities 22 is removed by photoetching.

The cavities 22 are then filled with ferromagnetic material to create magnetic cores. This is accomplished by first placing the substrate 16 into a $NiSO_4$ solution (200–400 g/l) and heated to between 400 and 600° C. for 30 minutes under nitrogen gas, so that a seed layer of nickel with thickness of about 1 micrometer is formed at the bottom of the electroplating cavities 22.

A magnetic-core 26 for each cavity 22 can be formed by electroplating according to the following steps and conditions: (1). in $Fe/FeCl_2$ solution (ratio 200:500 g/l) at 20–40° C.; (2). in FeNi/NiSO4 solution (200:400 g/l) at 30–60° C.; (3). in $FeCl_2$ solution (10–60 g/l) at 30–60° C. Thus, an array of magnetic-core 26 is formed on the substrate 16, where the top surface of magnetic-cores 26 is higher than the top surface of the first $SiO_2$ insulation layer 20. Magnetic core 26 can be electroplated according to other conditions and steps to have compositions. For example, to obtain a nickel (81%)-iron (19%) Permalloy, an electroplating solution may have the following components: $NiSO_4 \cdot 6H_2O$ (200 g/l), $FeSO_4 \cdot 7H_2O$ (8 g/l), $NiCl_2 \cdot 6H_2O$ (5 g/l), $H_3BO_3$ (25 g/l) and Saccarin (3 g/l). An electric current density of ~5 $mA/cm^2$ may be used to have an electroplating rate of about 0.3 micrometers/minute. Other details of electroplating conditions may be found in various references (e.g., Romankiw and O Sullivan, Plating techniques in Handbook of Microlithography, Micromachining and Microfabrication, Volume 2: Micromachining and microfabrication, Editor: Rai-Choudhury P., SPIE Optical Engineering Press, Bellingham, Wash., USA (1997)).

After forming the array of magnetic-cores 26, a $Si_3N_4$ insulation layer 28 with thickness of about 5000 Å is deposited at a temperature of 200–300° C. over the magnetic-cores 26 and the first insulating layer 20. Next, a conductive layer of aluminum with thickness of about 1.2 micrometers is sputtered onto the surface of $Si_3N_4$ 28 insulation layer. A second series of conductive traces 30, perpendicular to the first series of conductive traces 18, is formed between the magnetic-cores 26 by photolithography and wet etching of the aluminum. Therefore, a micro-electromagnetic unit array is formed that consists of the array of magnetic-cores and a two dimensional network of conductive traces. The top surface of the aluminum conductive traces 30 may be even with or higher than the top surface of magnetic-cores 26.

Finally, a second $Si_3N_4$ insulation layer 32 with thickness of about 4000 Å is deposited on the surface of the aluminum conductive traces 30 at 300° C. Then, the insulating materials over the ends of the first conductive traces 18 and over the ends of the second conductive traces 30 are removed by dry etching method, so that the ends of conductive traces can be connected by the conductors 14 to the pads 12 which may then be connected to external electric circuits.

Figure 5:
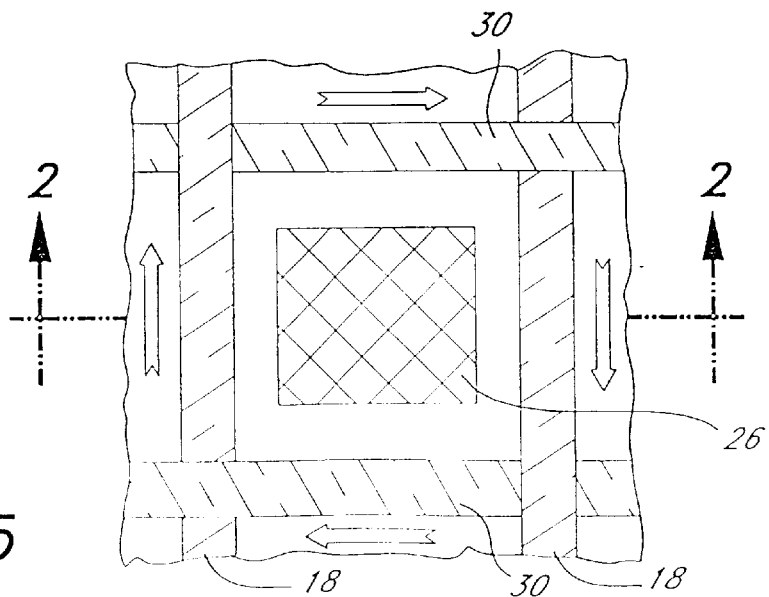
FIG. 5 depicts a schematic diagram showing the structures of one aspect of an electromagnetic chip of the present invention having individually addressable micro-electromagnetic units arranged in a column-row array. The chip is shown as seen from above. Although shown in a vertical configuration, the depicted electromagnetic unit can be provided in a horizontal configuration.

The conductive traces 18 and 30 of the micro-electromagnetic unit array are powered by a DC current source. Each individual magnetic unit of the micro-electromagnetic unit array is controlled by selectively energizing different conductive traces 18, 30. As shown in FIG. 5, the magnetic field is produced around the selected unit by selecting the direction of electric current through the surrounding traces to form a closed current loop around the magnetic-core 26. That is, to magnetize a core in a given column, the traces 18 on either side of that column are energized so that an electric current will flow up one side of the column and down the other. This current flow will have the effect of magnetizing all of the units in the column to some extent. However, any predetermined unit in the column is also a member of one of the rows of units. By causing an electric current to flow in the traces 30 on either side of that row, all of the members of the row will be magnetized to some extent; however, the selected unit, as shown in FIG. 5, will have a current flowing around all of its sides (from the row current and from the column current). This results in the selected unit being magnetized with twice the strength of the other units.

It is possible to increase the magnetic field strength of the selected unit by making a structure where the selected unit is surrounded by more than one turn of conductive trace (e.g., as in making a miniature coil). Single or multiple two dimensional conductive trace networks may be added on the top of insulation layer 32 by similar method that creating the conductive traces 18 and 30. Each network consists of two layers of conductive traces that are insulated from each other and whose position coincides with the conductive traces 18 and 30, respectively.

The magnetic strength of the selected unit can be increased further by using microfabrication methods to actually produce micro-coils surrounding each core. For a given current flow, the magnetic force developed by the core is proportional to the number of turns in the miniature coil. A large number of methods, readily apparent to one of ordinary skill in the art of microfabrication and micromachining, can be used to fabricate such micro-coils. The following approach has be used, but the invention is not limited to this method alone. The micro-coils are fabricated from conductive traces as mentioned above. Again, conductive layers of doped silicon and metal (for example, aluminum) are used alternatingly. Unlike the example given above, the conductive layers are connected in the vertical dimension. In fabricating the first layer of conductive traces 18, instead of having straight traces run on either side of a column of cores 26 each trace 34 runs almost completely around each core as shown in FIG. 6. This trace can conveniently be produced by the phosphorous diffusion process described in relation to the column traces 18. This trace is covered by an insulating layer 20 as in the simpler micro-electromagnetic array described above. A second micro-coil trace 36 is deposited on top of the insulating layer 20 as is shown in FIG. 7. Preferably, this layer is fabricated by sputtering and etching as in the case of the row traces 30 described above. Prior to the sputtering process, the insulating layer 20 is etched at vertical interconnect points 35 so that there will be a vertical connection between the micro-coil traces 34 and 36. The interconnect point 35 should be arranged so it coincides with the end-point of the first micro-coil trace 34 and the starting-point of the second micro-coil trace 36. The second layer of micro-coil traces 36 is covered by an additional insulating layer 20. The above processes are repeated to deposit a third layer of micro-coil traces 38 as shown in FIG. 8. These traces 38 like the first micro-coil traces 34 lead out of the array to row connections with conductors 14 and pads 12 (not shown). The point is that each trace layer effectively adds a single conductor turn to the micro-coil. Each micro-coil consists of a starting column layer 34 and an ending row layer 38. In between the column and row layer there can be a variable number of loop layers 36 depending on the desired number of turns in the micro-coil. Note that the gap 40 of each successive layer is offset slightly. Such offset is necessary to ensure that the interconnect point 35 always coincides with the end-point of the conductive trace loop in one layer and the starting point of the conductive trace loop in the successive layer. Alternatively, some of the micro-coil trace layers can be implemented with doped silicon as in the initial column traces 18. This choice is a matter of design preference and may alter the profile of the device. One way of using doped silicon is to deposit a layer of amorphous silicon above the insulating layer 20 and then create the illustrated trace patterns by photolithographic directed doping. After all the micro-coil layers except the final row layer have been fabricated, the cavities 22 are created by etching and the ferromagnetic cores 26 are formed by electroplating. Then the final micro-coil row layer 38 and the insulating capping layer 32 are created to complete the structure.

Advantages of the micro-coils are that a stronger magnetic force (proportional to the number of micro-coil turns) is developed by each magnetic core. Further, when a selected core is magnetized by selecting a given column and row, the other cores may be magnetized only to a very small extent or not at all.

Figure 10:
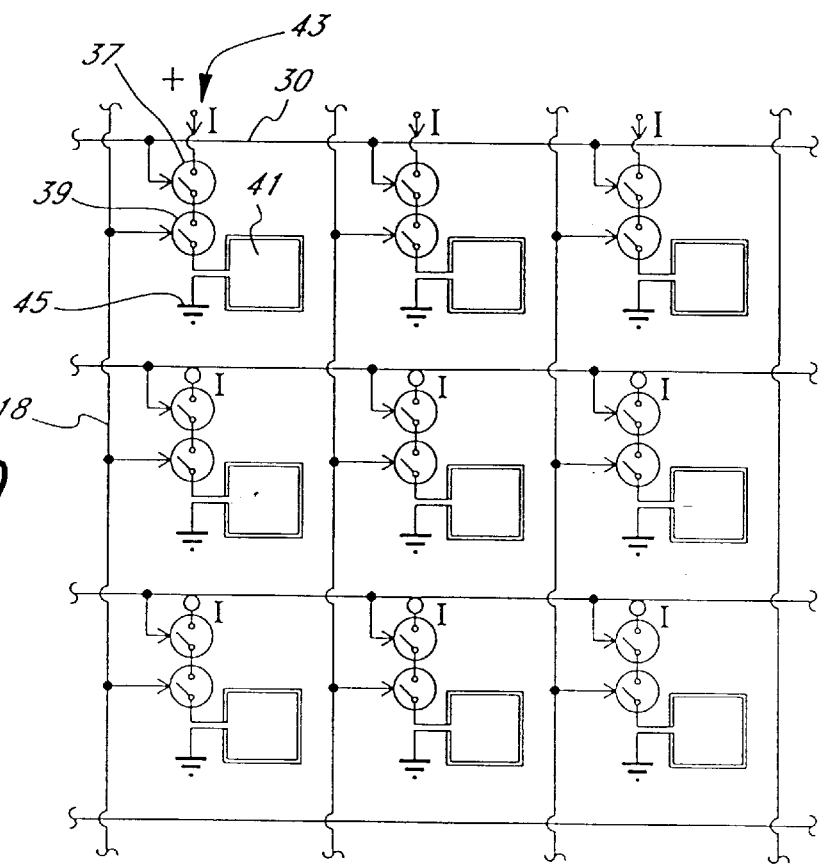
FIG. 10 depicts a schematic diagram showing the principle of addressing individual micro-electromagnetic units by using electric switches in one aspect of the present invention. In this figure, each unit is connected to the current source and the common ground through two electric switches connected in series and the two switches are controlled by electric signals applied to the rows and columns of the electric conductive lines. Although shown in a vertical configuration, the depicted electromagnetic units can optionally be provided independently in a horizontal configuration.
Figure 11A:
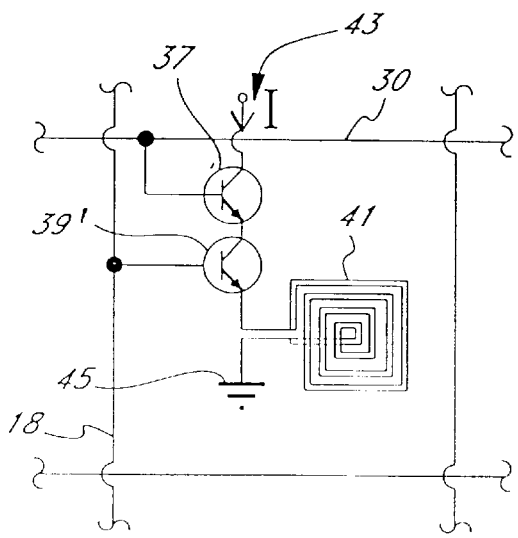
FIG. 11A depicts that in this aspect of the present invention, an electric switch is a bi-polar transistor. Although shown in a vertical configuration, the depicted electromagnetic units can optionally be provided independently in a horizontal configuration.
Figure 11B:
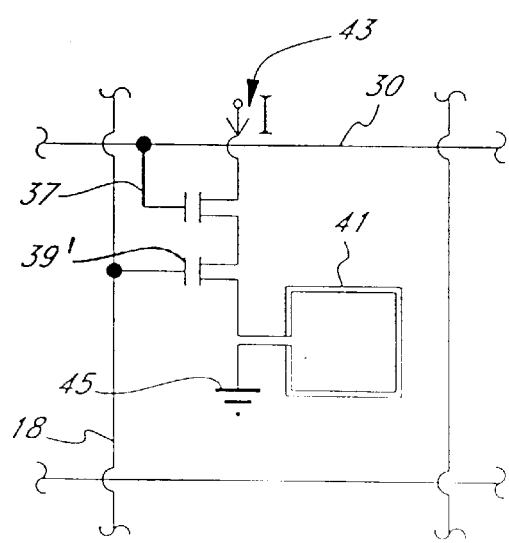
FIG. 11B depicts that in this aspect of the present invention, an electric switch can be a MOSFET (Metal-Oxide-Semiconductor-Field-Effect-Transistor). Although shown in a vertical configuration, the depicted electromagnetic units can optionally be provided independently in a horizontal configuration.
Figure 11C:
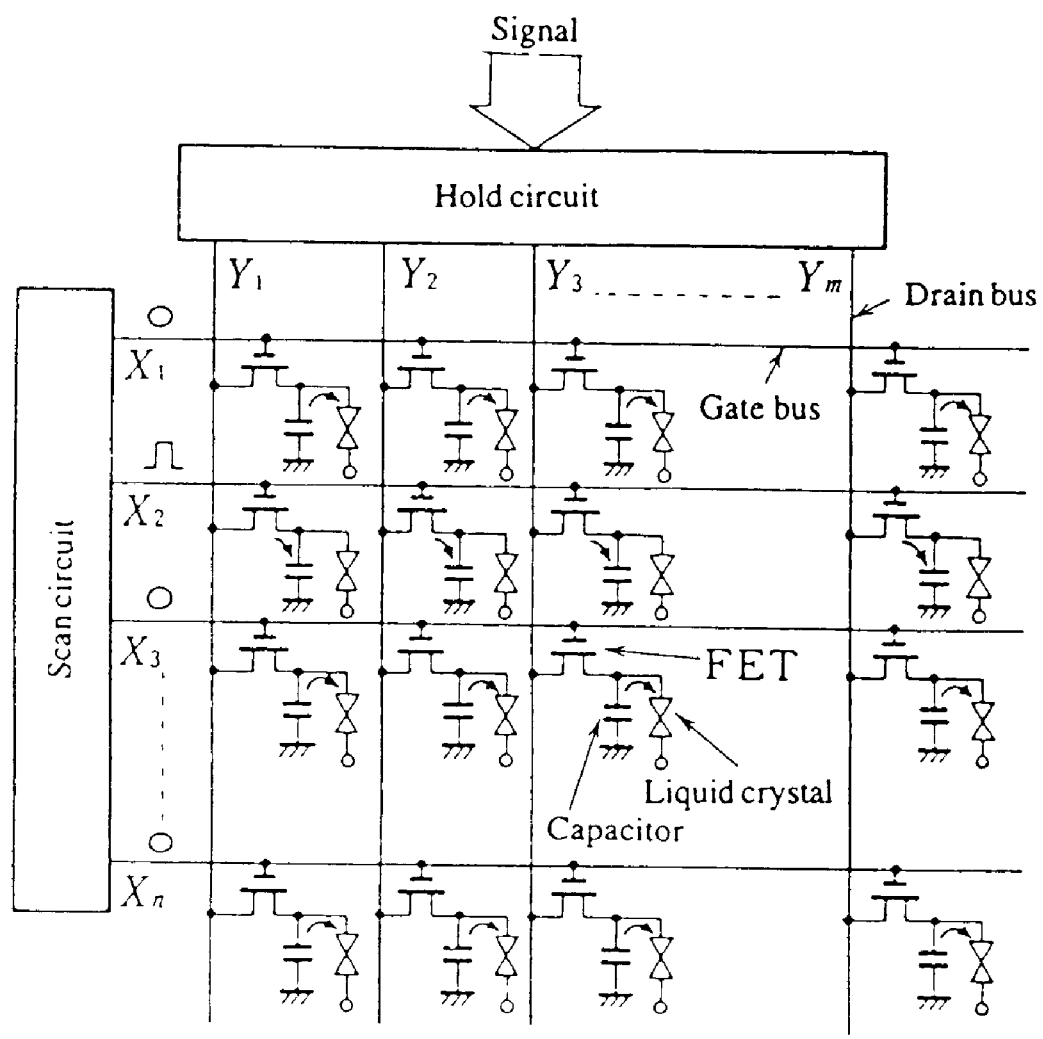
FIG. 11C depicts circuitry using liquid crystal display technology useful in the present invention as is known in the art.

FIG. 10, FIG. 11A, FIG. 11B and FIG. 11C show the principle of addressing individual micro-electromagnetic units by using electric switches. In FIG. 10, each unit 41 is connected to the common electric current source 43 and the common ground 45 (i.e. a current sink) through two electric switches 37 and 39 in series. The switch 37 is controlled by electric signals applied to the rows 30 of the electric conductive lines. The switch 39 is controlled by electric signals applied to the columns 18 of the electric conductive lines. An individual unit 41 is switched on (i.e. there is a current flow from the current source 43 to the unit 41 and through the unit to the ground 45) when and only when both electric switches are turned on. An electric switch can be, for example, a bi-polar transistor as shown in FIG. 11A, a MOSFET (Metal-Oxide-Semiconductor Field-Effect-Transistor) as shown in FIG. 11B or a matrix drive LCD as shown in FIG. 11C. Thus, the electric potentials applied to the base of the bi-polar transistors or to the gate of the MOSFETs determine the on/off status of these electric switches. The unit 41 is shown as a square loop of single turn in FIG. 10 and FIG. 11B, and as a squared-spiral loop of multiple turns in FIG. 11A. These transistors can be readily fabricated using the similar fabrication techniques to those used for producing the micro-electromagnetic array described above, and can be integrated together with the electric conductive loops on a same substrate. The current source 43 and common ground 45 may take the forms of two separate conductive layers in the final structure, and are connected to two output points of a DC power supply. The current going through a micro-electromagnetic unit will be equal to the voltage from the power supply divided by the total resistance of the current-flowing circuit (including the resistance of the on-state electric switches and of the conductive loops). In the foregoing examples, the substrate material is silicon, but other materials, such as glass, silicon dioxide, ceramics or even plastics, etc., may also be used as substrates. The substrate can be made of porous or non-porous materials. Similarly, the materials for the insulation layers 20, 28, and 32 are not limited to the materials used in this example, but may be plastics, glass, photoresist, rubber, ceramics etc. The conductive traces may be aluminum, gold, tin, copper, platinum, palladium, carbon, semiconductor materials or composite of above materials. Similarly, other configurations of the conductive traces and micro-coils are possible. The illustrated method of producing a magnetic-core by electroplating is merely an example. Magnetic cores can be deposited in proper relation to conductive traces (micro-coils) by means of electron beam evaporation, sputtering or other deposition techniques well-known to those of skill in the art of microfabrication and micromachining. Furthermore, magnetic cores can be fabricated from a wide range of ferromagnetic or ferrimagnetic materials deposited by electron-beam evaporation, sputtering and other such methods. The present invention comprises individually controllable micro-electromagnetic units on a substrate. Using such chips, directed manipulation of biomolecules, chemical reagents and drug molecules is made possible through the application of magnetic fields.

After the micro-electromagnetic array chips are fabricated, the surface of top insulation layer 32 may be chemically modified or may be coated with a thin film layer. This layer is called functional layer 42, which is used for immobilizing ligand molecules. Illustrated in FIG. 13, the functional layer 42 may be hydrophilic or hydrophobic molecular monolayer, a hydrophilic or hydrophobic membrane, a hydrophilic or hydrophobic gel, a polymer layer, or the composite of these materials, as described in the section related to FIG. 3. The functional layer may be made of porous or non-porous materials. The functional layer 42 may incorporate specific molecules such as antibodies for binding ligand molecules, depending on the intended ligand and the assays or reactions to be carried out on the biochip. These molecules incorporated in the functional layer for attaching or binding ligand molecules are referred to as functional groups. For immobilizing nucleic acid ligands binding materials such as nitrocellulose or nylon, polylysine, agarose gel, hydrogel, acrylamide gel as used in Southern or northern blots may be used as functional layers. For immobilizing proteins and peptides, antibodies or other protein molecules may be incorporated into the functional layer 42 and used as the functional groups.

Figure 13:
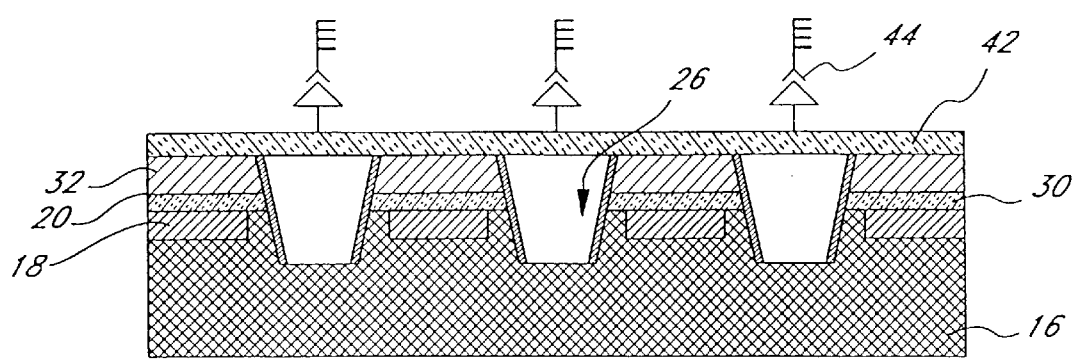
FIG. 13 depicts a schematic representation showing magnetic modification of ligand or target molecules through a cleavable chemical linker in one aspect of the present invention. Although shown in a vertical configuration, the depicted electromagnetic units can optionally be provided independently in a horizontal configuration.

After the formation of functional layer, the ligand molecules 44 that have been magnetically modified or loaded (as explained below) can be immobilized onto the functional layer 42 by reacting with different function binding moiety provided. In FIG. 13, a lock in key reaction such as that characteristic of an antibody is illustrated, but clearly the immobilization is not limited to this type of reaction. The precise site of immobilization on the functional layer 42 is controlled by the magnetic fields generated by the electromagnetic units. That is, in most cases the ligand will be immobilized immediately above a unit if a single electromagnetic unit 26 is magnetized. As is well-known, the polarity of an electromagnet is controlled by the direction of current flow about the electromagnet unit. Depending on the direction of current flow (clockwise or counterclockwise) the units will have either North poles or South poles pointing towards the functional layer 42. Thus, when two adjacent electromagnetic units are energized to have either the same polarity or opposite polarities, the superimposition of the magnetic fields due to the two electromagnetic units will determine the magnetic forces acting on magnetically-modified ligands and determine where the ligands will be immobilized. It is possible to energize neighboring electromagnetic units in a synchronized way to alter magnetic field distribution and to change the forces acting on magnetically-modified molecules. In order to hold the affinity ligands, reagents and reactants, and to allow for addition and removal of the liquids, a fluid chamber 46 is constructed around the chip 10. A diagram of such a chambered biochip is shown in FIG. 12. The chip 10 is enclosed in a suitable chamber 46 of plastic or other materials. Inlets and outlets 48 are provided for liquid flow. A quartz coverslip 50 (glass or other optically transparent material can be used; quartz is a good material for ultra-violet measurements) is sealed to the top of the chamber 46 with silicone rubber or other suitable material. The coverslip 50 allows optical detection of ligands and reaction products within the device. Alternatively, if non-optical detection methods are employed, the chamber top 50 does not have to use optically-transparent materials.

Example 2

Electromagnetic Chips Having Horizontally Oriented Micro-Electromagnetic Units

The following example refers one aspect of the electromagnetic chips of the present invention. In particular, this example describes electromagnetic chips having horizontally oriented micro-electromagnetic units.

Although Example 1 describes electromagnetic chips having micro-electromagnetic units in a vertical configuration ("vertical units"), the present invention includes electromagnetic chips having micro-electromagnetic units in a horizontal configuration ("horizontal units") as well, or a combination thereof. These horizontal units are made in manners similar to the vertical units, but due to the size and shape of the horizontal units, the horizontal units have different performance properties that make them well suited for use in the methods of the present invention.

A variety of horizontal units were made using methods described herein. The variables considered while designing and making these horizontal units were the dimension of the core, such as the thickness and length thereof, and the number of coil turns. In order to reduce demagnetized fields and increase pole density, the core can be made longer with a larger length vs. cross section ratio. The magnetic filed can also increase as the cross section increases. Pole density can also be increased during operation by applying current to levels until reaching saturating current. Core dimensions utilized for designing horizontal units are (in micrometers):

| | | | | |
|---|---|---|---|---|
| 200 × 50 × 5 | 200 × 25 × 5 | 200 × 50 × 2 | 200 × 25 × 2 | 1600 × 50 × 5 |
| 400 × 50 × 5 | 400 × 25 × 5 | 400 × 50 × 2 | 400 × 25 × 2 | 1600 × 25 × 5 |

Designs using these core dimensions include the core, coil and contact structures.

Figure 15:
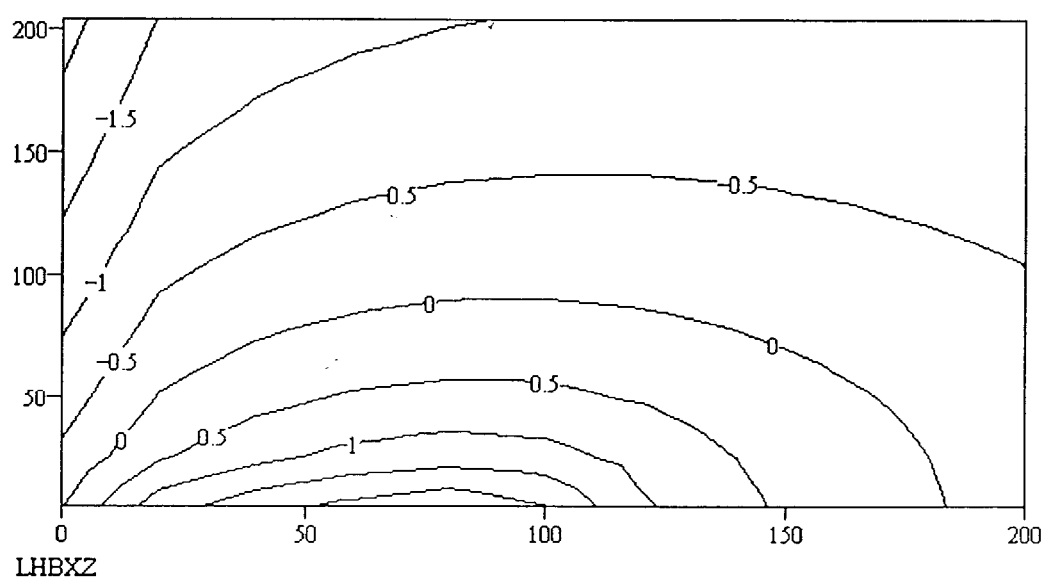
FIG. 15 depicts a contour plot of the log of the magnetic filed over a 200×200×5 micron bar plane above an electromagnetic unit such as depicted in FIG. 14 having a core having dimensions of 200 microns×20 microns×5 microns.
Figure 16:
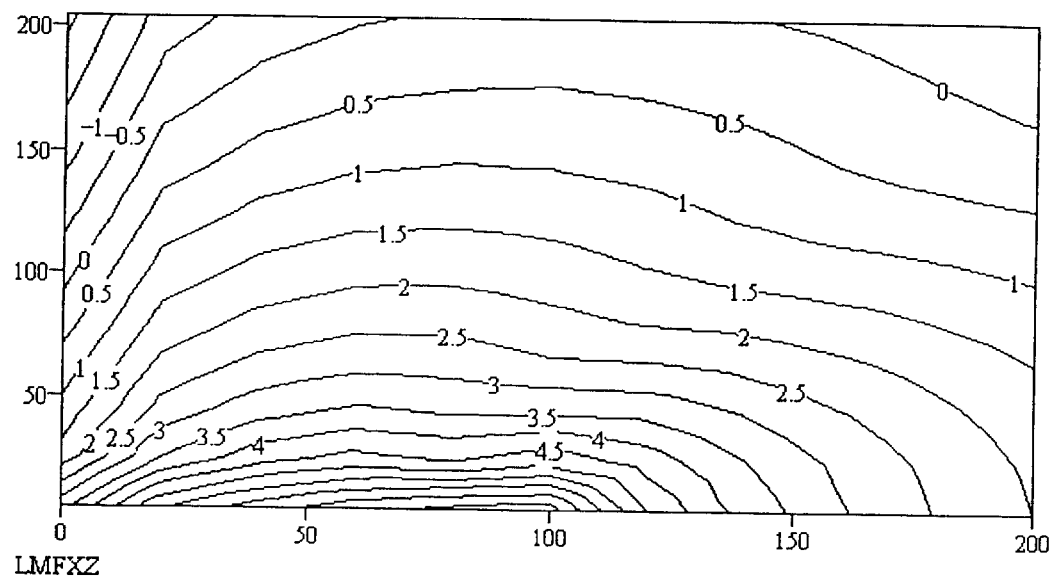
FIG. 16 depicts a plot of the log of the magnetic force in the same plane as described in FIG. 15.

FIG. 14 depicts the layout of a horizontal unit having a core wrapped by a 12-turn solenoidal coil. The core is about 200 microns by about 50 microns with a thickness of about 5 microns. The field calculations based on this design were made using a 20 milliamp current. FIG. 15 is a contour plot of the log of the magnetic field over a vertical 200 micron× 200 micron plane above the core, starting from the center of the bar. FIG. 16 shows the log of the $H_m \cdot \Delta B_m$ ($gauss^2$/ cm) (which is proportional to the magnetic force) in the same plane as FIG. 15. FIG. 14B, FIG. 14C and FIG. 14D depict micrographs of such units.

Figure 17:
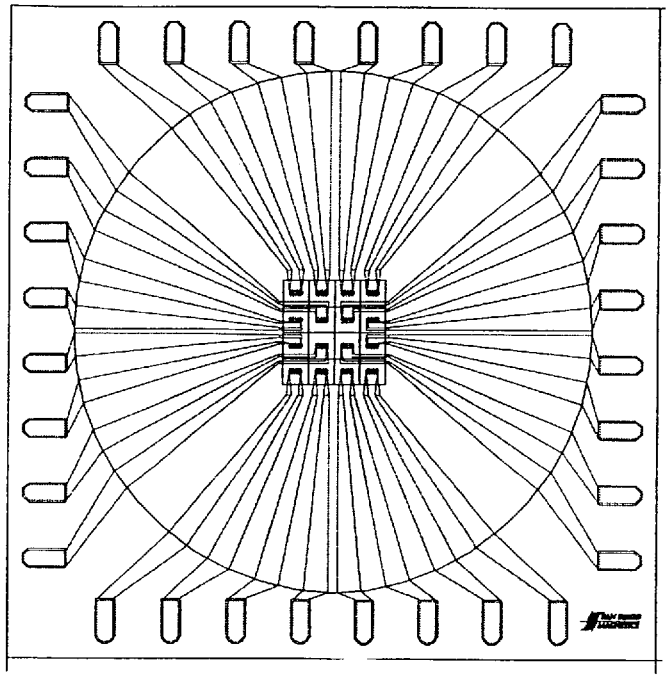
FIG. 17 depicts one aspect of an electromagnetic chip of the present invention having sixteen individually controllable horizontal electromagnetic units. This electromagnetic chip is preferably about 1 cm×1 cm in size.
Figure 18:
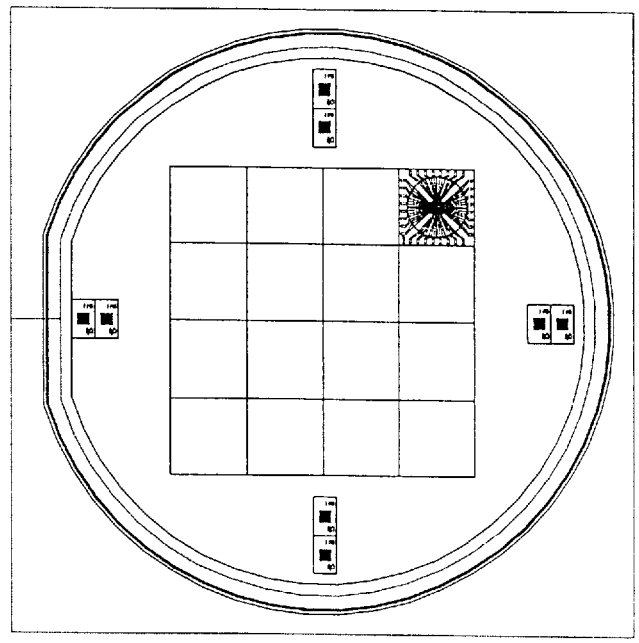
FIG. 18 depicts a wafer that can include sixteen of the electromagnetic chips depicted in FIG. 17. This electromagnetic wafer is shown approximately in a scale of 1:1.

Electromagnetic chips having horizontal units can be made on three-inch wafers, which allows for sixteen chips having a size of 1 cm×1 cm to be made. Each of the 1 cm×1 cm chips can be designed to have sixteen individually addressable and controllable horizontal units. An example of a 1 cm×1 cm chip with sixteen horizontal units is provided in FIG. 17. A waver with sixteen chips is depicted in FIG. 18.

Figure 14A:
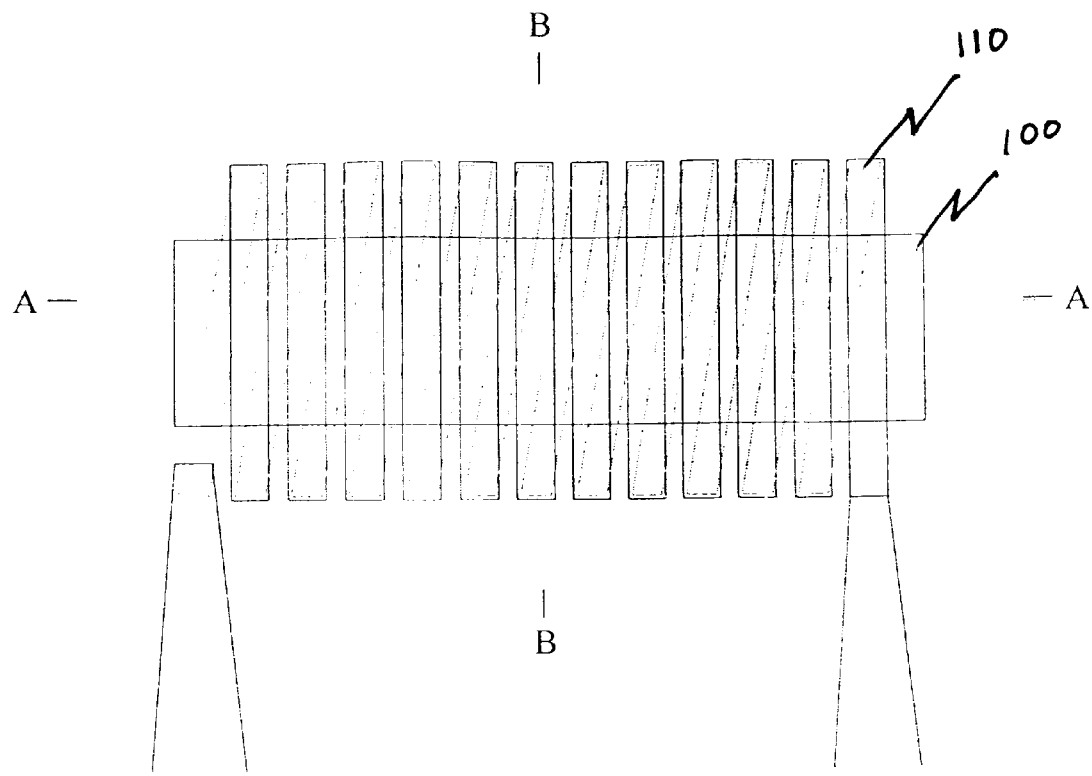
FIG. 14A depicts a top view of one aspect of a horizontal electromagnetic unit of the present invention showing core (100) and coil (110).
Figure 14B:
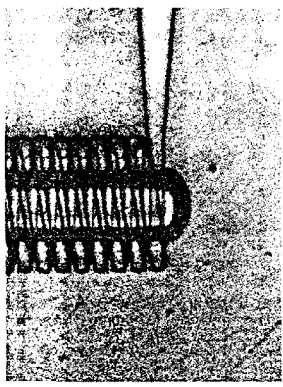
FIG. 14B, FIG. 14C and FIG. 14D are micrographs of micro-electromagnetic units of the present invention.
Figure 14C:
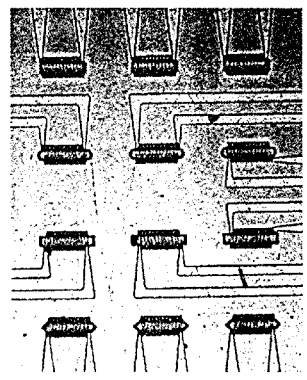
Figure 14D:
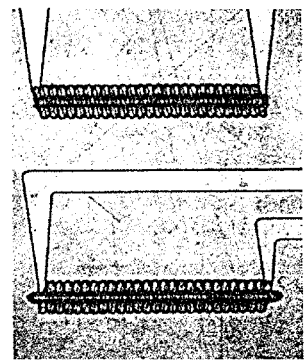
Figure 19A:
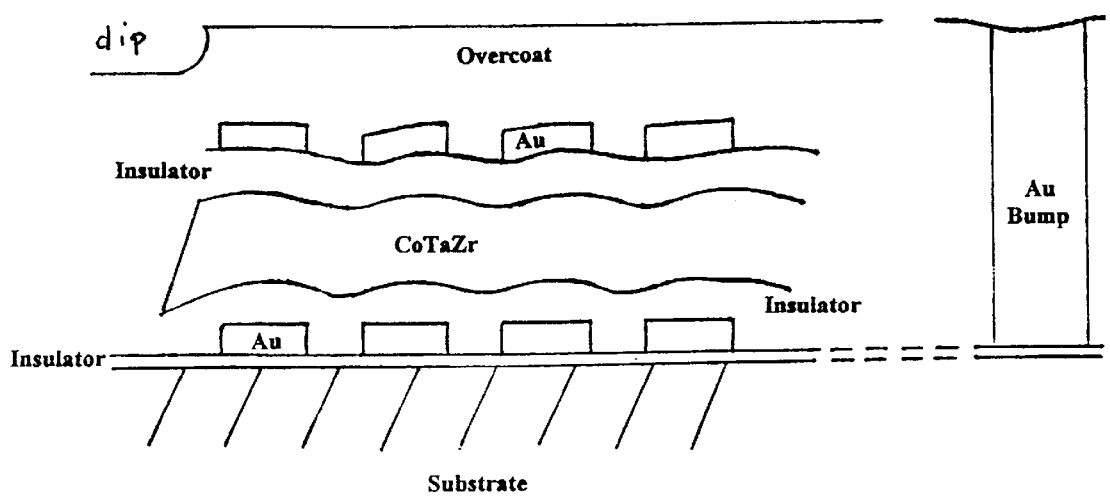
FIG. 19A depicts a cross section through an electromagnetic unit of the present invention through A—A of FIG. 14A.
Figure 19B:
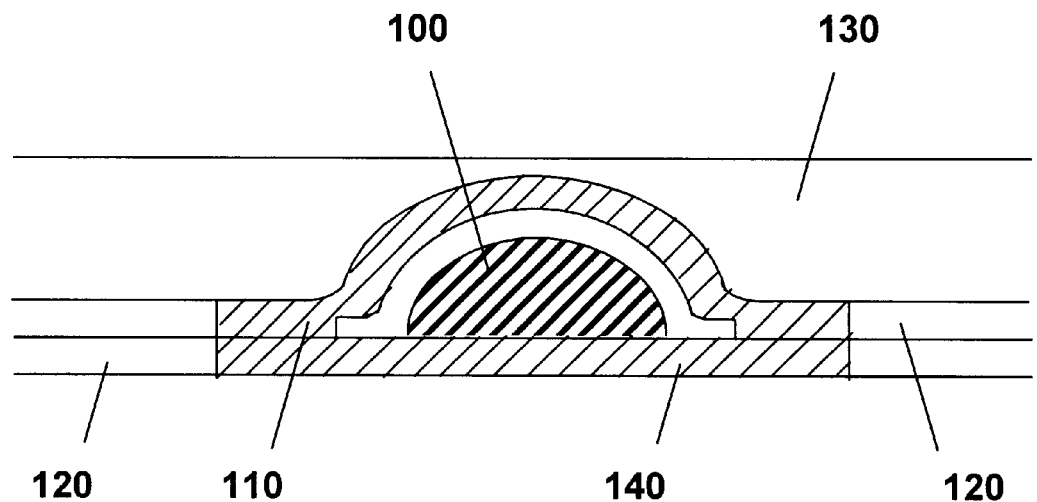
FIG. 19B depicts a cross-section through an electromagnetic unit of the present invention through B—B of FIG. 14A showing the core (100), coil (110), insulating material (120), overcoat (130) and conductive material (140).

A cross section of a horizontal unit along A—A for FIG. 14A is provided in FIG. 19A and along B—B for FIG. 14A is provided in FIG. 19B. Generally, the substrate, such as Si or glass, is shown as is a core comprised of CoTaZr that is surrounded by insulator wherein a gold coil structure surrounds the coil, and a gold bump allows connection with the coil. The PVT gold coil is deposited on a silicon substrate activated by $SiO_2$. An insulator layer, such as photoresist, Si $SiO_2$, SiN or $Al_2O_3$, separates the coil and the core. The insulator layer should be maintained in a reasonably planar configuration for later deposition of core material. The core is passivated and vias are opened to connect the top and bottom coils. Gold pads are plated for wire bonding and a thick overcoat of overcoat material protects the structure. The overcoat is lapped to create a flat surface. Depressions in the overcoat can be formed by appropriate methods at the vicinity of the ends of the core in order to collect particles attracted thereto.

The horizontal units are made using the same general methods described for the vertical units. Based on two types of insulating material, two processes for making horizontal units are provided. In the follow tables, PR refers to photoresistance.

| Process Step | Materials | Method |
|---|---|---|
| Resist Insulation | | |
| Substrate Clean and Bake | Thermal Oxide Si | Scrubber |
| Alignment Target Deposition | Cr or Ti | Sputter |
| Alignment Target Mask | Positive PR | Coat/Align/Develop |
| Alignment Target Etch | | Ion Mill |
| Alignment Target SCI | Stripper | Visual Inspection |
| Passivation | $SiO_2$ or $Al_2O_3$ at 0.5 micrometers | Sputter, evaporation of deposition |
| First Coil Mask | Negative PR | Coat/Align/Develop |
| First Coil Deposition | Cr/Au at 1.0 micrometers | E-beam Evaporation |
| First Coil Liftoff and Inspect | Stripper | Liftoff/visual/etching |
| Coil Planarization | PR | Coat/Align/Develop/Bake |
| Magnetic Pole Deposition | CoTzZr at 2.0/ 5.0 micrometers | Sputter/Deposition |
| Magnetic Pole Anneal | | Magnetic Vacuum Bake/Measure |

-continued

| Process Step | Materials | Method |
|---|---|---|
| Magnetic Pole Mask | Positive PR | Coat/Align/Develop |
| Magnetic Pole Etch | Acid | Chemical Etching |
| Magnetic Pole SCI | Stripper | Visual Inspection |
| Magnetic Pole Passivation Mask | PR | Coat/Align/Develop/Bake |
| Second Coil Mask | Negative PR | Coat/Align/Develop |
| Second Coil Deposition | Cr/AU at 1.0 micrometers | E-beam Evaporation |
| Second Coil Liftoff and Inspect | Stripper | Liftoff/visual |
| Coil Resistance Test | Probe Card | Prober |
| Coil Passivation Mask | PR | Coat/Align/Develop/Bake |
| Gold Plating Base Deposition | Ti/Au | Sputter |
| Gold Bump Mask | Positive PR | Coat/Align/Develop |
| Gold Bump Plating | Au | Plating |
| Gold Base Etch | | Ion Mill |
| Overcoat Deposition | SiO$_2$ or Al$_2$O$_3$ at 5 to 10 micrometers | Sputter |
| Overcoat Lapback Bond Pads Clear | Diamond Slurry | Lapping Ion Mill |
| Dip Mask | Positive PR | Coat/Align/Develop |
| Dip Etch | Acid | Chemical Etch |
| Dip SCI | Stripper | Visual Inspection |
| Final Test | Probe Card | Prober |
| Oxide Insulation | | |
| Substrate Clean and Bake | Thermal Oxide Si | Scrubber |
| Alignment Target Deposition | Cr or Ti | Sputter |
| Alignment Target Mask | Positive PR | Coat/Align/Develop |
| Alignment Target Etch | | Ion Mill |
| Alignment Target SCI | Stripper | Visual Inspection |
| Passivation | SiO$_2$ or Al$_2$O$_3$ at 0.5 micrometers | Sputter, evaporation of deposition |
| First Coil Mask | Negative PR | Coat/Align/Develop |
| First Coil Deposition | Cr/Au at 1.0 micrometers | E-beam Evaporation |
| First Coil Liftoff and Inspect | Stripper | Liftoff/visual/etching |
| Coil Passivation | SiO$_2$ or Al$_2$O$_3$ at 1.0 micrometers | Sputter |
| Magnetic Pole Deposition | CoTzZr at 2.0/5.0 micrometers | Sputter/Deposition |
| Magnetic Pole Anneal | | Magnetic Vacuum Bake/Measure |
| Magnetic Pole Mask | Positive PR | Coat/Align/Develop |
| Magnetic Pole Etch | Acid | Chemical Etching |
| Magnetic Pole SCI | Stripper | Visual Inspection |
| Magnetic Pole Passivation Mask | SiO$_2$ or Al$_2$O$_3$ at 1.0 micrometers | Sputter |
| Coil Vias Mask | Positive PR | Coat/Align/Develop |
| Coil Vias Etch | Acid | Chemical Etch |
| Coil Vias SCI | Strippers | Visual Inspection |
| Second Coil Mask | Negative PR | Coat/Align/Develop |
| Second Coil Deposition | Cr/Au 1.0 micrometers | E-beam Evaporation |
| Second Coil Liftoff and Inspect | Stripper | Liftoff/visual |
| Coil Resistance Test | Probe Card | Prober |
| Coil Passivation | SiO$_2$ or Al$_2$O$_3$ at 1.0 micrometers | Sputter |
| Pat Vias Mask | Positive PR | Coat/Align/Develop |
| Pad Vias Etch | Acid | Chemical Etch |
| Pad Vias SCI | Stripper | Visual Inspection |
| Au Plating Base Deposition | Ti/Au | Sputter |
| Gold Bump Mask | Positive PR | Coat/Align/Develop |
| Gold Bump Plating | Au | Plating |
| Gold Base Etch | | Ion Mill |
| Overcoat Deposition | SiO$_2$ or Al$_2$O$_3$ at 5 to 10 micrometers | Sputter |
| Overcoat Lapback Bond Pads Clear | Diamond Slurry | Lapping Ion Mill |
| Dip Mask | Positive PR | Coat/Align/Develop |
| Dip Etch | Acid | Chemical Etch |
| Dip SCI | Stripper | Visual Inspection |
| Final Test | Probe Card | Prober |

Either of these processes utilizes seven mask for photolithography processes. The choice of using photoresist or oxide as an insulator between the core and the coils depends on some factors, particularly the fluorescent property of the photoresist material. Different photoresist materials have different fluorescent properties as is known in the art. These materials can be tested and screened to determine appropriate photoresist materials for use in applications where fluorescence detection methods may be used. In general, the materials Al$_2$O$_3$ and SiO$_2$ are preferable.

Three chips having horizontal units were made and tested. The horizontal units had the following sizes of cores (in micrometers):

200×50×5  400×50×5  1600×50×5

The measured magnetic field above the end of the core was approximately 50% of the value derived by modeling for each of the three test devices, which may be due to process offsets in the prototype devices.

The devices were measured with a five micron trace width MR head using a manual X-Y-Z planar stage having a positioning resolution of 25 microns. The MR head was wired into a full bridge and a sense current of approximately 10 milliamps was applied to the horizontal unit. The bias point was adjusted by setting the magnetization of a thin film permanent magnet within the MR head. The data obtained was recorded u sing a YEW type 3033 XY recorded with differential amplifier modules. The X-axis recorded the current applied to the horizontal unit and the Y-axis recorded the signal from the MR head.

Figure 20:
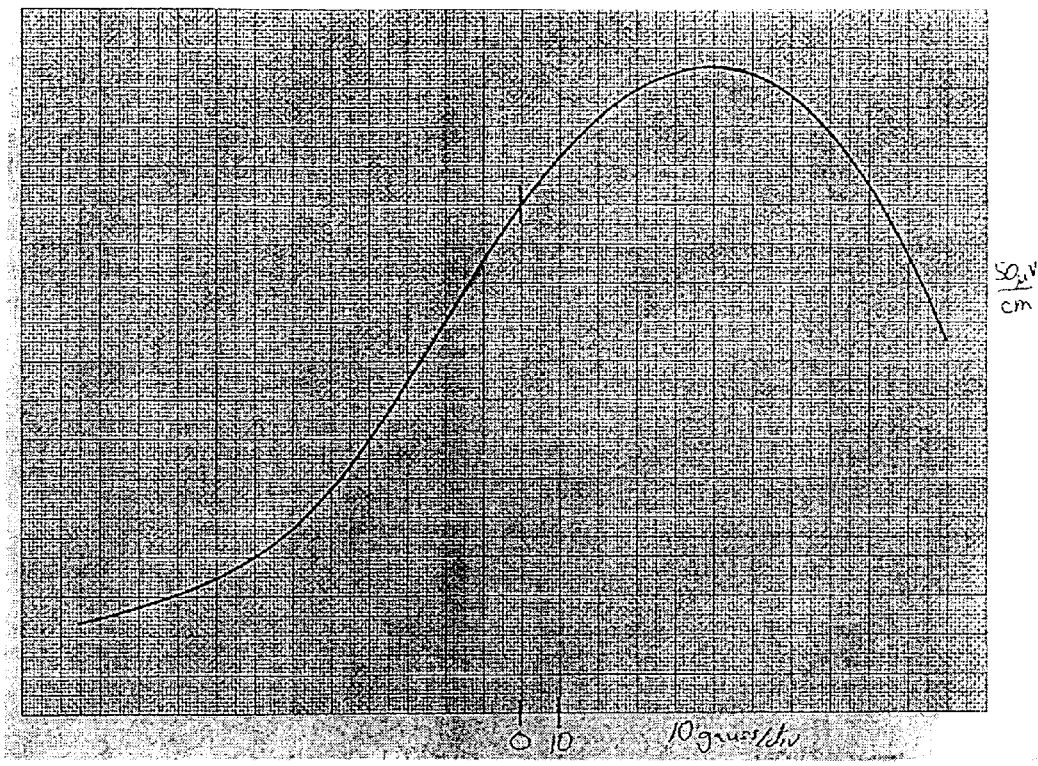
FIG. 20 depicts a calibration curve for a MR head used to evaluate certain aspects of electromagnetic units of the present invention.

Prior to testing, the MR head was calibrated using a Helmhotz coil. The calibration was made over the range of ±100 gauss. FIG. 20 provides the calibration curve. The MR head was mounted to the stage and roughly positioned over the end of a core of a device to be tested. The height of the head was set to approximately 50 microns. The device was energized with a large current and the head positioned in the X-Y plane to obtain a maximized signal, which was determined to be at the ends of the core, where remaining measurements were taken.

With the MR head in place, data can be obtained. The MR head is sensitive to temperature, so thermal effects should be addressed and reduced. Thermal effects can be reduced by driving the device with a low frequency (0.25 Hz) square wave so that thermal equilibrium of the device and head system is reached after a few cycles because the magnitude of the current is constant. The field can be determine by assuming the −B at negative current equals +B at positive current.

In addition to field v. current and field v. z height measurements, the hysteresis of the devices was measured. It was found that the devices have some remnance, but that by bringing the current to zero with decreasing amplitude oscillating current the device is demagnetized.

Figure 21:
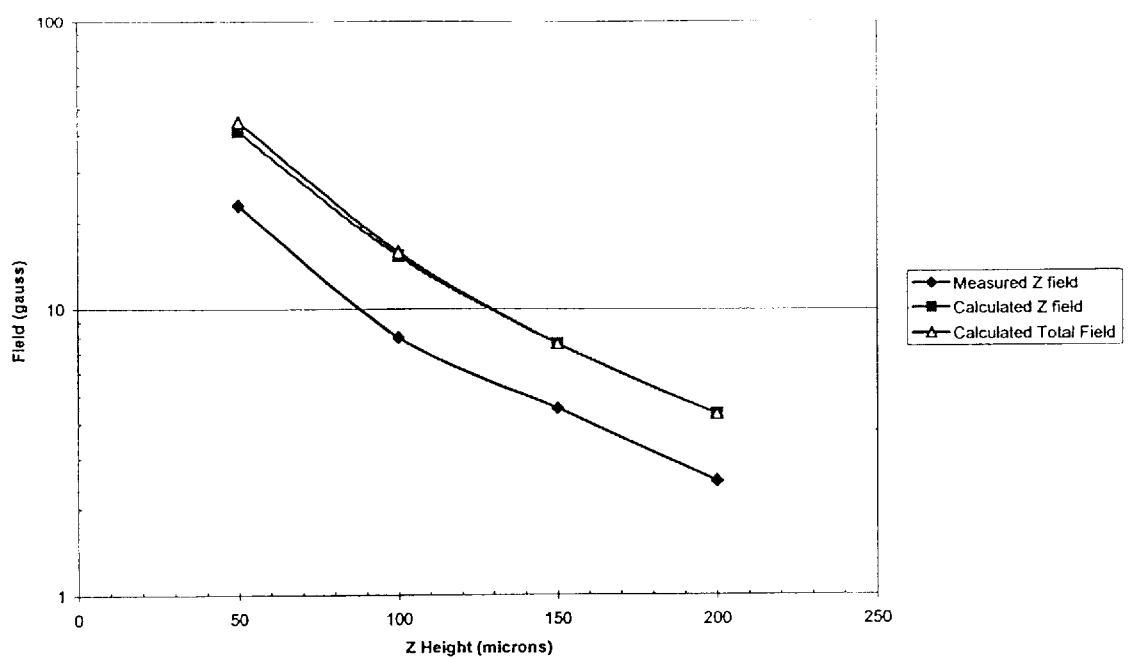
FIG. 21 is a plot the depicts the measured and modeled values for field v. distance for one aspect of an electromagnetic unit of the present invention having a core having the dimensions, in micrometers, of 400×50×5.
Figure 22:
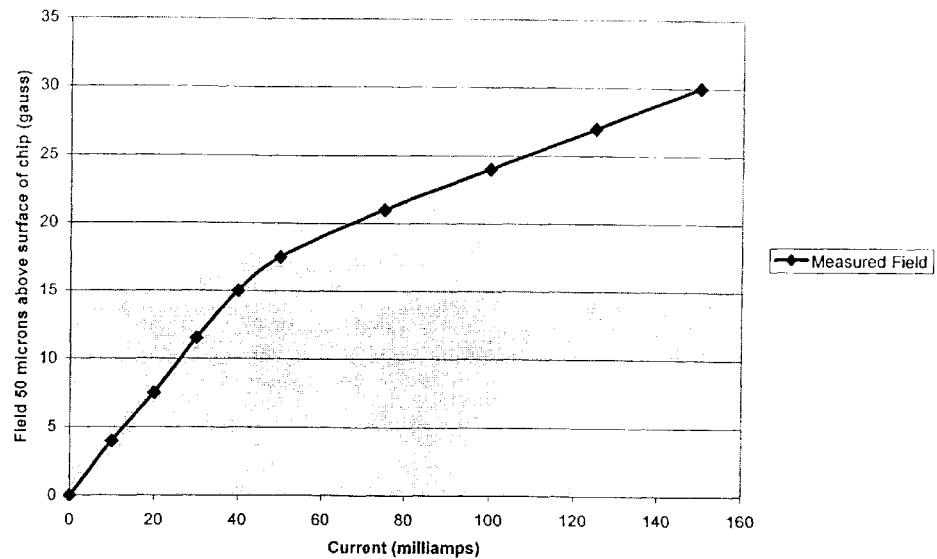
FIG. 22 is a plot that depicts the field v. current for one aspect of an electromagnetic unit of the present invention having a core having the dimension, in micrometers, of 400×50×5.
Figure 23:
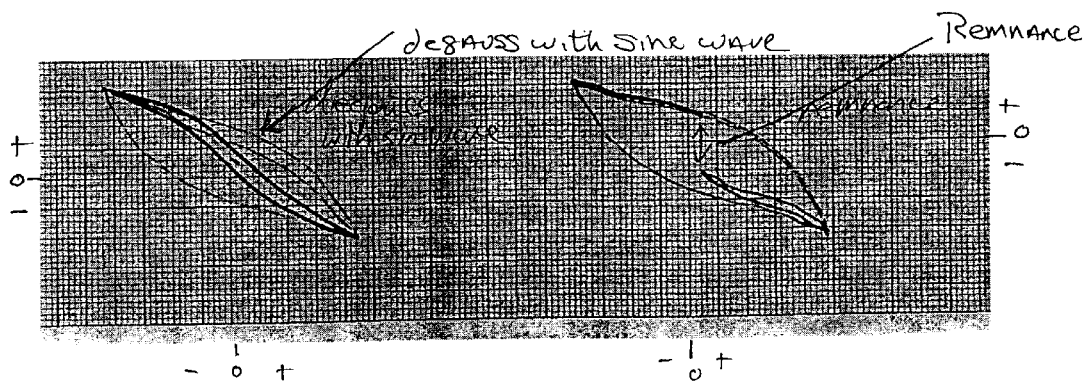
FIG. 23 is a plot of remnmance loop for an electromagnetic unit of the present invention having the dimensions, in micrometers, of 1600×50×5 with an applied current of 20 milliamps when turned off. When ramped down using a sinusoidal current the field of the device reduces, preferably to near zero or zero, as shown on the left.

Output of data is exemplified by FIG. 21, which shows the plot of field v. distance for the 400×50×5 core. Also included in the plots is the calculated total field and the calculated z component field, showing that most of the field is along the z axis above the end of the core. The measured field is smaller by about a factor of two from the calculated result, which may be due to process offsets in the geometry of the finished devices. As shown in FIG. 22, the center of the device reaches a saturation at about 50 milliamps of current, as shown by the knee in the curve, but the field continues to climb with increasing current as the pole density at the end of the core continues to increase. FIG. 23 shows remnance of the devices. The devices have remnance if taken from an on state directly to zero current. The device with the larges remnance is the 1600 micrometer core, presumably because it has the lowest demag field. The remnance loop of the device is provided on the right of FIG. 23 with 20 mA of current when turned off. When ramped down using sinusoidal current, as shown on the left side of FIG. 23, the field of the device goes to zero.

Figure 25:
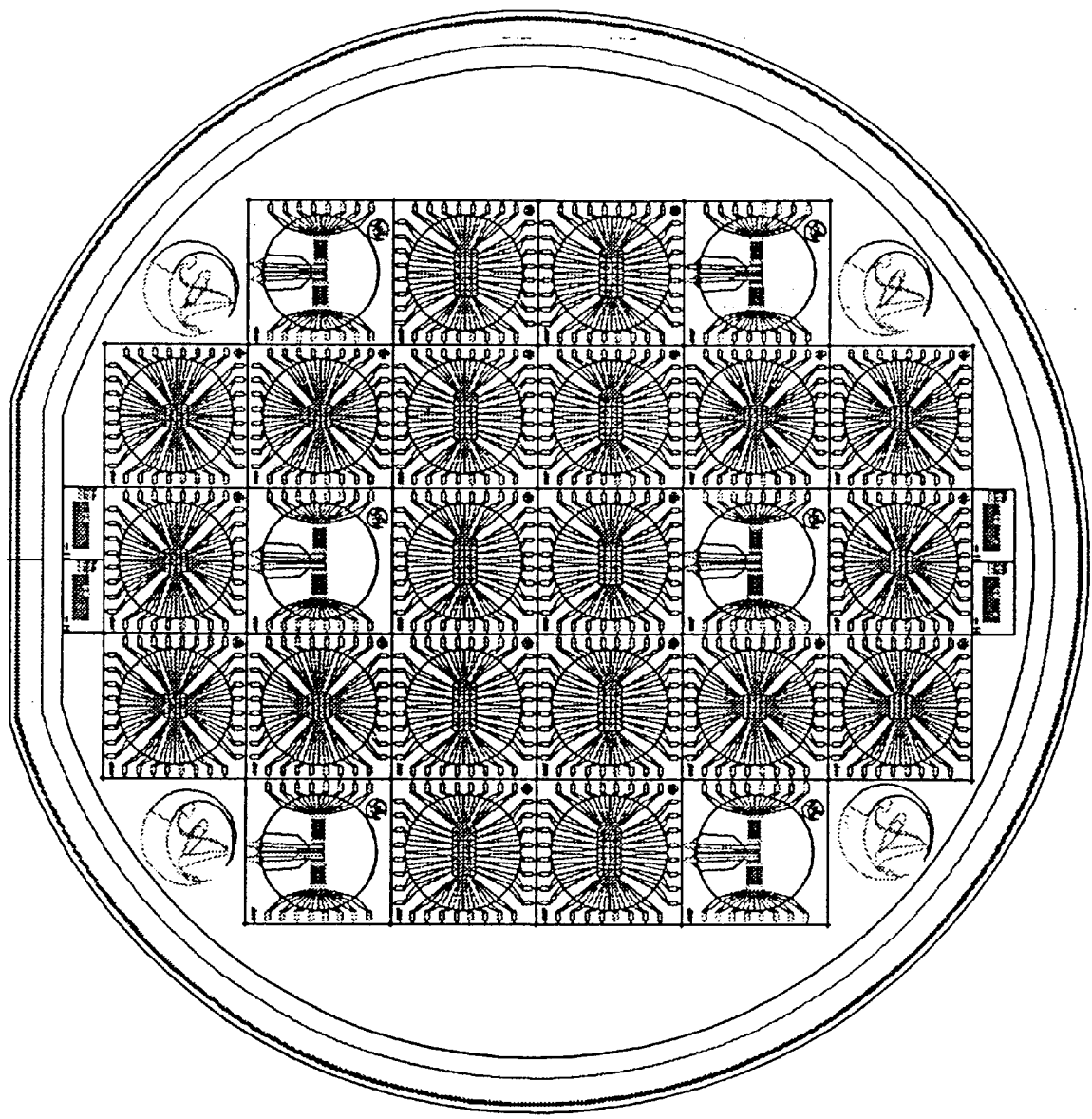
FIG. 25 depicts a wafer having a plurality of differing chips of the present invention thereon, which is preferably a wafer of about 3 inches in diameter.

The devices can be manufactured in chip format having appropriate contacts. For example, two chip configurations are shown in FIG. 24A and FIG. 24B, one chip having a plurality of smaller horizontal units in FIG. 24A and the other chip having a plurality of larger horizontal units in FIG. 24B. As shown in FIG. 25, a variety of such chips can be provided on a wafer.

Figure 26:
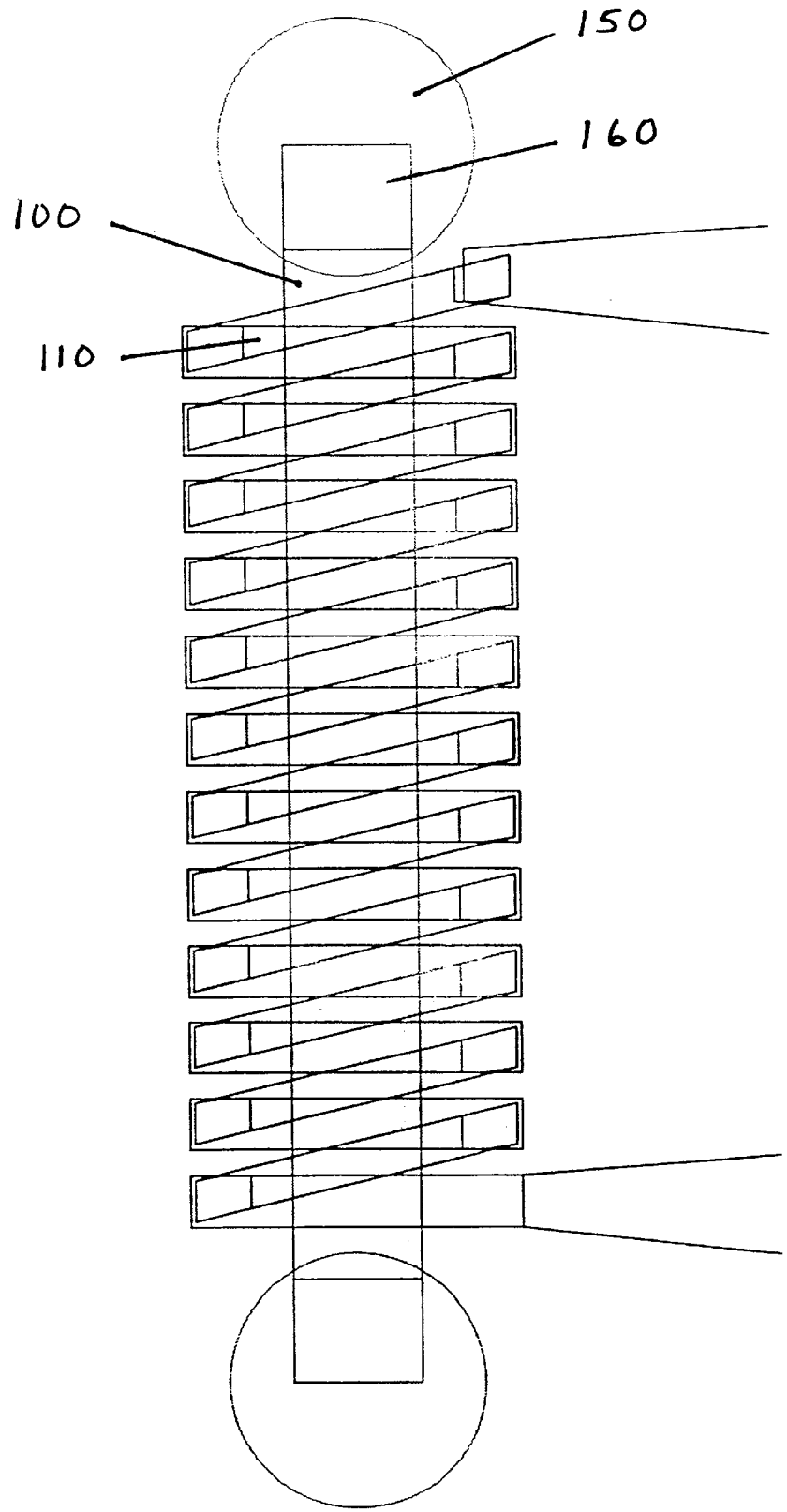
FIG. 26 depicts one aspect of an electromagnetic chip of the present invention having core extension structures and dips.

FIG. 26 shows a horizontal unit of the present invention with square core end structures and dips in the surface of the chip. The dips can be of any appropriate size or shape, but preferably have a depth of about the diameter of the particles or aggregates thereof being used in the methods of the present invention. The dips can be of any appropriate shape, but are preferably circular or oblong in shape. Preferred depths of dips are between about 0.5 micrometers to about 10 micrometers. Preferred widths of dips are between about 5 micrometers and about 500 micrometers, more preferably between about 20 micrometers and about 200 micrometers. The dips can be made using any appropriate method, such as chemical or laser etching or mechanical devices and methods that result in the formation of depressions or dips, such as the use of force or machining devices. In operation, the dips allow for particles attracted to the electromagnetic units, particularly at the poles, to be nested within the dips. During fluid flow, the dips can act to protect the particles from being washed away. In addition, the dips can function to strengthen the magnetic field at that location, particularly at a pole of an electromagnetic unit, by decreasing the distance between the electromagnetic unit and the surface of the chip. The dips can also act to make the magnetic field more uniform in nature.

Figure 27:
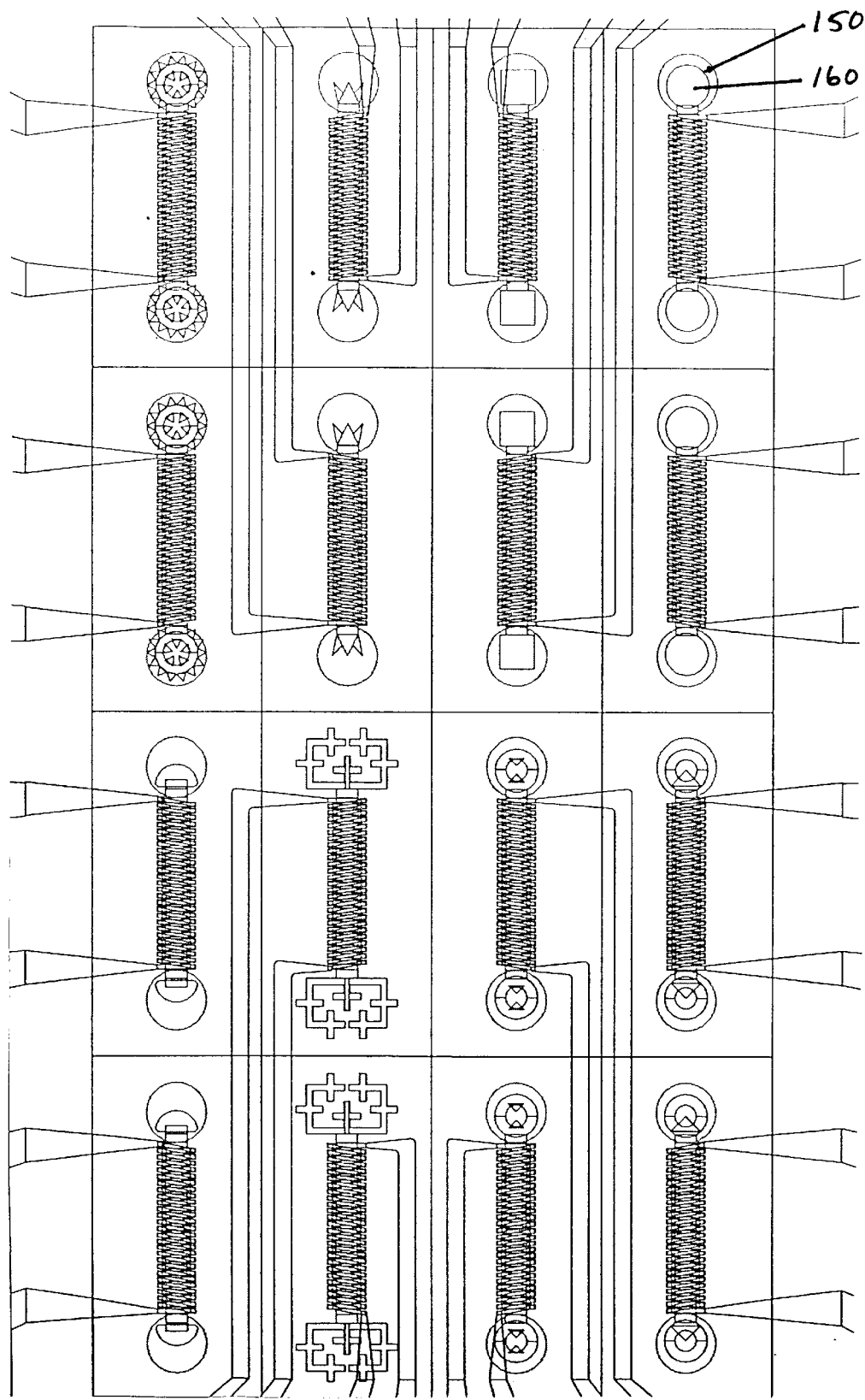
FIG. 27 depicts a variety of electromagnetic chips that have a variety of core extension structures (160) and dips (150).
Figure 28:
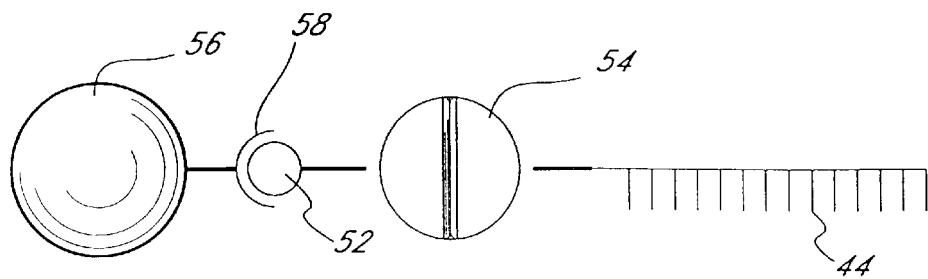
FIG. 28 depicts a target molecule linked to a magnetic particle.

The shape of the core end structures can influence the strength of the field at the ends of the core. As discussed previously, it is desirable to have the magnetic field generated by the horizontal unit to be relatively diffuse. The magnetic field will be stronger at the poles, but the core end structures can act to diffuse the strength of the field at the poles. FIG. 27 provides a variety of core end structures that can act to diffuse the magnetic field at the poles of the horizontal units. These core end structures are preferably made using core material and can be made using the procedures used to make cores by depositing core material in the configuration shown. The dips, while desirable, are optional structures.

One preferred method of making a horizontal electromagnetic unit is as follows. A surface is provided upon which a plurality of substantially parallel lines of conductive material such as gold are laid down by the use of sputtering and a mask. These substantially parallel lines of conductive material will form the bottom of the coil of a horizontal electromagnetic unit of the present invention. A layer of insulating material such as $SiO_2$ is deposited over these parallel lines of conductive material. A core of magnetizable material is deposited on the insulating material over the substantially parallel lines of conductive materials such that the core is substantially perpendicular to the substantially parallel lines of conductive material. The core is preferably made of CoTzZr and can be of any shape, but preferably form a bar, optionally with beveled edges such as forming a rounded top configuration, much like a bar of gold. Preferably, the ends of the core have terminal structures such that when in operation the magnetic field is relatively diffuse and has a relatively long working range. An additional layer of insulating material is deposited over the core and optionally over the substantially parallel lines of conductive material.

Both of the ends of each of the substantially parallel conductive lines forming the bottom of the coil are exposed by masked etching, such as by acid etching to form shafts, leaving insulating material between the shafts and the core. The shafts are filled with conducting material, such as gold to form vertical risers from the ends of the substantially parallel conductive lines. The top ends of the vertical risers are then connected via transverse conducting lines by masking and deposition of conductive material, such as gold via sputtering, to form a coil that can conduct a current. Preferably, the transverse conducting lines are in a diagonal configuration to connect the ends of the bottom tracings to form a coil. An additional layer of insulating material is deposited such that a substantially flat surface is obtained. The surface can be further finished using various processes, such as polishing. Additionally, dips can be formed over the ends of the core using appropriate methods, such as masked chemical etching.

The coils can be connected to conductive bumps, such as gold bumps, using lines of conductive material that connect the coil to the bumps. These lines of conductive material, such as gold, can be made using appropriate materials and methods, such as masked sputtering. The bumps can be used to electrically connect a source of current to the coil.

When energized, the coil acts upon the core to magnetize the core, which in turn forms a magnetic field. The magnetic fields generated can be measured using a variety of methods, such as a MR head. Different materials, shapes and dimensions of the elements can be made to determine appropriate materials and dimensions for intended purposes for the electromagnetic units, such as methods of the present invention.

Example 3

Method for Detecting Binding Reactions

The following example refers one aspect of the electromagnetic chips of the present invention. In particular, this example describes methods for detecting reactions using electromagnetic chips having micro-electromagnetic units.

FIG. 28 through FIG. 37 illustrate methods for using an electromagnetic biochip shown in FIG. 4 to manipulating molecules, of chemical, biological, pharmaceutical or other types, according to the present invention. These methods include following steps:

a). Constructing an individually addressable micro-electromagnetic array chip 10 such as shown in FIG. 4.

b) Forming a functional layer 42 on to the surface of the above chip. This functional layer is used for immobilizing ligand molecules.

As described above this layer 42 may be formed by direct chemical modification of the surface of the insulation layer 32 or by polymer coating or by introducing affinity molecules or reactive functional groups. The layer may be a functional hydrophilic or hydrophobic molecular monolayer, hydrophilic or hydrophobic membrane, functional hydrophilic/hydrophobic gel, polymer layer, porous or non-porous layer or the composite of these materials.

c) Magnetic modification or loading of ligand molecules that will be subsequently immobilized on the functional layer 42.

d) Controlling electric current in individual traces 18, 30 to create magnetic fields at desired micro-electromagnetic units so that the magnetically modified or loaded ligand molecules are drawn to and immobilized at desired micro-locations on the functional layer 42. This will form affinity binding regions required by various assays on the chip surfaces.

There are various methods for manipulating and immobilizing the ligand molecules at specific regions through the application of magnetic field. For example, the ligand molecules 44 may be linked onto a paramagnetic bead 56 through a cleavable linker 54. Thus, the ligand molecules can be transported, manipulated and released at specific regions by taking advantage of forces acting on the paramagnetic beads 56 due to magnetic field generated by the electromagnetic biochip. The paramagnetic microbeads 56 may range in size from less than 100 nm to more than 100 micrometer. They can be manufactured by methods known in the art or can be purchased from Companies such as Dynal or Seradyn. The cleavable linkers 54 may be photocleavable, heat cleavable, enzyme cleavable or cleavable by a specific chemical reaction. The connection between the cleavable linker 54 and the paramagnetic microbead 56 may be made by a covalent bond or by means of bioaffinity between an end functional group 52 of the cleavable linker and a receptor group 58 of paramagnetic micro-bead 56.

For example, the overall assembly may be as follows:
Ligand (44) cleavable linker (54) biotin (52)-streptavidin (58) paramagnetic microbead (56)
Here, biotin-streptavidin binding serves as the connection between cleavable linker and paramagnetic microbeads. Such a molecular assembly can be used as a general format for modifying any ligand molecules with paramagnetic microbeads using the following steps. First, streptavidin molecules are coupled to the surfaces of paramagnetic microbeads using the methods known to those skilled in the art (typically, paramagnetic microbeads have a surface of a polystyrene layer having carboxyl or amino groups). Alternatively, streptavidin-coated paramagnetic microbeads may be purchased from manufacturers. Secondly, cleavable linker biotin molecular-complexes are prepared. These two steps are applicable to magnetic modification of any types of ligand molecules. Thirdly, specific ligand molecules are coupled to cleavable linkers through, for example, covalent bonding. Finally, the overall molecular assembly is formed by incubating streptavidin-coated paramagnetic beads with ligand-cleavable linker-biotin molecular complexes to allow biotin-streptavidin binding reaction to take place.

For immobilizing ligand molecules, the magnetic field generated by energized magnetic units will exert magnetic forces on the paramagnetic microbead 56 which will bring the overall molecular assembly into contact with the surface of the biochip above the energized unit. The cleavable linker can then be cleaved so that the microbeads 56 can be removed after the unit is switched off. As explained below, a fluid wash or externally applied magnetic force can then be used to remove all the microbeads leaving the ligand molecules immobilized on the functional layer 42.

Figure 29:
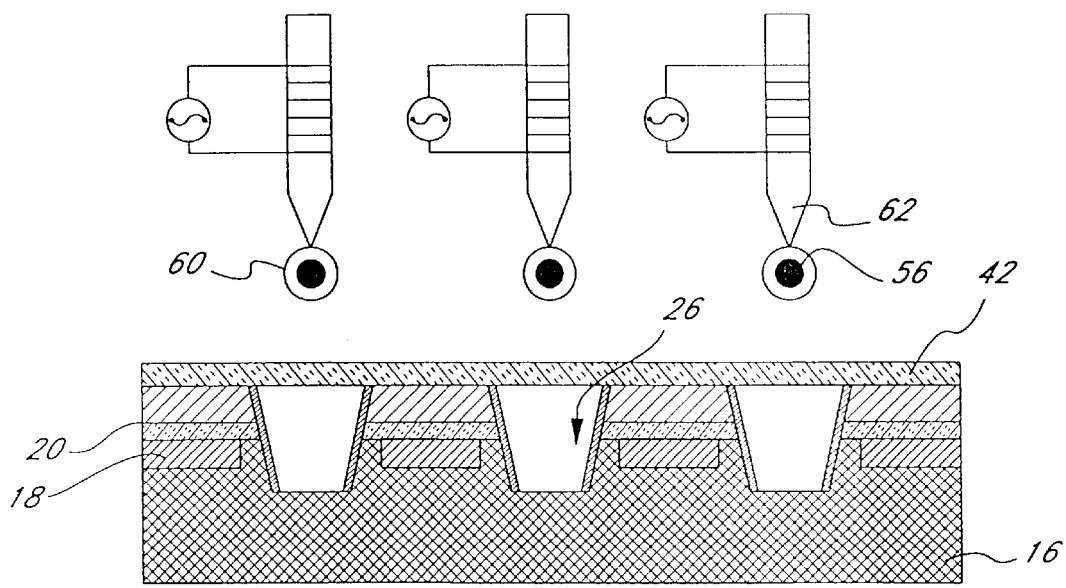
FIG. 29 depicts the use of magnetic dispensers to pick up frozen micro-particles containing ligand molecules and magnetic particles in one aspect of the present invention.
Figure 30:
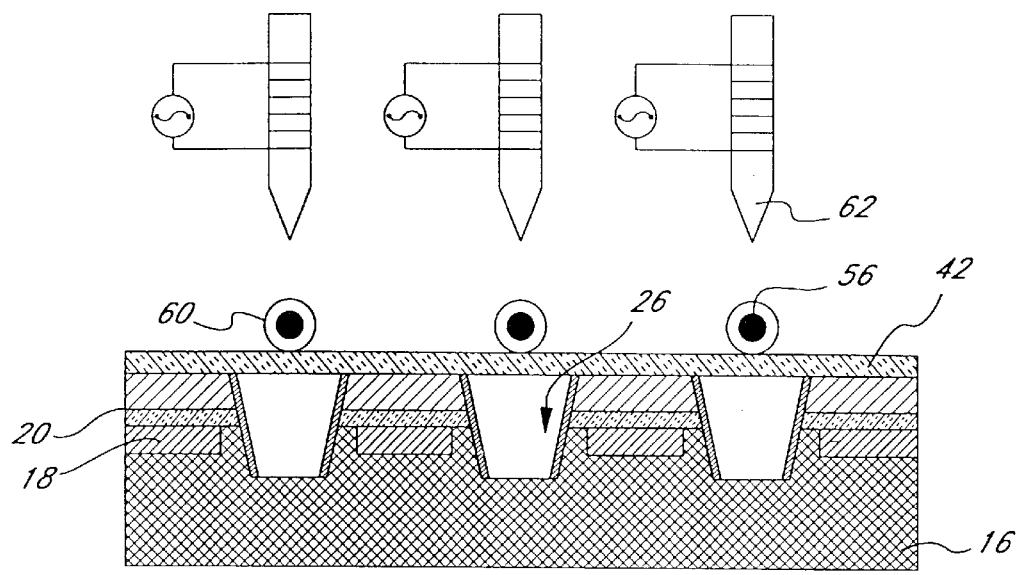
FIG. 30 depicts the release of the frozen micro-particles of FIG. 29 on the surface of a biochip of the present invention in one aspect of the present invention. Although shown in a vertical configuration, the depicted electromagnetic units can optionally be provided independently in a horizontal configuration.
Figure 31:
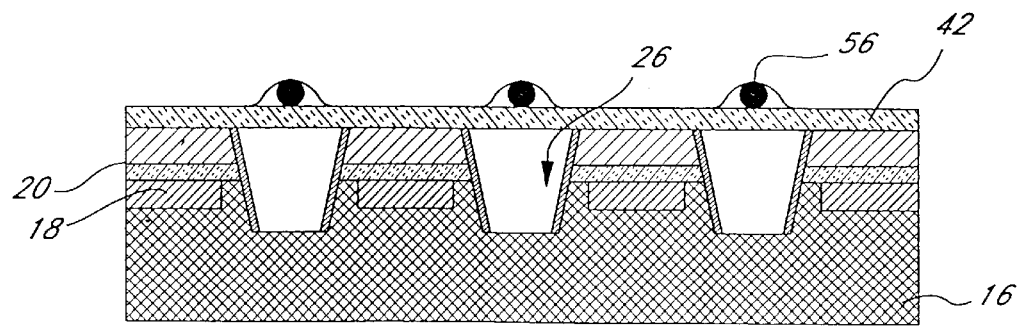
FIG. 31 depicts the melting of the frozen micro-particles (containing ligand molecules and magnetic particles) of FIG. 30. Although shown in a vertical configuration, the depicted electromagnetic units can optionally be provided independently in a horizontal configuration.

Another method for magnetically loading ligands is to mix the solution containing ligand with paramagnetic microbeads and then rapidly freezes them to form solid microparticles 60 (usually less than one millimeter in diameter) containing the ligands and paramagnetic micro-beads. The solidified micro-particles 60 prepared from different samples may be stored in a freezer for future applications. Directed transportation of such solidified micro-particles to the chip can be achieved by a three-dimensional precision robotic arm equipped with a specially designed magnetic micro-particle dispenser 62. After the solidified microparticles are carried to predetermined positions above the designated region on the chip, the micro-particles are released and immobilized (FIG. 28) by controlling the electric current at the designated micro-electromagnetic unit so that the magnetic field on the chip region is stronger than the field on dispenser head 62. Thus, the solidified microparticles 60 are released onto the functional layer 42 of the chip 10 at the designated regions (FIG. 29). After melting the solid micro-particles 60, the ligand molecules are immobilized on the designated chip regions (FIG. 30). Such steps have additional advantages as follows: the cross contamination between ligand molecules by the magnetic dispenser 62 is reduced to minimum without cleaning the dispenser head after each delivery. After the immobilization of ligand molecules on the chip surfaces is complete, the magnetic microbeads 56 may be removed from the chip by additional magnetic forces above the chip surface or by fluidic wash (FIG. 31).

The affinity binding area on each micro-electromagnetic unit on the chip may have characteristic dimensions between 0.1 micrometer to 5 mm (width and length for rectangular shape, or diameter for circle shape). The size of the binding area depends on the dimensions of each magnetic-core 26 and whether multiple cores are energized and the polarities of the energized cores. The exact dimensions of the affinity binding areas can also be altered by controlling the functional layer 42, for example, the functional layer 42 can be deposited under photolithographic control (as opposed uniformly covering the chip).

e. Target molecules 62 are labeled (for example, with a fluorophore 64) and connected onto magnetic microbeads 56.

To use the individually addressable micro-electromagnetic chips described in this invention to manipulate the target molecules 62, these molecules need first to be magnetically modified.

There are also various methods to magnetically modify the target molecules. For example, the target molecules 62 may be linked onto a paramagnetic bead 56 through a cleavable linker 54 so that the target molecules may be manipulated and moved to the target area by applying magnetic fields. The connection of cleavable linker 54 and a paramagnetic microbead 56 may be achieved by covalent bonds or by affinity between the end functional group 52 of the cleavable linker and the functional group or receptor 56 of paramagnetic microbead. For example, the connection may be structures as (FIG. 32):

Target molecule cleavable linker biotin-streptavidin paramagnetic microbead

Such assembly can be formed using the similar procedures to those described above for forming ligand-paramagnetic microbead assembly.

f. The target molecules 62 that have been linked to paramagnetic beads 56 are placed in the fluidic chamber 46 and are brought into contact with the ligand molecules 44 immobilized on biochip surfaces by controlling magnetic fields.

g. In the case of column/row unit arrays, energizing microelectromagnetic units using the electric current flowing patterns such as those illustrated in FIG. 33 and FIG. 34

Figure 35:
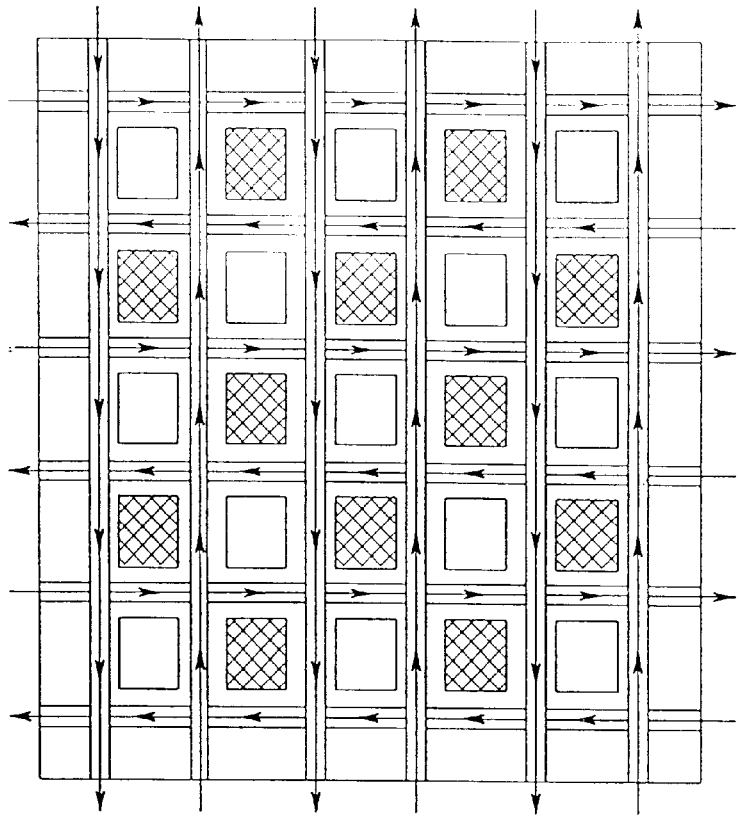
FIG. 35 depicts a different pattern of electric current flow through the conductive traces of an electromagnetic chip in one aspect of the present invention. This current flow pattern allows for energizing micro-electromagnetic units that are optionally not energized in FIG. 34. Although shown in a vertical configuration, the depicted electromagnetic units can optionally be provided independently in a horizontal configuration.

This allows alternative turn-on and turn-off of magnetic fields at the microelectromagnetic units. Thirteen out of 25 units are energized in FIG. 33 while other 12 units are energized in FIG. 34. Thus, the magnetic field generated at individual micro-electromagnetic units attracts the magnetically-modified target molecules 62 and moves them close to the designated ligand affinity binding regions. By changing the magnetic patterns sequentially, every electromagnetic unit can attract and concentrate the target molecules 62 from its vicinity in solutions. Therefore, affinity binding reactions between target molecules 62 and the ligand molecules 44 are brought about (FIG. 35).

Figure 32:
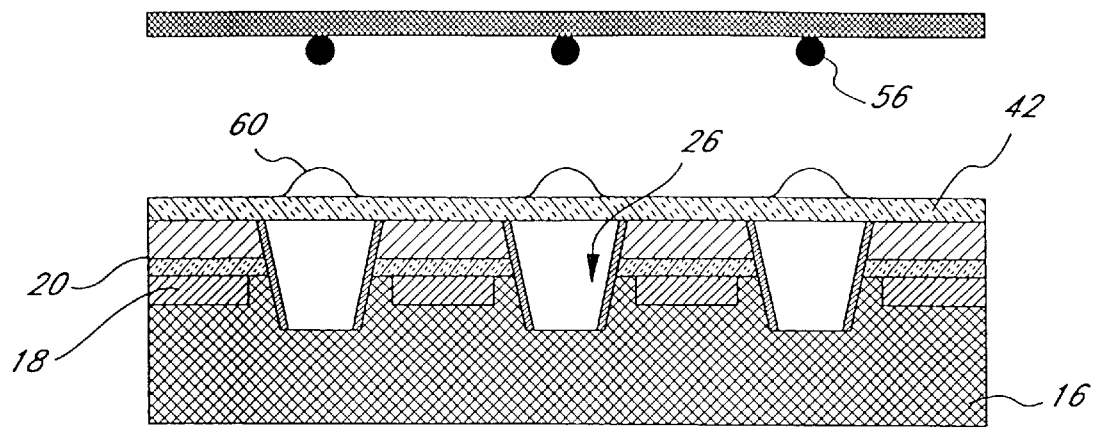
FIG. 32 depicts the removal of magnetic particles from the ligand molecules of FIG. 31. Although shown in a vertical configuration, the depicted electromagnetic units can optionally be provided independently in a horizontal configuration.
Figure 33:
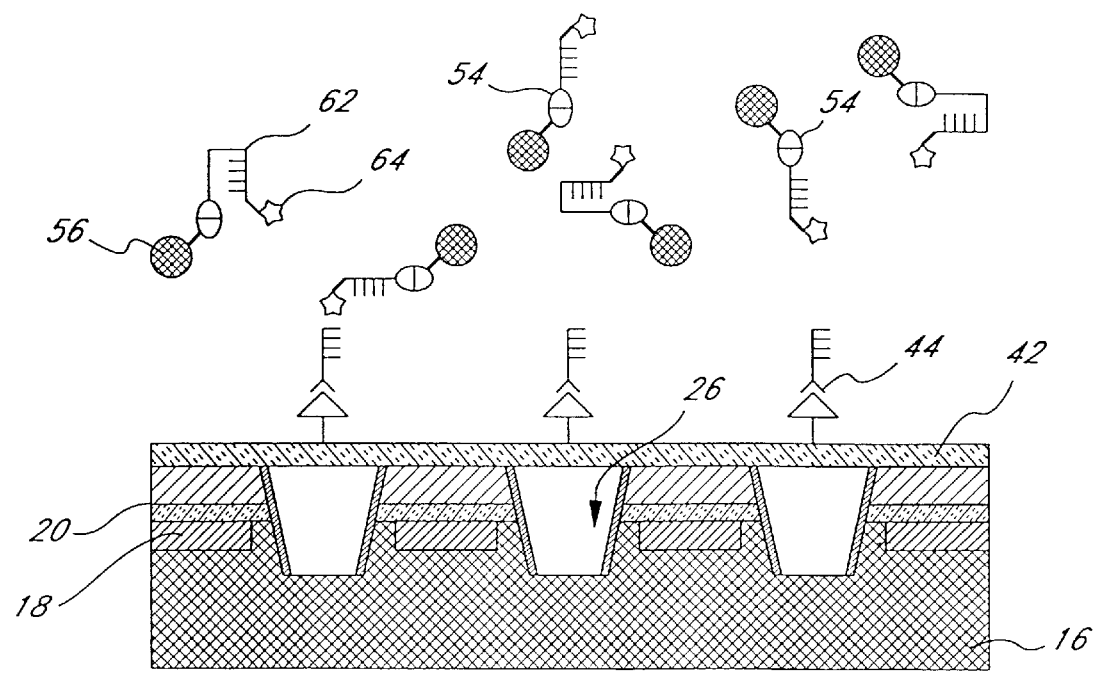
FIG. 33 depicts the random movement of magnetically-modified target molecules above the surface of a biochip of one aspect of the present invention. Although shown in a vertical configuration, the depicted electromagnetic units can optionally be provided independently in a horizontal configuration.
Figure 34:
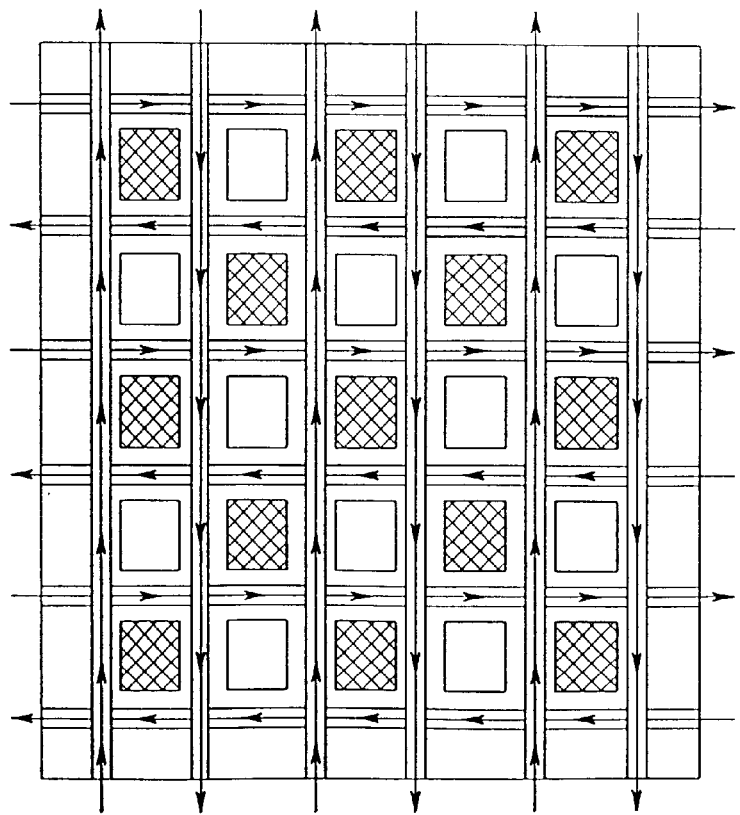
FIG. 34 depicts a pattern of electric current flow through the conductive traces of an electromagnetic chip for energizing a group of micro-electromagnetic units in one aspect of the present invention (for example, magnetizing a group of magnetic cores). Although shown in a vertical configuration, the depicted electromagnetic units can optionally be provided independently in a horizontal configuration.

When the magnetically-modified target molecules 62 are introduced onto the electromagnetic biochips for analyses, the motion of the target molecules 62 is at first controlled by random diffusion (FIG. 32). The directed movement of the sample molecules to all the micro-electromagnetic units is achieved by applying magnetic fields through alternatively turn-on and turn-off of the magnetic field at all the units as illustrated in FIG. 33 and FIG. 34. According to the specific assays, directed movement of target molecules 62 to one or a number of selected micro-electromagnetic units can also be achieved by selectively switching on these units. Under the influence of the magnetic field generated by the selectively-addressed micro-electromagnetic unit, the magnetically-modified target molecules 62 can be caused to rapidly move towards the biochip surface, and to undergo the affinity binding reactions (or other reactions) with the ligand molecules 44 immobilized in the designated unit regions. (FIG. 35).

h. In a final step, the target molecules 62 (or their reaction products) are separated from the magnetic microbeads 56, which are then removed.

Figure 36:
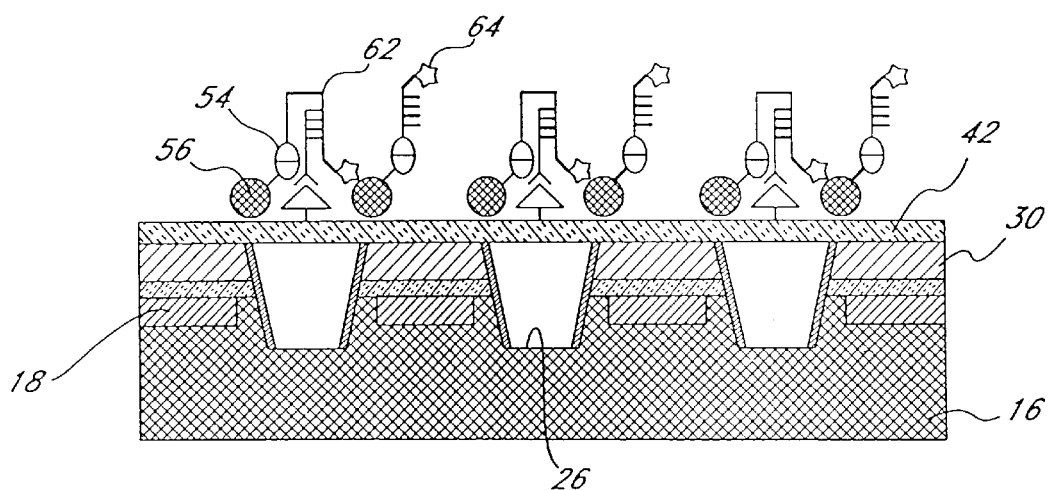
FIG. 36 depicts a schematic representation of formation of complexes that include the magnetic particles from the target molecules after the target molecules have undergone reaction with ligands at the surface of the biochip in one aspect of the present invention. Although shown in a vertical configuration, the depicted electromagnetic units can optionally be provided independently in a horizontal configuration.
Figure 37:
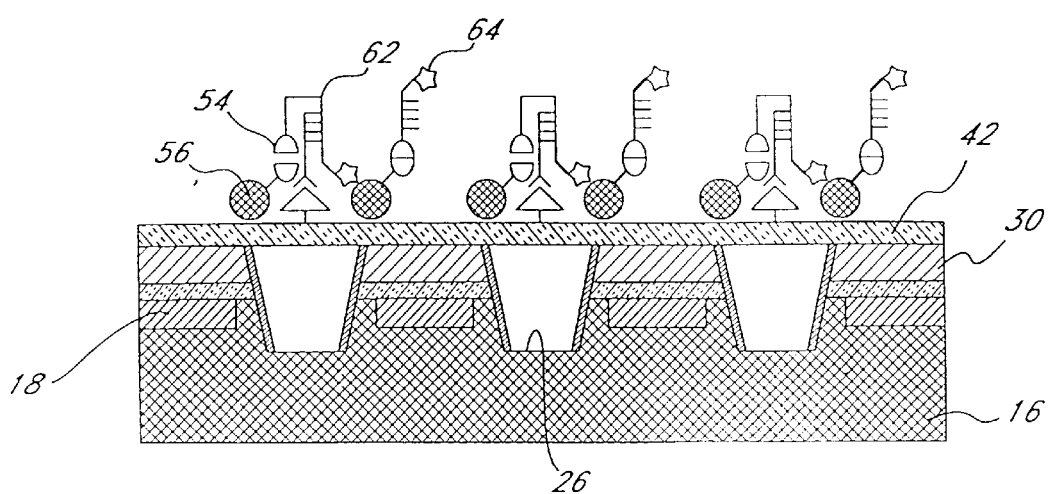
FIG. 37 depicts a schematic representation of cleaving the magnetic particles from the target molecules after the target molecules have undergone reaction with ligands at the surface of the biochip in one aspect of the present invention. Although shown in a vertical configuration, the depicted electromagnetic units can optionally be provided independently in a horizontal configuration.

Separation of target molecules 62 from magnetic microbeads 56 can be accomplished by photocleavage, enzymatic digestion, chemical cleavage, etc. of the cleavable linker 54 between target molecule 62 and microbeads 56 (FIG. 36 and FIG. 37). The magnetic microbeads 56 can be removed from the chip surface by the application of additional magnetic forces above the chip (not effective with a closed fluid chamber 46) or may be washed away by liquid flowing through the chamber 46.

In above-mentioned method, the ligands and target molecules can be any type of molecule (for example, biological, pharmaceutical, or any other chemical entity). The methods in this invention can be applied for determination of specific DNA sequences by hybridization, binding assays of antigen-antibody reactions and drug screening (for example, binding of drug molecules or potential drug compounds to specific receptors). For example, a library of candidate drug compounds could be prepared as ligand molecules and localized at predetermined locations on the functional layer 42. Biological receptors could be isolated from cells or produced by genetic engineering methods and fluorescently labeled. The receptors are then either specifically localized on the functional layer 42 to correspond with candidate compounds. After a washing step, any candidate compounds that lit up with the label is a compound that shows promise of interacting with the biological receptor. Therefore, this invention can be applied to perform controlled biochemical reactions, biochemical detection and clinical diagnostic tests. In addition, special organic reactions to assemble complex large molecules can also be achieved.

When the above-described methods are used for DNA hybridization, after step h, non-specifically hybridized DNA molecules can be removed by stringent control of the binding conditions, such as hybridization buffer, temperature etc. This leaves the DNA molecules showing high affinity left hybridized to the ligand molecules where they can be detected by fluorescence, etc.

When the above-described methods are used for antigen-antibody interaction, after step h, non-specifically bound antigen or antibody molecules can be removed by stringent buffer washing conditions and whereas the specific bound antigen or antibody molecules remain on the affinity binding area.

When the above-described methods are used for biological analyses, the detection and quantification of the analytical results may be obtained using several detection methods, such as optical signals (either through measurement of absorbance or fluorescence), chemiluminescent or electro-chemiluminescent detection, electrochemical detection, and detection of radioactive labels.

Optical detection can be realized by detecting the fluorophore 64 carried by the target molecules, which is excited by laser light source. Another optical detection method utilizes fluorophore- tagged probes or secondary antibodies that specifically bind to the target molecules, and then the florescence are induced by laser light source. Fluorescence resonance energy transfer can also be used to detect the close proximity of the ligand 44 to the target molecule 62. The details about fluorescence resonance energy transfer can be found in the article by Ju et al., Fluorescence energy transfer dye-labeled primers for DNA sequencing and analysis in *Proc. Natl. Acad. Sci. USA*, 92:4347–4351, and in references cited in the article. The following is a practical example for controlled DNA molecule operation that uses the methods of this invention.

First, an individually addressable micro-electromagnetic array chip is constructed according to the methods described in this invention. The surface of the chip is coated with a layer of high molecular polymer for DNA probe immobilization.

The paramagnetic microbeads are added into the solution that contains DNA probes and the solution mixtures are then quickly frozen to form solid micro-particles. The microparticles are transported onto the top of the designated regions (micro-electromagnetic units) of the biochip through a precision robot equipped with a magnetic-dispenser. A plurality of different probes is immobilized on different regions. Potentially each chip could have as many different probes as there are individual magnetic units on the chip. A stronger magnetic field than that of the magnetic dispenser is generated on the unit of the biochip by connecting electric currents to the selected units. The probe mixed microparticles are released on the functional layer of the specific units on the biochip. When the solid microparticles are melt, DNA probes in the liquid become immobilized at the designated unit (region) on the biochip. Then the free magnetic microbeads are removed by an additional magnetic field applied above the surface of the biochip or washed away fludically. Thus affinity binding regions on the biochip surface are formed.

The target DNA molecules are labeled (e.g., with a fluorophore or radioactive probe) and are linked to the one-ends of photocleavable linker molecules. On the other end of the linkers, there are biotin molecules. Streptavidin molecules are immobilized on the surface of the magnetic microbeads. Then, solutions containing target DNA-linker-biotin complexes and streptavidin-coated magnetic microbeads are mixed together. The target DNA molecules are linked to magnetic microbeads by biotin-streptavidin interaction.

DNA target photocleavable linker biotin-streptavidin magnetic microbeads.

The solution containing magnetically-modified target DNA molecules is then placed in the liquid chamber on the biochip. The micro-electromagnetic units are alternatively energized to produce magnetic fields in each unit on the chip. The target DNA molecules that are modified by magnetic microbeads are moved to the probe DNA molecules that have been immobilized on the chip surfaces. Since all the electromagnetic units are energized, target DNA molecules are brought into contact with all DNA probes. The target DNA molecules, therefore, undergo hybridization reaction with the probe molecules on the affinity binding regions under the pre-selected hybridization conditions.

Any probes that hybridize to the target DNA molecules can be detected by fluorescence, luminescence or radiation depending on the label used on the target molecules. This way a given DNA target can be rapidly screened against a plurality of DNA probes and the results rapidly and automatically quantitated. If the magnetic microbeads interfere with detection, they can be separated from target DNA molecules, for example, by irradiation with 250 nm–750 nm light in the case of a photocleavable linker. The light cleaves the photocleavable linker to disconnect DNA and magnetic beads. The free magnetic beads can then be removed from reaction regions on the chip by additional magnetic forces or washing. Afterwards, the chip can be subjected to melting conditions to remove the hybridized target DNA and be reused for a second and for subsequent target DNAs.

The inventors believe the above-described examples show preferred approaches for utilizing this invention. However, the described parameters such as dimensions, materials, geometries, methods, protocols, temperatures, concentrations and time should not be considered the limits of this invention. In addition to the equivalents of the claimed elements, obvious substitutions now or later known to one with ordinary skill in the art are defined to be within the scope of the defined elements. The claims are thus to be understood to include what is specifically illustrated and described above, and what can be obviously substituted. The illustrated embodiment has been set forth only for the purposes of example and that should not be taken as limiting the invention. Therefore, it is to be understood that, within the scope of the appended claims, the invention may be practiced other than as specifically described herein.

Example 4

Traveling Magnetic Waves Using Horizontal Units

This example addresses a particular application of traveling wave magnetophoresis. This method can use a variety of electromagnetic units, but the horizontal units of the present invention are described herein.

An electromagnetic chip such as that in FIG. 24A and FIG. 24B is provided in a chambered configuration with appropriate circuitry to allow for traveling wave magnetophoresis to take place. On a functional layer above the electromagnetic units is provided immobilized antibodies specific for seven different lymphoma cells and one for a normal white blood cell such as a B-cell, one for each of the eight electromagnetic units in the traveling wave magentophoresis unit. A different antibody preparation is independently located above each of the eight electromagnetic units. A sample including blood is contacted with magnetic particles that have immobilized thereon antibodies that bind with a surface antigen found on all white blood cells, normal or lymphoma. This mixture is allowed to incubate under conditions that allow the white blood cells in the sample to bind with the particles having the antibody thereon. Optionally, an additional sample solution is added to the sample to aid in processing of the sample. For example, a solution that lysis red blood cells can be used, preferably a solution that preferentially lyses red blood cells relative to white blood cells, and more preferably does not substantially interfere with dielectrophoresis (see, for example, U.S. patent application Ser. No. 09/686,737 filed Oct. 10, 2000, entitled "Compositions and Methods for Separation of Moieties on Chips" and naming JunQuan Xu, Xiaobo Wang, Jing Cheng, Weiping Yang, and Lei Wu as inventors. A sample, a sample solution, and, optionally, additional solutions, buffers, preparations, or reagents, can be added to a chamber by any convenient means, such as transfer with a pipette, injection with a syringe, gravity flow through a conduit, such as tygon tubing, etc. Preferably a sample, a sample solution, and optionally other solutions, buffers, preparations, or reagents are added to a chamber in a continuous flow mode, in which a continuous stream of fluid is injected or pumped into at least one inlet port, and non-retained sample components and fluids exit the chamber via at least one outlet port.

A sample solution can be added to a sample before a sample is added to a chamber. A sample and sample solution can be incubated together for any length of time before adding the sample solution-sample mixture to a chamber for separation, from less than one second to several days. Sample-sample solution mixing can also occur in a conduit that leads to the chamber, as shown in. Alternatively, a sample can be added to a chamber and a sample solution can be added to the chamber subsequently. It is also possible to add a sample solution to a chamber before adding the sample to a chamber.

Where binding partners such as magnetic microparticles are used in the methods of the present invention, the binding partners can be provided in the sample solution, or separately. If the binding partners are added to the sample separately, they can be added before, after, or at the same time as the sample solution.

A sample solution can be added to a sample before a sample is deposited on an electromagnetic chip or in a chamber comprising an electromagnetic chip. The sample and sample solution can be incubated together for any length of time before adding the sample solution-sample mixture to a chamber for separation, from less than one second to several days. Sample-sample solution mixing can occur in a conduit that leads to the chamber. Alternatively, a sample can be added to a chamber and a sample solution can be added to the chamber subsequently. It is also possible to add a sample solution to a chamber before adding the sample to a chamber.

In one aspect of the present invention, a preparation of magnetic particles is added to a sample and allowed to incubate with the sample for a period of time before the magnetic separation process. The period of time is preferably from minutes to days. The addition of a preparation of magnetic particles to a sample can occur before, after, or at the same time as the addition of a solution that selectively lysis red blood cells.

A sample, a sample solution, and, optionally, solutions, buffers, preparations, or reagents, can be added to a chamber by any convenient means, such as transfer with a pipette, injection with a syringe, gravity flow through a conduit, such as tygon tubing, etc. Preferably a blood sample, a preparation of magnetic particles, a solution that selectively lysis red blood cells, and optionally other solutions, buffers, preparations, or reagents are added to a chamber in a continuous flow mode, in which a continuous stream of fluid is injected or pumped into at least one inlet port, and non-retained sample components and fluids exit the chamber via at least one outlet port.

One or more preparations that include microparticles can be added to the sample through one or more conduits, although this is not a requirement of the present invention. For example, one or more preparations that comprise microparticles can be added to the sample and after a period of time, the sample that has incubated with the microparticles can be added to the chamber. Alternatively, the microparticles can contact the sample in one or more conduits of the chamber, and the sample is mixed with the preparation comprising microparticles as they flow into the chamber. In another aspect, one or more preparations that comprise microparticles can be added to the chamber via one or more conduits before, after, or concurrent with the addition of sample to the chamber. If more that one preparation that comprises microparticles is used in a method of the present invention, the preparations can be added separately or together.

Figure 38:
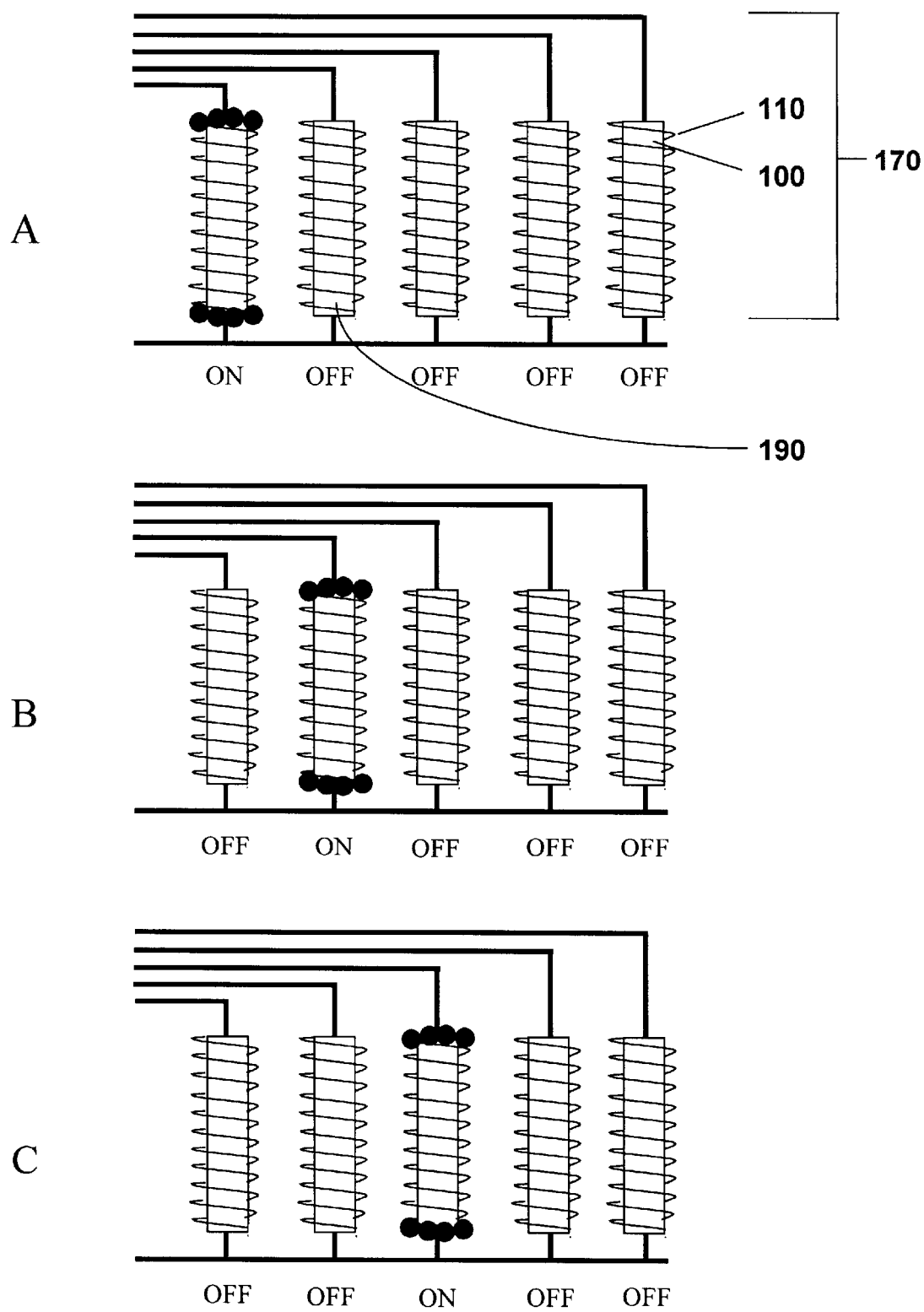
FIG. 38 depicts one aspect of traveling wave magentophoresis of the present invention using a traveling wave megnetophoresis device (170) to move magnetic particles (180) using micro-electromagnetic units (190).
Figure 39D:
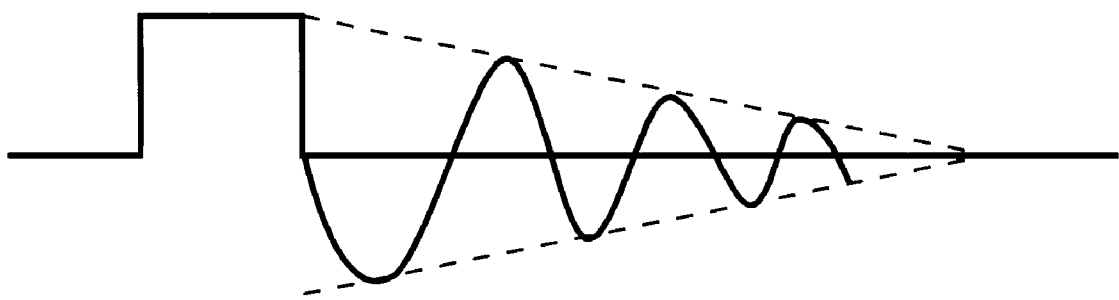
FIG. 39D depicts sinusoidal current in a micro-electromagentic unit of the present invention energized with DC current.

The sample is subjected to traveling wave magnetophoresis on a chip (FIG. 38A, FIG. 38B and FIG. 38C) optionally using a particle switch (FIG. 39A). White blood cells with particles bound thereto travel along the array of antibodies bound to the functional layer and bind to the loci where the antibody bound to the functional layer specifically binds with the white blood cell. Preferred antibodies on the array are those that can identify populations of lymphocytes, such as T-cells, B-cells, macrophages, neutrophils, eocinophils etc. The distribution of the type and amount of these types of cells provides valuable information relating the health state of a subject from which the sample was obtained. For example, the presence and type of lymphoma, progression of treatments or therapies for autoimmune disease states or conditions, including HIV infection or AIDS or related conditions, or for other disease states or conditions, including septicemia. The progression of treatment for such disease states or conditions can also be monitored using these methods, such as the modulation of CD4+ cell populations in HIV infected individuals undergoing therapy or treatment.

Other types of antibodies can be used, such as those directed against cancer antigens, particularly those present on the surface of metatstatic cells, such as breast cancer cells, lung cancer cells, testicular cancer cells, prostate cancer cells and other types of cancer cells as well. The presence of such cells, such as determined by their localization on a chip by a method of the present invention, is prognostic or diagnostic of such disease states or conditions. Other antibodies, such as those against bacteria, parasites, viruses or prions can be used to identify infection, prognosis, diagnosis, efficacy of treatment or progression of treatment for infection by such etiological agents.

The chamber is optionally washed to remove unbound materials and introduced into the chamber are antibodies detectably labeled with fluorescent labels. There are eight of such antibodies, each with the same or a different label, or combinations thereof. The labeled antibodies correspond to the antibodies that are immobilized on the functional layer. A sandwich between the immobilized antibody, the cell and the secondary labeled antibodies form.

The chamber is washed to remove unbound materials. The chip is irradiated with electromagnetic radiation at a wavelength or wavelengths to excite the detectable labels. The emission from the chip is collected using a CCD device. The image is then stored on an appropriate storage medium, such as a magnetic disk or CD. Optionally, a MR head can be used to identify the location of the magnetic particles on the chip.

Figure 40:
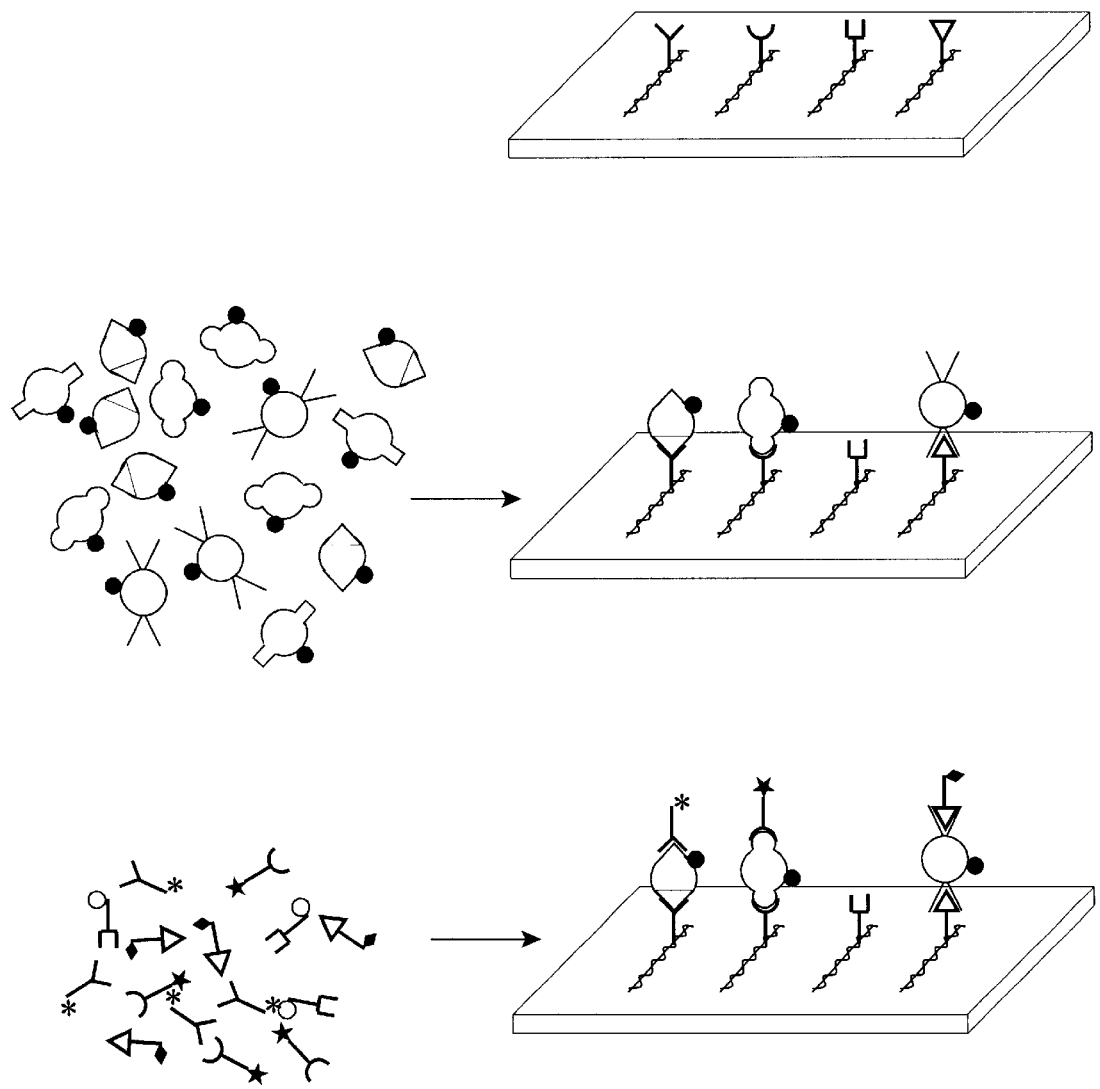
FIG. 40 depicts one aspect of a method of detecting a distribution of cells, such as lymphocytes in a sample using a method of the present, preferably traveling wave magentophoresis.

The pattern of fluorescence on the chip is indicative of the population of white blood cells in the sample, particularly the presence of lymphoma in the samples. This method allows for the classification and subclassification of lymphomas based on the population of white blood cells present in the sample (FIG. 40).

All publications, including patent documents and scientific articles, referred to in this application and the bibliography and attachments are incorporated by reference in their entirety for all purposes to the same extent as if each individual publication were individually incorporated by reference.

All headings are for the convenience of the reader and should not be used to limit the meaning of the text that follows the heading, unless so specified.

What is claimed is:

1. An electromagnetic chip with individually addressable micro-magnetic units comprising:
   a) a substrate;
   b) a plurality of micro-electromagnetic units on or within said substrate, substantially all of said micro-electromagnetic units structured to produce a magnetic field upon application of an electric field thereto; and
   means for selectively applying an electric current to one or more of said plurality of micro-electromagnetic units to produce a magnetic field therein,
      wherein at least one of said micro-electromagnetic units is in a substantially horizontal configuration.

2. The electromagnetic chip of claim 1, wherein each micro-electromagnetic unit comprises:
   a) a core on or within said substrate and
   b) means for conducting an electric current about said magnetic core;
      wherein said core is a magnetic core or a magnetizable core.

3. The electromagnetic chip of claim 2, wherein said core comprises a ferromagnetic material or a ferrimagnetic material.

4. The electromagnetic chip of claim 2, wherein said means for conducting an electric current about said core comprises single or multiple loops of electric conductive traces around said core.

5. The electromagnetic chip of claim 4, wherein said loops of electric conductive traces are of a circular, a square, an elliptical, a triangular, a spiral or a squared-spiral shape and further wherein said loops of electric conductive traces are in the same plane or different planes.

6. The electromagnetic chip of claim 4, further comprising means for modulating a magnitude and a polarity of the electric current selectively applied to any one of said micro-electromagnetic units.

7. The electromagnetic chip of claim 1, wherein said means for selectively applying comprises conductive connections between a micro-electromagnetic unit and a source of electric current and switch means for alternately interrupting and establishing a flow of electric current through the conductive connections.

8. The electromagnetic chip of claim 7, wherein said switch means are mechanical, electronic or a combination thereof.

9. The electromagnetic chip of claim 1, wherein said mirco-electromagnetic units are arranged on or within said substrate in a substantially regular, repetitive pattern with substantially equal distances between neighboring units.

10. The electromagnetic chip of claim 1, wherein said micro-electromagnetic units have dimensions of width and length ranging between about 0.1 micrometer and about 1 cm.

11. The electromagnetic chip of claim 1, further comprising at least one functional layer; wherein said functional layer can immobilize at least one moiety or ligand.

12. The electromagnetic chip of claim 11, wherein said functional layer is selected from the group consisting of a hydrophilic molecular monolayer, a hydrophilic molecular monolayer with functional groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups.

13. The electromagnetic chip of claim 12, wherein said functional groups are selected from the group consisting of aldehydes, carbodiimides, succinimydyl esters, antibodies, receptors and lectins.

14. The electromagnetic chip of claim 11, further comprising at least one moiety or ligand immobilized on or within said functional layer.

15. The electromagnetic chip of claim 14, wherein said moiety or ligand comprise a material selected from the group consisting of nucleic acid molecules, DNA, RNA, polypeptides, proteins, carbohydrates, lipids, prokaryotic cells, eukaryotic cells, prions, viruses, parasites, antibodies, lectins or receptors.

* * * * *